United States Patent
Tominaga et al.

(10) Patent No.: US 7,318,966 B2
(45) Date of Patent: Jan. 15, 2008

(54) LUMINESCENT ELEMENT MATERIAL AND LUMINESCENT ELEMENT COMPRISING THE SAME

(75) Inventors: Tsuyoshi Tominaga, Otsu (JP); Daisuke Kitazawa, Otsu (JP); Aki Makiyama, Otsu (JP); Akira Kohama, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 10/221,342

(22) PCT Filed: Nov. 22, 2001

(86) PCT No.: PCT/JP01/10214

§ 371 (c)(1),
(2), (4) Date: Sep. 11, 2002

(87) PCT Pub. No.: WO02/43449

PCT Pub. Date: May 30, 2002

(65) Prior Publication Data

US 2003/0168970 A1    Sep. 11, 2003

(30) Foreign Application Priority Data

Nov. 24, 2000 (JP) .............................. 2000-357129
Jun. 8, 2001 (JP) .............................. 2001-173610

(51) Int. Cl.
*H01J 1/62* (2006.01)
*C07F 9/02* (2006.01)

(52) U.S. Cl. ................ 428/690; 428/917; 313/504; 313/506; 257/40; 558/420; 558/167; 556/415

(58) Field of Classification Search ............... 428/690, 428/917; 313/504, 506; 257/40; 252/301.16; 558/167, 420; 556/415
See application file for complete search history.

(56) References Cited

U.S. PATENT DOCUMENTS

| | | | |
|---|---|---|---|
| 5,393,614 A | 2/1995 | Nakada | |
| 5,763,636 A * | 6/1998 | Kreuder et al. | 558/46 |
| 5,817,430 A * | 10/1998 | Hsieh | 428/690 |
| 6,248,457 B1 | 6/2001 | Chen et al. | |
| 6,329,082 B1 * | 12/2001 | Kreuder et al. | 428/690 |
| 6,406,804 B1 * | 6/2002 | Higashi et al. | 428/690 |
| 6,444,333 B1 * | 9/2002 | Okada et al. | 428/690 |
| 6,504,042 B1 * | 1/2003 | Lupo et al. | 558/46 |
| 6,621,840 B2 * | 9/2003 | Araki | 372/39 |
| 6,670,051 B2 * | 12/2003 | Oda et al. | 428/690 |
| 2002/0096995 A1 * | 7/2002 | Mishima et al. | 313/506 |

FOREIGN PATENT DOCUMENTS

| | | |
|---|---|---|
| DE | 195 05 942 | 8/1996 |
| EP | 0 934 992 | 8/1999 |
| EP | 0 982 411 A2 | 3/2000 |
| JP | 5-331459 | 12/1993 |
| JP | 9-20885 | 1/1997 |
| JP | 9-232077 | 9/1997 |
| JP | 11-273863 | 10/1999 |
| JP | 11-312589 | 11/1999 |
| JP | 11-329734 | 11/1999 |
| JP | 2000-68055 | 3/2000 |
| JP | 2000-508686 | 7/2000 |
| JP | 2001-267080 * | 9/2001 |
| WO | WO 00/03565 | 1/2000 |

OTHER PUBLICATIONS

Yeh et al., "Synthesis, Properties, and Applications of Tetraphenylmethane-Based Molecular Materials for Light-Emitting Devices", Chemical Materials, 2001, 13, pp. 2788-2796.*
Supplementary Partial European Search Report dated Feb. 27, 2007, directed to counterpart EP application No. 01 99 7977.
Supplementary European Search Report dated Sep. 3, 2007, directed to counterpart EP application No. 01997977.2 (5 pages).

* cited by examiner

*Primary Examiner*—Milton I. Cano
*Assistant Examiner*—Camie S. Thompson
(74) *Attorney, Agent, or Firm*—Morrison & Foerster LLP

(57) ABSTRACT

A light emitting device includes an emissive substance between an anode and cathode that emits light upon application of electrical energy. The emissive substance included in the device is at least one of the following types of compounds: (a) a compound having a plurality of 1,7-phenanthroline skeletal structures; (b) a benzoquinoline derivative; (c) a spiro compound; and (d) a tetraphenylmethane derivative.

15 Claims, No Drawings

LUMINESCENT ELEMENT MATERIAL AND LUMINESCENT ELEMENT COMPRISING THE SAME

TECHNICAL FIELD

The present invention relates to light emitting device materials and to a light emitting device which can convert electrical energy into light and can be used for display elements, flat panel displays, back lights, lighting, interiors, signs, signboards, electronic cameras, light signal generators and the like.

TECHNICAL BACKGROUND

There has recently been considerable research into organic multi-layered thin film light-emitting devices which emit light when electrons injected from a cathode and holes injected from an anode recombine within an organic fluorescent body interposed between the electrodes. Such devices are a focus of attention on account of their characteristics of thin shape, high luminance at low driving voltage and polychromic light emission based on suitable selection of the fluorescent materials.

Numerous research organizations have been carrying out such research since C. W. Tang and co-workers at Kodak first described the fact that an organic multi-layered thin film element emits light of high luminance (Appl. Phys. Lett. 51(12) 21, p. 913, 1987). A typical organic multi-layered thin film light-emitting element construction proposed by the Kodak research group is that in which there are provided, in turn, on an ITO glass substrate, a hole transporting diamine compound, 8-hydroxyquinoline aluminium as the emissive layer and Mg:Ag as the cathode, and 1,000 cd/m² green coloured light emission is possible at a driving voltage of about 10 V.

In this organic multi-layered thin film light-emitting device structure, as well as the aforesaid anode/hole transporting layer/emissive layer/cathode, there may also be suitably provided an electron transporting layer. The hole transporting layer has the function of transporting the holes injected from the anode to the emissive layer, while the electron transporting layer transports the electrons injected from the cathode to the emissive layer. By interposing these layers along with the emissive layer between the two electrodes, the luminance efficiency and the durability are enhanced. As examples of device structures employing these, there are structures comprising an anode/hole transporting layer/emissive layer/electron transporting layer/cathode and an anode/emissive layer/electron transporting layer/cathode, etc.

However, many conventional emissive materials, hole transporting materials and electron transporting materials lack durability, and crystallization takes place due to the heat evolved from the device by the prolonged passage of current, so that the device life is shortened.

In particular, taking the case of the electron transporting material, with many of the existing materials there are problems such as the desired emission colour not be obtained for reasons such as interaction with the emissive material or there being admixed light emission by the electron transporting material itself, while even where highly efficient emission is obtained the durability is poor. In U.S. Pat. No. 5,393,614, a specific phenanthroline derivative is used as the electron transporting material, but while highly efficient emission is shown there is crystallization during prolonged operation, and the thin film turns cloudy. Quinolinol metal complexes and benzoquinolinol metal complexes are also materials which show comparatively good characteristics in terms of luminance efficiency and durability but, since these materials themselves have a high emissive capacity in the blue-green to yellow region, when employed as electron transporting materials there is admixed emission from these materials themselves and the chromatic purity is adversely affected.

The present invention has the objective of resolving such problems of the prior-art and offering a light emitting device which is excellent in its thermal stability, has high luminance efficiency, high luminance and excellent chromatic purity.

DISCLOSURE OF THE INVENTION

The light emitting device of the present invention relates to a light emitting device which is characterized in that it is a device with an emissive material present between an anode and cathode, and which emits light by means of electrical energy, and, said device has a least one type of compound denoted by (a) to (d) below.

(a) A compound having a plurality of 1,7-phenanthroline skeletal structures
(b) A benzoquinoline derivative
(c) A Spiro compound represented by general formula (1)

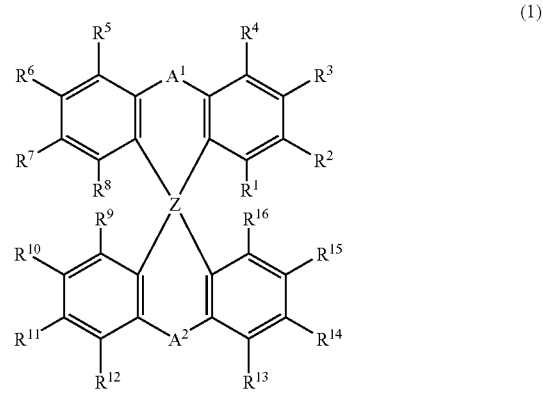

(1)

$A^1$ and $A^2$ are each selected from single bonds, substituted or unsubstituted alkyl chains, ether chains, thioether chains, ketone chains and substituted or unsubstituted amino chains. However, $A^1 \neq A^2$. Z represents carbon or silicon. $R^1$ to $R^{16}$ are each selected from hydrogen, alkyl group, cycloalkyl group, aralkyl group, alkenyl group, cycloalkenyl group, alkynyl group, hydroxyl group, mercapto group, alkoxy group, alkylthio group, aryl ether group, aryl thioether group, aryl group, heterocyclic group, halogen, haloalkane, haloalkene, haloalkyne, cyano group, aldehyde group, carbonyl group, carboxyl group, ester group, carbamoyl group, amino group, nitro group, silyl group, siloxanyl group and a cyclic structure formed with an adjacent substituent.

(d) A tetraphenylmethane derivative represented by general formula (2)

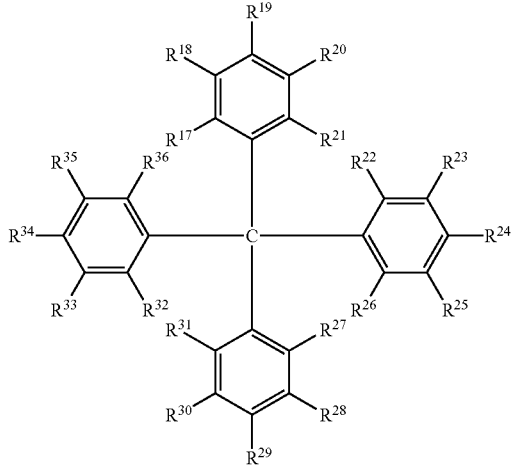

(2)

$R^{17}$ to $R^{36}$ are each selected from hydrogen, alkyl group, cycloalkyl group, aralkyl group, alkenyl group, cycloalkenyl group, alkynyl group, hydroxyl group, mercapto group, alkoxy group, alkylthio group, aryl ether group, aryl thioether group, aryl group, heterocyclic group, halogen, haloalkane, haloalkene, haloalkyne, cyano group, aldehyde group, carbonyl group, carboxyl group, ester group, carbamoyl group, amino group, nitro group, silyl group, siloxanyl group and a cyclic structure formed with an adjacent substituent. However, at least one of $R^{17}$ to $R^{36}$ is selected from substituents represented by general formula (3).

—X—Ar         (3)

X is a single bond or is selected from the following, and Ar denotes a condensed aromatic ring or heteroaromatic ring. In the case where X is phosphorus oxide, then Ar represents an aromatic hydrocarbon or heteroaromatic ring.

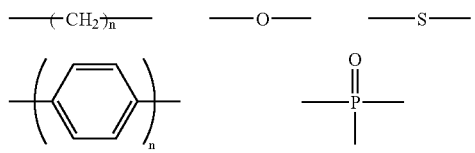

n designates a natural number.

Optimum Form for Practising the Invention

The electron transporting layer of the present invention is the layer into which electrons are injected from the cathode and which transports the electrons, and it is desirable that the electron injection efficiency be high and that the injected electrons are highly efficiently transported. However, taking into account the hole and electron transportation balance, in the case where its role is primarily to efficiently block the flow of holes from the anode to the cathode without recombination, then, even if the electron transporting capacity of the electron transporting layer is not all that high, its effect in terms of enhancing the luminance efficiency will be the same as that of a material with a high electron transportation capacity. Consequently, electron transporting layer in the present invention will encompass within the same definition a hole blocking layer which can efficiently inhibit the transport of holes.

The material from which the electron transporting layer of the present invention is composed is an organic compound of molecular weight at least 400. With an organic compound of molecular weight less than 400, the electron transporting layer will be thermally unstable and readily crystallize, so that stable emission is not obtained in terms of prolonged operation. A molecular weight of at least 600 is further preferred.

The material from which the electron transporting layer of the present invention is composed has a glass transition temperature of at least 90° C., more preferably at least 120° C. and still more preferably at least 150° C. Furthermore, a film of a compound of high cold crystallization temperature does not readily crystallize, and it is preferred that the cold crystallization temperature be at least 140° C., more preferably at least 170° C. and still more preferably at least 200° C. Moreover, it is desirable that it be a compound where no cold crystallization temperature is observed. Reference here to no cold crystallization temperature being observed means that when the glass transition temperature and the cold crystallization temperature of a sample are measured, no clear cold crystallization temperature is found when the temperature of the sample is raised at a certain fixed rate. The glass transition temperature and the cold crystallization temperature are measured using a differential scanning calorimeter based on temperature-modulated DSC.

The ionization potential of the material from which the electron transporting layer of the present invention is composed, will be at least 5.9 eV. When the ionization potential is at least 5.9 eV, it is possible to prevent very efficiently the holes injected from the anode from flowing to the cathode side without recombining within the emissive layer, so the luminance efficiency is enhanced. Furthermore, since the electron transporting layer itself does not fluoresce, light emission of high chromatic purity is obtained only from the emissive layer. More preferably, the value is at least 6.0 eV. The absolute value of the ionization potential will differ according to the measurement method but, in the present invention, measurement is carried out with an atmospheric air type UV photoelectron analyzer (AC-1, produced by the Riken Keiki Co. Ltd) using a thin film evaporated onto an ITO glass substrate.

Moreover it is also preferred that the ionization potential of the electron transporting layer of the present invention be at least 0.1 eV greater than the ionization potential of the emissive layer. In the case where there is a difference in ionization potential of at least 0.1 eV between the adjacent electron transporting layer and emissive layer, it is possible to efficiently prevent the holes injected from the anode from flowing to the cathode side without recombining within the emissive layer. In terms of a high temperature operational environment, it is further preferred that this difference be at least 0.15 eV and still more preferably at least 0.2 eV. The difference in the ionization potentials in the present invention is calculated from the ionization potentials of the respective individual layers measured on their own by the aforesaid method. Moreover, the value of the ionization potential will change with the state of the sample. Consequently, in the case where the emissive layer or the electron transporting layer is a mixed layer comprising two or more materials, the value of the ionization potential of this mixed layer is measured.

The organic compound from which the electron transporting layer is composed preferably contains a plurality of parent skeletal structures having an electron transporting capacity, with this plurality of parent skeletal structures being connected together by connecting units. The phenanthroline structure and the benzoquinoline structure are preferred examples of such parent skeletal structures with an electron transporting capacity. In addition to having an electron transporting capacity, a high ionization potential is obtained with a phenanthroline structure or benzoquinoline structure. In the case where the electron transporting capability is inadequate with the phenanthroline or benzoquinoline structures alone, these phenanthroline or benzoquinoline structures may be provided with a functional group with an electron transporting capacity such as the vinyl group, carbonyl group, carboxyl group, aldehyde group, nitro group, cyano group, halogen, sulphone, phosphorus oxide or the like. Of these, phosphorus oxide is preferred.

With regard to the connecting units for connecting together the phenanthroline and/or benzoquinoline structures, connecting units which contain conjugated bonds, aromatic hydrocarbons or aromatic heterocycles are preferred, and the following can be given as specific examples.

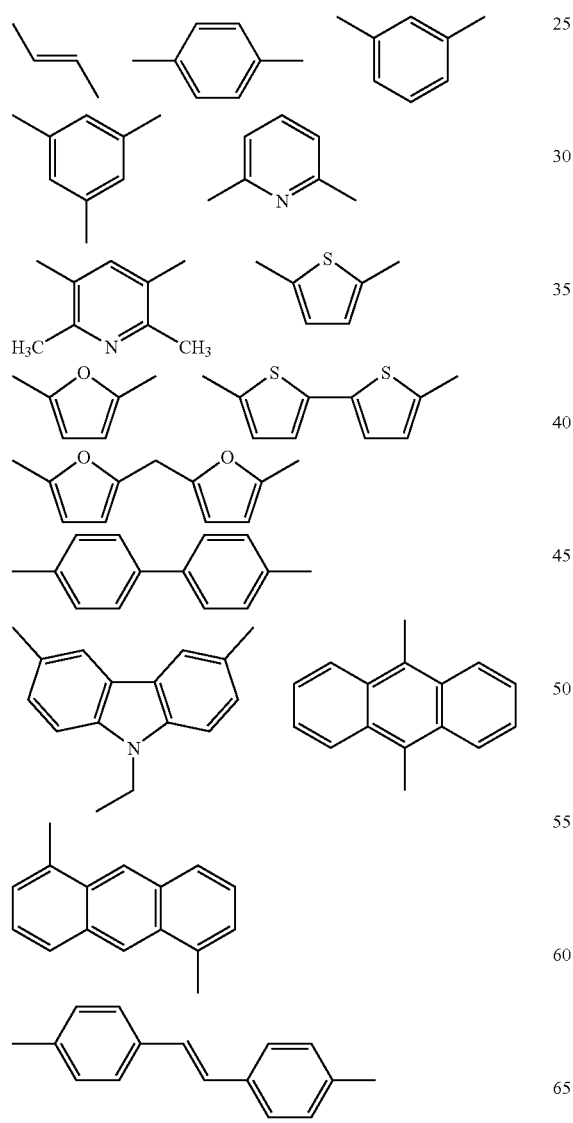

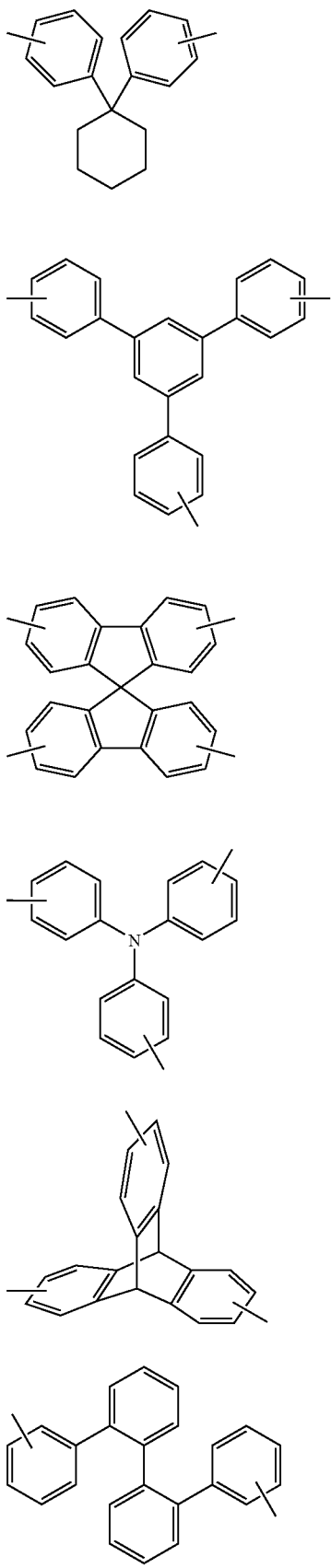

-continued
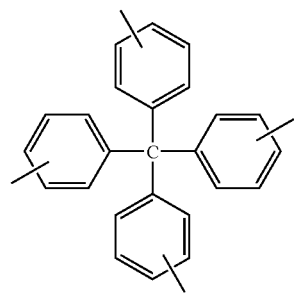
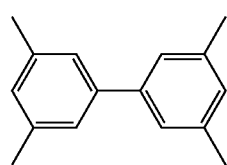
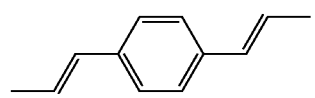
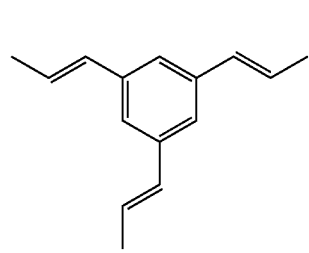
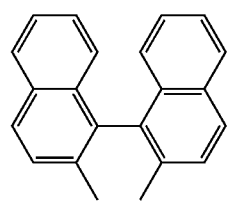
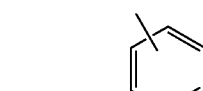
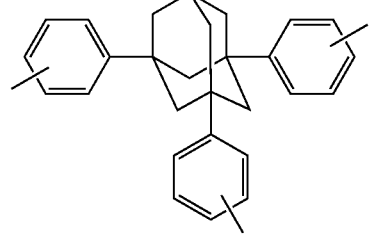
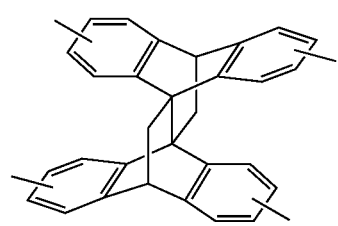
-continued
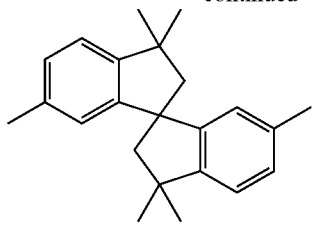
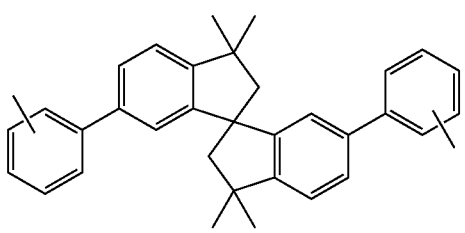
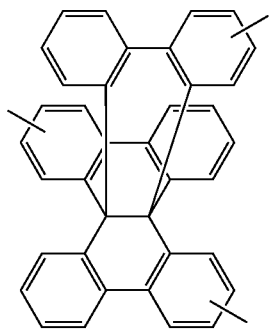
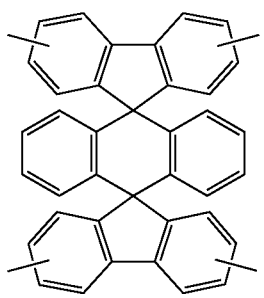
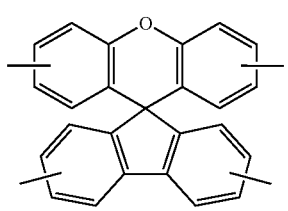
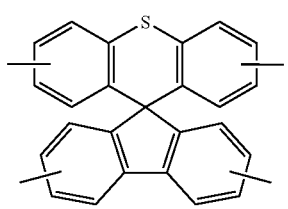

-continued

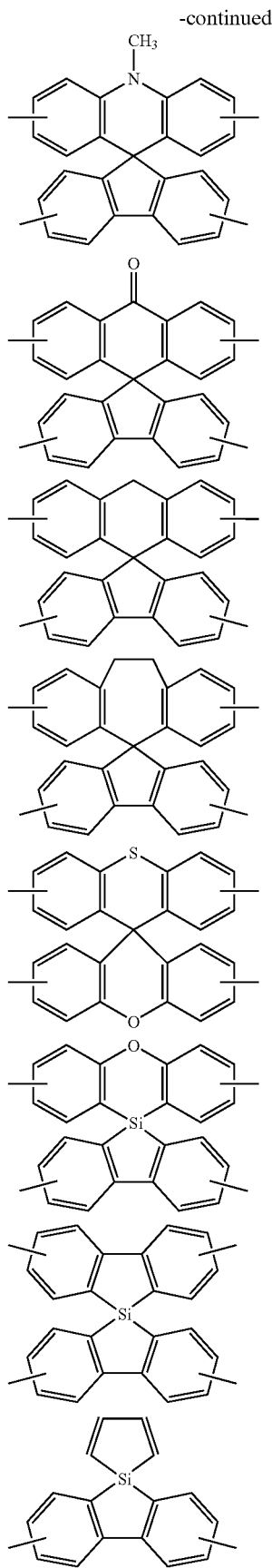

-continued

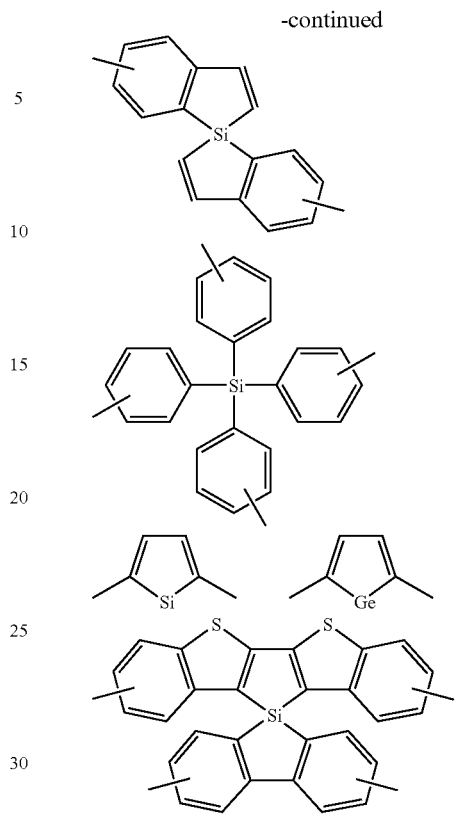

There may be used one type of connecting unit or a mixture thereof.

These connecting units are based on commercially available (coupling) compounds or they can be synthesized in accordance with normal procedures. Specific examples for a number of skeletal structures are shown below.

The synthesis of the 9,9'-spirobifluorene structure is described, for example, in J. Am. Chem. Soc., vol. 52 (1930), page 2881, and in U.S. Pat. No. 5,840,217 in the section "EXAMPLES A. Starting compounds a) Synthesis of 9,9'-spirobifluorene". Thus, 2-bromobiphenyl is converted to the Grignard in THF using metal magnesium, then reacted with 9-fluorenone at room temperature to 50° C. and treatment carried out in the usual way, after which the hydroxy compound obtained is subjected to heating and elimination of water in acetic acid to which a small amount of hydrochloric acid has been added and treatment performed in the usual way.

The synthesis of the 9,9'-spirobi(9H-9-silafluorene) structure is described in J. Am. Chem. Soc., vol. 80 (1958), page 1883. This can be obtained by reacting 2,2'-dibromobiphenyl with metal lithium in ether, and then performing reaction with tetrachlorosilane at a specified temperature, followed by treatment in the usual way.

The synthesis of the hexabenzopropellane structure is described in for example Libigs Ann. Chem., vol. 749 (1971) page 38. 9-fluorenone is reacted with triethyl phosphite, then treatment performed with methanol and the spiroketone compound obtained. Next, reaction is conducted in ether at a specified temperature between a 2-bromobiphenyl lithio compound and the spiroketone compound, followed by treatment in the usual way, and then hydroxy compound obtained is subjected to heating and elimination of water in acetic acid with the addition of methanesulphonic acid, and treatment performed in the usual way.

Examples of the phenanthroline skeletal structure in the present invention are shown by general formulae (4) to (6).

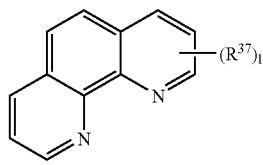

(4)

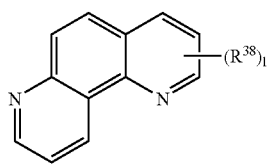

(5)

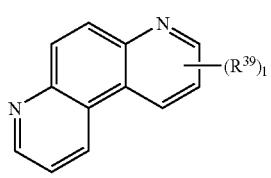

(6)

$R^{37}$ to $R^{39}$ in general formulae (4) to (6) denote substituents provided at any position in the phenanthroline skeletal structure other than a position used for connection. Specifically, they may be selected from amongst hydrogen, alkyl groups such as the methyl group and ethyl group, cycloalkyl groups such as cyclohexyl and norbomyl, aralkyl groups such as the benzyl group, alkenyl groups such as the vinyl group and allyl group, cycloalkenyl groups such as the cyclopentadienyl group and cyclohexenyl group, alkoxy groups such as the methoxy group, alkylthio groups where the oxygen atom of the ether linkage in an alkoxy group is replaced by a sulphur atom, aryl ether groups such as the phenoxy group, aryl thioether groups where the oxygen atom of the ether linkage in an aryl ether group is replaced by a sulphur atom, aryl groups such as the phenyl group, naphthyl group or biphenyl group, heterocyclic groups such as the furyl group, thienyl group, oxazolyl group, pyridyl group, quinolyl group and carbazolyl group, halogens, cyano group, aldehyde group, carbonyl group, carboxyl group, ester group, carbamoyl group, amino group, nitro group, silyl groups such as the trimethylsilyl group, siloxanyl groups which are groups with silicon having an interposed ether linkage, and cyclic structures formed with an adjacent substituent group. These substituents may themselves be unsubstituted or substituted. 'l' in the formulae indicates an integer in the range 1 to 8. In the case where there are a plurality of substituents, said substituents may be the same or different.

Taking the particular case where the basic phenanthroline structure is denoted by general formula (4), examples of compounds where the phenanthroline constitutes the parent skeletal structure may be represented by general formula (7).

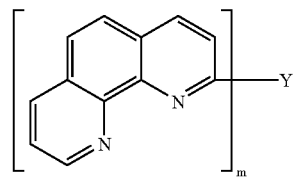

(7)

Here Y is a connecting unit as described above, and m is a natural number of value 2 or more.

In the case where the parent skeletal structure is that shown by aforesaid general formula (5), examples of compounds having a plurality of 1,7-phenanthroline structures are represented by general formula (8).

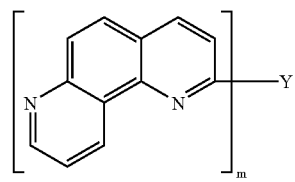

(8)

Here Y is a connecting unit as described above, and m is a natural number of value 2 or more.

The compounds of the present invention having a plurality of 1,7-phenanthroline structures exhibit a blue fluorescence and they can also be used as compounds for forming the emissive layer.

For the purposes of introducing the phenanthroline parent skeletal structure into a connecting unit, there is the method of introducing a reactive substituent such as an acetyl group, after which the phenanthroline ring is formed, or the method of introducing a reactive substituent such as an iodo or bromo group, after which addition of the phenanthroline ring is carried out.

A method for introducing an acetyl group is the usual, simple, Friedel-Crafts acylation method. As examples of literature references, there may be cited the section of U.S. Pat. No. 5,840,217 entitled "EXAMPLES A. Starting compounds f", 9,9'-spirobifluorene-2,2'-dicarboxylic acid from 9,9'-spirobifluorene via 2,2'-diacetyl-9,9'-spirobifluorene, and "Experimenteller Tell 2,2'-diacetyl-9,9'-spirobifluorene (IV)" in Helvetica Chimica Acta, vol. 52 (1969), page 1210. Acetyl groups can be introduced by reacting the connecting unit with acetyl chloride and aluminium chloride in 1,2-dichloroethane at 50° C., followed by treatment in the normal way.

Literature references describing a method for the introduction of the phenanthroline parent skeletal structure starting from the acetyl group include Tetrahedron Letters, vol. 40 (1999), the scheme on page 7312; J. Org. Chem. 1996, 61, page 302 "2-phenyl-1, 10-phnantholine" and Tetrahedron Letters, vol. 23 (1982), pages 5291-5294. The acetyl derivative of the connecting unit is reacted with potassium hydroxide and the corresponding quinoline derivative, such as 8-amino-7-quinolinecarbaldehyde, in dioxane at 60° C. and treatment carried out in the usual way.

Literature references on the introduction of an iodo group include J. Chem. Soc. Japan, Pure Chem. Section (Nihon Kagaku Zasshi) vol. 92, no. 11 (1971) page 1023 "1.1 Iodination of 1-methylnaphthalene, and Tetrahedron Letters, vol. 38 (1997), page 1487. The iodo group can be introduced by reacting the connecting unit with iodine and periodic acid dihydrate at 80° C. in 80% acetic acid and treating in the usual way, or by reaction with iodine and bis(trifluoroacetoxy)iodobenzene at 50-60° C. in carbon tetrachloride and treating in the usual way.

Literature references on the introduction of the bromo group include U.S. Pat. No. 5,840,217, the section "EXAMPLES A. Starting compounds a) Synthesis of 9,9'-spirobifluorene", and Angew. Chem. Int. Ed. Engl. 25 (1986) No. 12, page 1098. The bromo group can be introduced by reacting the connecting unit with bromine at room temperature and treating in the usual way.

As a method for the introduction of the phenanthroline skeletal structure starting from the iodo or bromo group, there is the method in which the iodo or bromo derivative of the connecting unit is converted to the lithio form using metal lithium, and then reaction carried out with the corresponding anhydrous phenanthroline, followed by treatment with water and manganese dioxide.

Moreover, the introduction of the phenanthroline skeletal structure into the connecting unit is not restricted to the aforesaid method of firstly synthesizing the connecting unit and then introducing a reactive substituent therein. By using a starting material containing a reactive substituent at the time of the synthesis of the connecting unit, there may be directly obtained the connecting unit in which the reactive substituent has been introduced. For example, the synthesis of the following connecting unit with introduced acetyl groups can be carried out by the reaction of 4-acetylphenylboronic acid with 2,2'-dibromobiphenyl under Suzuki coupling conditions (literature reference: Chem. Rev., vol. 95 (1995) page 2457).

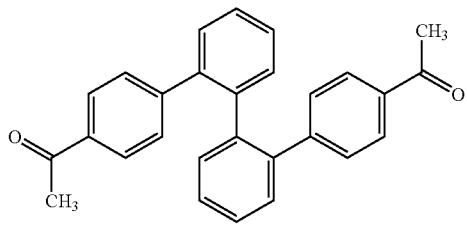

The organic compounds from which the emissive layer and the electron transporting layer are composed are preferably compounds which can sublime. Here, 'can sublime' means that when heated in a vacuum they volatilize without decomposition, and so thin-film formation is possible. The light emitting device of the present invention has a multi-layered structure so, where there is employed an organic compound which can sublime, it is possible to form a multi-layered structure readily using a dry process such as vacuum vapour deposition. Again, in the case of the formation of a doping layer within the emissive layer, by employing the method of co-evaporation along with the host material or the method of simultaneous evaporation after prior-mixing with the host material, it is possible to form the doping layer with an outstanding degree of control. Furthermore, in a display device where display is effected by the matrix or segment system, it is necessary to obtain emission in a desired pattern and organic compounds which can sublime can readily be patterned by a dry process.

The electron transporting layer of the present invention is not necessarily restricted to one type of aforesaid organic compound and a plurality of such materials may be mixed together or provided as a multilayer. In the case of a multilayer, the aforesaid parameters may be satisfied by the single layer adjacent to the emissive layer. Furthermore, with the objective of enhancing the transportation capacity of the electron transporting layer as a whole, or with the objective of enhancing the thermal or electrochemical stability, the electron transporting layer may be formed by adding, to the electron transporting material, an organic compound, inorganic compound or metal complex which does not have an electron transporting capacity.

The emissive layer is the layer where the emissive substance is actually formed, and the emissive substance may be composed of one type of organic compound or there may be employed a mixed layer comprising two or more types of organic compound. From the point of view of enhancing the luminance efficiency, chromatic purity and durability, the emissive layer is preferably composed of two or more types of organic compound. An example of a combination of two or more types of organic compound is the combination of a host material and a dopant material. In such circumstances, the host material primarily has the emissive layer thin-film forming-ability and carrier transporting capacity, while the dopant material primarily has the emission ability. As emission mechanisms, there are the energy transfer type and the carrier trap type. In the energy transfer type, the carriers injected from the two electrodes recombine within the host layer and the host material is excited. Energy transfer occurs from the excited host material to the dopant material, and finally emission is obtained from the dopant material. In the carrier trap type, carriers which have moved through the host layer directly recombine on the dopant material, and the excited dopant emits light. In each case, if there is used as the dopant material, which has the emissive function, a material with high chromatic purity in the solution state and a high photoluminescent quantum yield, it is possible to obtain high chromatic purity and high luminance efficiency. Furthermore, the addition of a dopant material serves to lower the crystallinity of the host layer film, which is the film parent body, and for this reason too the durability is enhanced.

In the case where there is used this kind of combination of host material and dopant material, the dopant material can be contained within the entirety of the host material or it may be contained in a part thereof. Furthermore, the dopant material may be provided as a layer or it may be dispersed.

The organic material in the case where it alone forms the emissive layer, or the host material in the case of a combination of host and dopant materials, may be a derivative of a condensed ring system such as anthracene, pyrene or perylene, a derivative of a heterocycle such as pyrazine, naphthyridine, quinoxaline, pyrrolopyridine, pyrimidine, thiophene or thioxanthene, a quinolinol-metal complex such as the tris(8-quinolinolato)aluminium complex, a benzoquinolinol-metal complex, a bipyridine-metal complex, a rhodamine-metal complex, an azomethine-metal complex, a distyrylbenzene derivative, a tetraphenylbutadiene derivative, a stilbene derivative, an aldazine derivative, a coumarin derivative, a phthalimide derivative, a naphthalimide derivative, a perinone derivative, a pyrrolopyrrole derivative, a cyclopentadiene derivative, an imidazole derivative, an oxazole derivative, a thiazole derivative, an oxadiazole derivative, a thiadiazole derivative, a triazole derivative or other such azole derivative or metal complex thereof, a benzoxazole, benzimidazole, benzothiazole or other such benzazole derivative or metal complex thereof, an amine derivative such as a triphenylamine derivative or carbazole derivative, a merocyanine derivative, a porphyrin derivative, tris(2-phenylpyridine)iridium complex or other such phosphorescent material or, in the case of polymer systems, a polyphenylene vinylene derivative, poly-p-phenylene derivative or polythiophene derivative, or the like.

Examples of the dopant material are anthracene, perylene and other such condensed polycyclic aromatic hydrocarbon derivatives, 7-dimethylamino-4-methylcoumarin and other such coumarin derivatives, bis(diisopropylphenyl)-perylenetetracarboxylic imide and other such naphthalimide derivatives, perinone derivatives, rare earth complexes such as Eu complexes with an acetylacetone, benzoylacetone or phenanthroline ligand, dicyanomethylene pyran derivatives, dicyanomethylene thiopyran derivatives, magnesium phthalocyanine, aluminium chlorophthalocyanine and other such metal-phthalocyanine derivatives, porphyrin derivatives, rhodamine derivatives, deazaflavin derivatives, coumarin derivatives, oxazine compounds, thioxanthene derivatives, cyanine dye derivatives, fluorescein derivatives, acridine derivatives, quinacridone derivatives, pyrrolopyrrole derivatives, quinazoline derivatives, pyrrolopyridine derivatives, squarilium derivatives, violanthrone derivatives, phenazine derivatives, acridone derivatives, pyrromethene derivatives and their metal complexes, phenoxazine derivatives, phenoxazone derivatives, thiadiazolopyrene derivatives, tris(2-phenylpyridine)iridium complex, tris(2-phenylpyridyl)-iridium complex, tris[2-(2-thiophenyl)pyridyl]iridium complex, tris[2-(2-benzothiophenyl)pyridyl]iridium complex, tris(2-phenylbenzothiazol)iridium complex, tris(2-phenylbenzoxazole)iridium complex, trisbenzoquinoline-iridium complex, bis(2-phenylpyridyl)(acetylacetonato) iridium complex, bis[2-(2-thiophenyl)pyridyl]iridium complex, bis[2-(2-benzothiophenyl)pyridyl](acetylacetonato)iridium complex, bis(2-phenylbenzothiazole)(acetylacetonato)-iridium complex, bis(2-phenylbenzoxazole) (acetyl-acetonato)iridium complex, bisbenzoquinoline (acetyl-acetonato )iridium complex, platinum-porphyrin complex and other such phosphorescent materials. These may be used on their own or a mixture of a plurality of such derivatives may be used.

Furthermore, for the purposes of modifying the film properties or trapping excess carriers and enhancing the durability, there may sometimes be added a dopant material without it having an emissive capacity. As the dopant material in such circumstances, there is selected from amongst various organic and inorganic compounds one which corresponds to the host material. The doping conditions are the same as above.

In terms of the objective of achieving efficient recombination of the holes and the electrons within the emissive layer, it is preferred that the light emitting device of the present invention also has a hole transporting layer between the anode and the emissive layer. The hole transporting layer is a layer which further transports the holes after they have been injected from the anode. Examples of hole transporting materials are N,N'-diphenyl-N,N'-bis(3-methylphenyl)-4,4'-diphenyl-1,1'-diamine, N,N'-bis(1-naphthyl)-N,N'-diphenyl-4,4'-diphenyl-1,1'-diamine and other such triphenylamines, bis(N-arylcarbazoles) or bis(N-alkylcarbazoles), pyrazoline derivatives, stilbene derivatives, distyryl derivatives, hydrazone compounds, oxadiazole derivatives, phthalocyanine derivatives, porphyrin derivatives and other such heterocyclic compounds and, in the case of polymer systems, polycarbonates or styrene derivatives with the aforesaid monomers in side chains, polyvinylcarbazole, polysilanes and the like. These may be used on their own or there may be used a plurality in the form of a mixture or multilayer. Furthermore, for the purposes of enhancing the transportation capacity of the entire hole transporting layer, or for enhancing the thermal stability or electrochemical stability, the formation of the hole transporting layer may be carried out with the addition of an organic compound, inorganic compound or metal complex which does not have a hole transporting capacity.

The anode in the present invention should be transparent in order to extract the light. Examples include electroconductive metal oxides such as tin oxide, indium oxide and indium tin oxide (ITO), or metals such as gold, silver and chromium, inorganic electroconductive substances such as copper iodide and copper sulphide, and electroconductive polymers such as polythiophene, polypyrrole and polyaniline. The use of ITO glass or NESA glass is particularly preferred. With regard to the resistance of the transparent electrode, it should be possible to supply sufficient current to achieve emission and a low resistance is preferred from the point of view of the power consumption of the device. For example, an ITO substrate of resistance no more than 300 $\Omega/\square$ will function as a device electrode but, since there currently exist substrates of resistance value about 10 $\Omega/\square$, using a low resistance product is particularly preferred. The thickness of the ITO can be freely selected in conjunction with the resistance value but normally there is usually employed a thickness in the range 100-300 nm. Furthermore, soda-lime glass, alkali-free glass or the like may be used as the glass substrate. Its thickness should be at least 0.5 mm in order to ensure mechanical strength. With regard to the type of glass material, an alkali-free glass is preferred in that there is little ion-elution from the glass but soda-lime glass can also be used where it has been given a barrier coating of $SiO_2$ or the like. Moreover, providing that the anode functions stably, the anode may also be formed on a plastic substrate. As examples of methods for forming an ITO film, there are the electron beam method, the sputtering method and the chemical reaction method, etc.

The cathode may be any substance which can efficiently inject electrons into the organic layer. Examples of the cathode material are platinum, gold, silver, copper, iron, tin, zinc, aluminium, indium, chromium, lithium, sodium, potassium, calcium, magnesium, caesium, strontium and the like. For the purposes of raising the electron injection efficiency and enhancing the characteristics of the device, lithium, sodium, potassium, calcium, magnesium, caesium, strontium or alloys of such low work function metals are effective. Furthermore, the method of doping the organic layer with a small amount of lithium, magnesium or caesium (a vacuum vapour-deposited film of no more than 1 nm as determined by means of a film thickness monitor) and using an electrode of high stability is also preferred, and moreover it is possible to employ an inorganic salt such as lithium fluoride. Again, for electrode protection, it is preferred that lamination be carried out with a metal such as platinum, gold, silver, copper, iron, tin, aluminium, indium or alloy of such metal, an inorganic material such as silica, titania or silicon nitride, or polyvinyl alcohol, vinyl chloride or a hydrocarbon polymer, etc. Examples of methods for the production of such electrodes are the resistance heating, electron beam, sputtering, ion plating and coating methods, etc.

The benzoquinoline skeletal structure in the present invention is a skeletal structure comprising benzene condensed to quinoline at any position, and it is represented by general formulae (9) to (14).

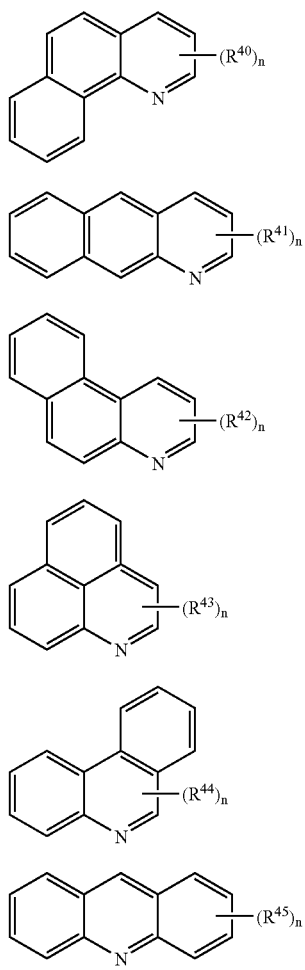

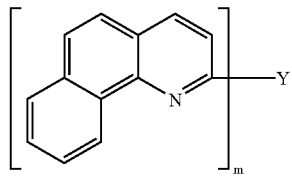

compounds based on the benzoquinoline parent skeletal structure are those with a structure represented by general formula (15).

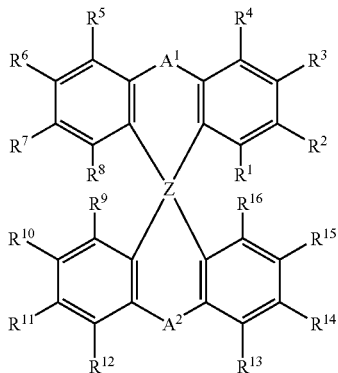

Here, Y and m are the same as for general formula (7).

The benzoquinoline derivatives of the present invention are outstanding in their electron transporting capacity and hole blocking capacity, so are preferably used as the electron transporting material.

The compounds of the present invention which possess a plurality of benzoquinoline skeletal structures can be synthesized by the same kinds of methods as the aforesaid phenanthroline derivatives. After introducing acetyl groups into the connecting unit, reaction is performed with a naphthalene derivative to form the benzoquinoline rings (literature reference: J. Org. Chem. 1996, 61, page 3021 "1,3-Di(benzo([h]quinolin-2-yl)benzene") or, alternatively, after introducing reactive substituents such as iodo or bromo groups, addition of the benzoquinoline rings is effected.

The spiro compounds represented by general formula (1) used in the light emitting device of the present invention are now explained.

$R^{40}$ to $R^{45}$ in general formulae (9) to (14) denote substituent groups at any position in the benzoquinoline skeletal structure other than a position used for connection, and they are the same as the substituents in the case of the phenanthroline skeletal structure. n is an integer in the range 1 to 8 and, in the case where there are a plurality of substituents, said substituents may be the same or different.

Furthermore, in order to obtain stable emission over a long period, a material with excellent thermal stability and thin-film forming properties is desirable. Amongst benzoquinoline derivatives, compounds having a plurality of benzoquinoline skeletal structures can be cited as still further preferred examples. Explanation of the benzoquinoline skeletal structure is the same as given above.

In order to obtain high luminance, the use of a compound with a high electron transporting capacity is preferred. Hence, as examples of the aforesaid compounds with a plurality of benzoquinoline skeletal structures, those compounds where said plurality of benzoquinoline skeletal structures are connected by a conjugated bond, aromatic hydrocarbon, aromatic heterocycle or mixture of these are further preferred.

Taking the case where the basic skeletal structure is represented by general formula (9), specific examples of $A^1$ and $A^2$ are each selected from a single bond, substituted or unsubstituted alkyl chain, ether chain, thioether chain, ketone chain and substituted or unsubstituted amino chain. However, $A^1 \ne A^2$. Z denotes carbon or silicon. $R^1$ to $R^{16}$ are each selected from hydrogen, alkyl group, cycloalkyl group, aralkyl group; alkenyl group, cycloalkenyl group, alkynyl group, hydroxyl group, mercapto group, alkoxy group, alkylthio group, aryl ether group, aryl thioether group, aryl group, heterocyclic group, halogen, haloalkane, haloalkene, haloalkyne, cyano group, aldehyde group, carbonyl group, carboxyl group, ester group, carbamoyl group, amino group, nitro group, silyl group, siloxanyl group and cyclic structure formed with an adjacent substituent.

Of these substituent groups, alkyl group refers to a saturated aliphatic hydrocarbon group such as the methyl group, ethyl group, propyl group or butyl group. Cycloalkyl group refers to a saturated alicyclic hydrocarbon group such as cyclopropyl, cyclohexyl, norbornyl or adamantyl. Aralkyl group refers to an aromatic hydrocarbon group with an interposed aliphatic hydrocarbon, such as the benzyl group or phenylethyl group. Alkenyl group refers to an unsaturated aliphatic hydrocarbon group which contains a double bond such as the vinyl group, allyl group or butadienyl group. Cycloalkenyl group refers to an unsaturated alicyclic hydrocarbon group containing a double bond such as the cyclopentenyl group, cyclopentadienyl group or cyclohexene group. Alkynyl group refers to an unsaturated aliphatic hydrocarbon group which contains a triple bond such as the acetylenyl group. Alkoxy group refers to an aliphatic hydrocarbon group with an interposed ether bond, such as the methoxy group. An alkylthio group is an alkoxy group where the oxygen atom of the ether bond is replaced by the sulphur atom. Arylether group refers to an aromatic hydrocarbon group with an interposed ether bond, such as the phenoxy group. An arylthioether group is an arylether group where the oxygen atom of the ether bond is replaced by the sulphur atom. An aryl group refers to an aromatic hydrocarbon group such as the phenyl group, naphthyl group, biphenyl group, phenanthryl group, terphenyl group or pyrenyl group. Heterocyclic group refers to a cyclic structure which has an atom other than carbon, such as the furyl group, thienyl group, oxazolyl group, pyridyl group, quinolyl group or carbazolyl group. The substituent, groups $R^1$ to $R^{16}$ may themselves be unsubstituted or they may be further substituted. Halogen refers to fluorine, chlorine, bromine or iodine. Haloalkane, haloalkene and haloalkyne respectively refer to the aforesaid alkyl, alkenyl and alkynyl groups which are in part or in total substituted with the aforesaid halogens, with any remaining parts being unsubstituted or otherwise substituted. The aldehyde group, carbonyl group, ester group, carbamoyl group and amino group may be substituted with aliphatic hydrocarbons, alicyclic hydrocarbons, aromatic hydrocarbons or heterocycles, etc, and furthermore these aliphatic hydrocarbons, alicyclic hydrocarbons, aromatic hydrocarbons and heterocycles may themselves be substituted or unsubstituted. Silyl group refers to a silicon compound group such as the trimethylsilyl group, and this may be substituted or unsubstituted. Siloxanyl group refers to a group which possesses silicon with an interposed ether bond, such as the trimethylsiloxanyl group, and this may be substituted or unsubstituted. A cyclic structure may be formed with an adjacent substituent group and the cyclic structure formed may be unsubstituted or substituted.

It is preferred that at least one of $R^1$ to $R^{16}$ contains a functional substituent group such as a hole-transporting substituent, an electron-transporting substituent, an emissive substituent or a thin-film forming substituent. Examples of hole-transporting substituents are the hole transporting material skeletal structures described above, and these structures may be substituted or unsubstituted. As electron-transporting substituents there are those based on electron transporting material skeletal structures like furan, pyrrole, thiophene, thiophene dioxide, pyrazole, imidazole, triazole, tetrazole, oxazole, oxadiazole, thiazole, thiadiazole, pyridine, pyridazine, pyrimidine, pyrimidone, pyrazine, triazine, aromatic heterocycles formed by ring fusion with the above such as benzofuran, dibenzofuran, indole, carbazole, benzothiophene, benzothiophene dioxide, dibenzothiophene, benzimidazole, phenanthroimidazole, benzoxazole, benzothiazole, quinoline, benzoquinoline, quinoxaline, quinazoline, naphthyridine, phenanthridine, phenanthroline, imidazopyridine, phenazinequinoxaline and the like, or aromatic hydrocarbons such as benzene, naphthalene, anthracene, phenanthrene, pyrene, styrene, stilbene and the like, where these structures may be unsubstituted or substituted. As examples of emissive substituents, there are structures based on the aforesaid emissive material (host material, dopant material) skeletal structures, where such structures may be unsubstituted or substituted. Fluorenyl, phenanthryl, anthranyl, pyrenyl, perylenyl and other such condensed aromatic rings, biphenyl, terphenyl, quaterphenyl and other such poly-p-phenylene derivatives, diphenylvinyl and the like are favourably employed. Alkyl groups, alkoxy groups, arylether groups and the like are preferably used as the thin-film forming substituents. The spiro compounds of the present invention can be used in the various layers of the light emitting device, depending on the type of functional substituents therein.

The number of functional substituents is preferably between one and four, with two or four being further preferred, and two still further preferred. The position of a functional substituent is preferably at $R^2$, $R^4$, $R^5$, $R^7$, $R^{10}$, $R^{12}$, $R^{13}$ or $R^{15}$, with $R^2$, $R^7$, $R^{10}$ or $R^{15}$ further preferred and $R^2$ and $R^{10}$ still further preferred.

Z is preferably carbon and one of $A^1$ and $A^2$ is preferably a single bond. When $A^2$ is a single bond then $A^1$ is preferably oxygen or sulphur, with oxygen further preferred. The compounds represented by general formula (1) have a sterically asymmetric central structure, so crystallization is prevented and the compounds are outstanding in their thin film stability.

The following specific structures can be given as examples of the aforesaid spiro compounds.

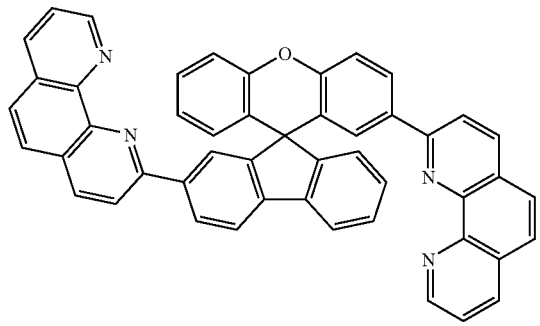 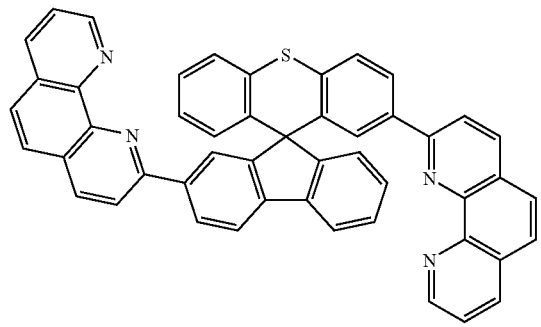

-continued
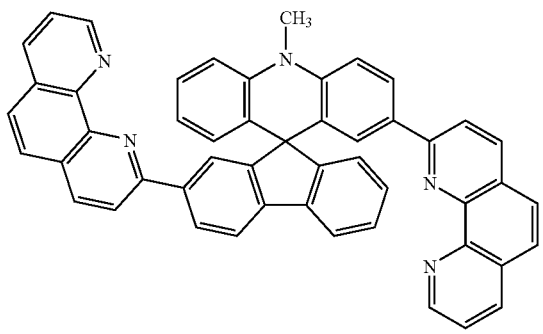
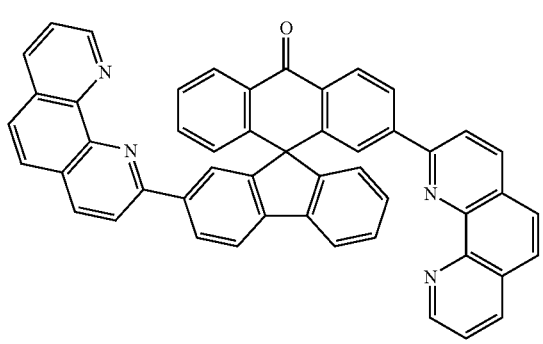
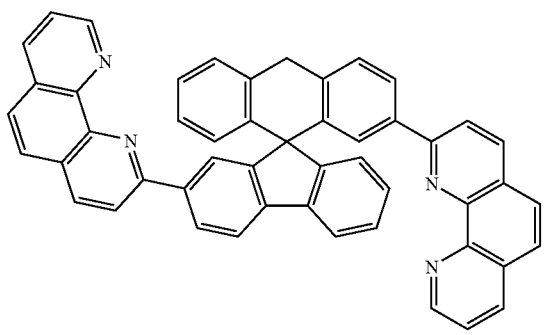
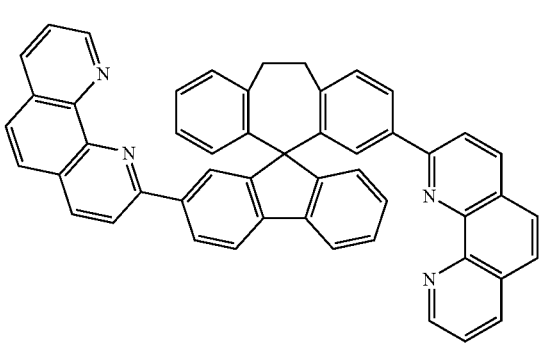
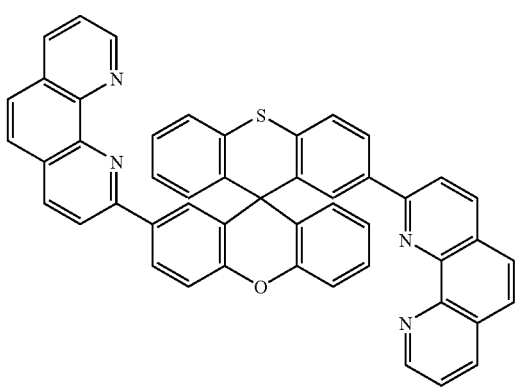
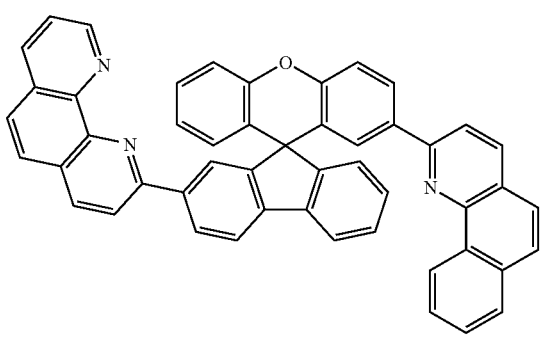
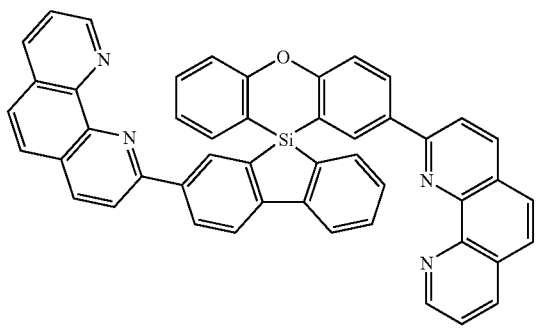
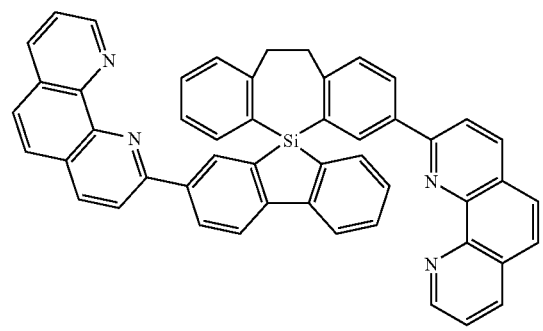
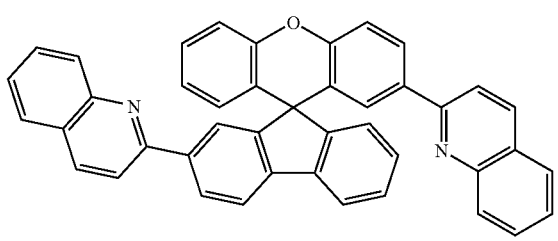
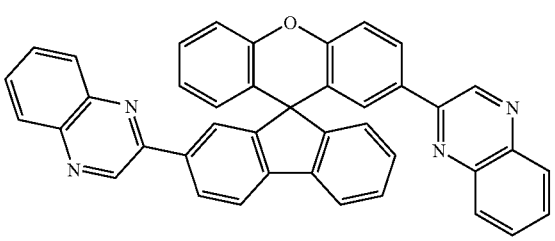

-continued
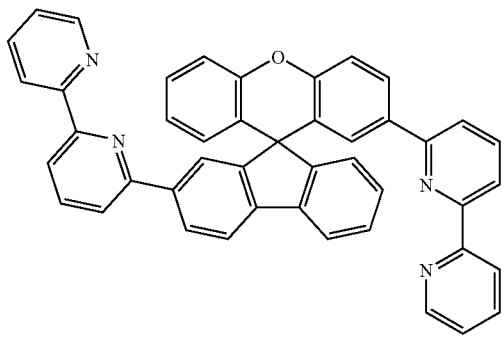
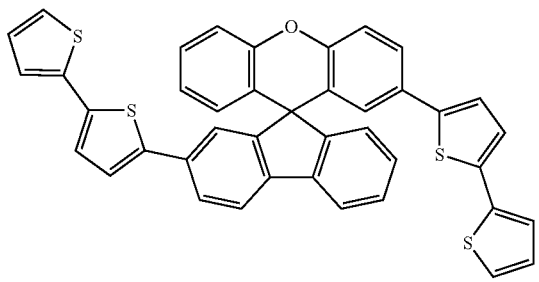
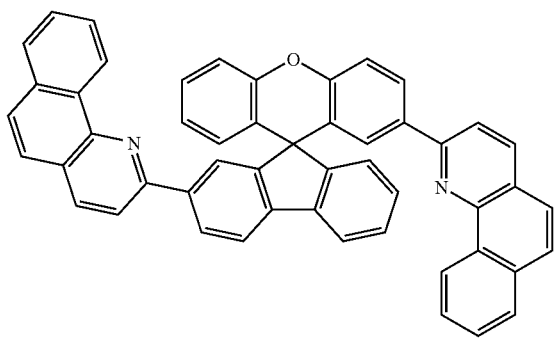
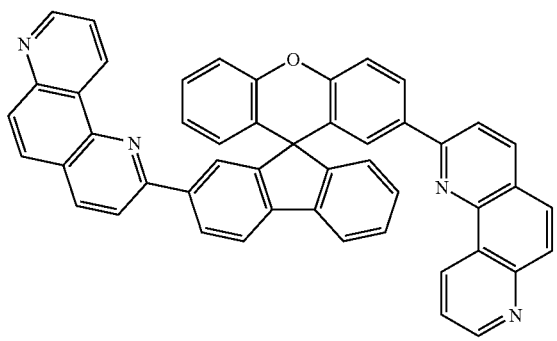
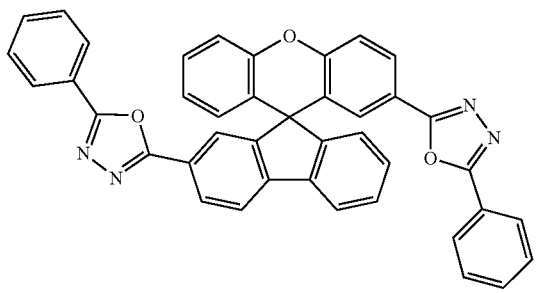
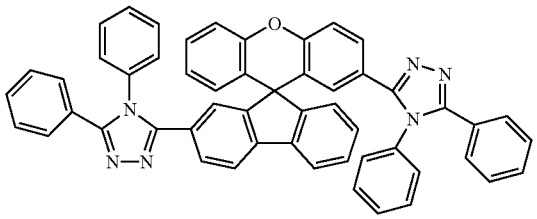
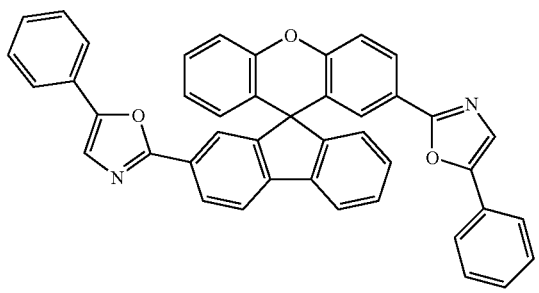
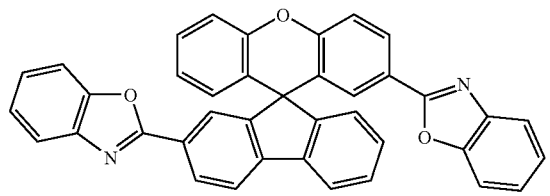
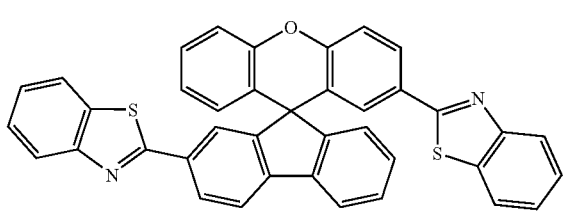
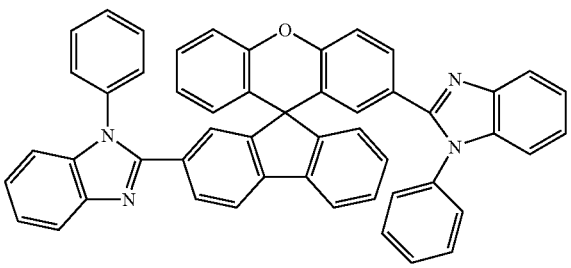

-continued
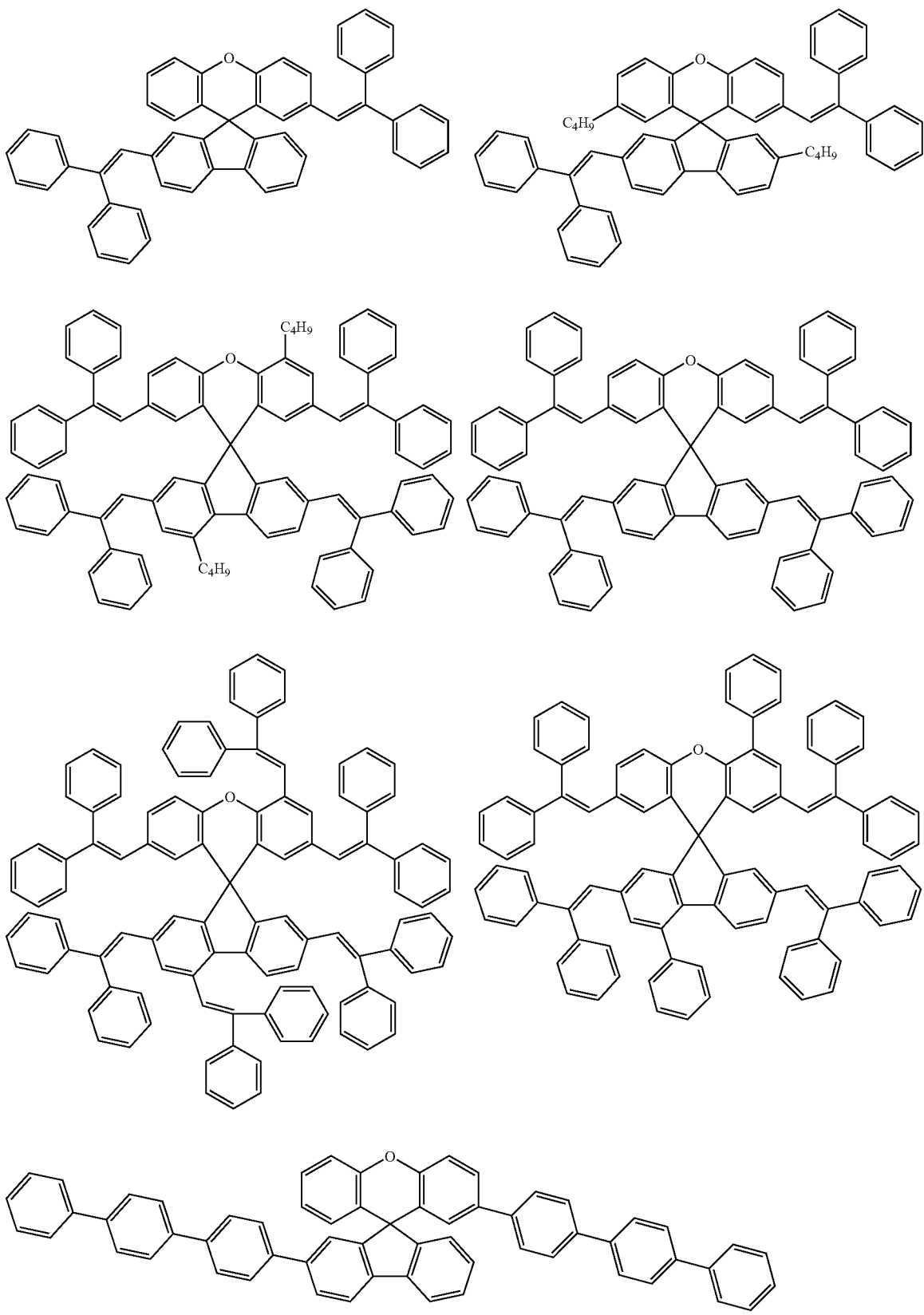

-continued

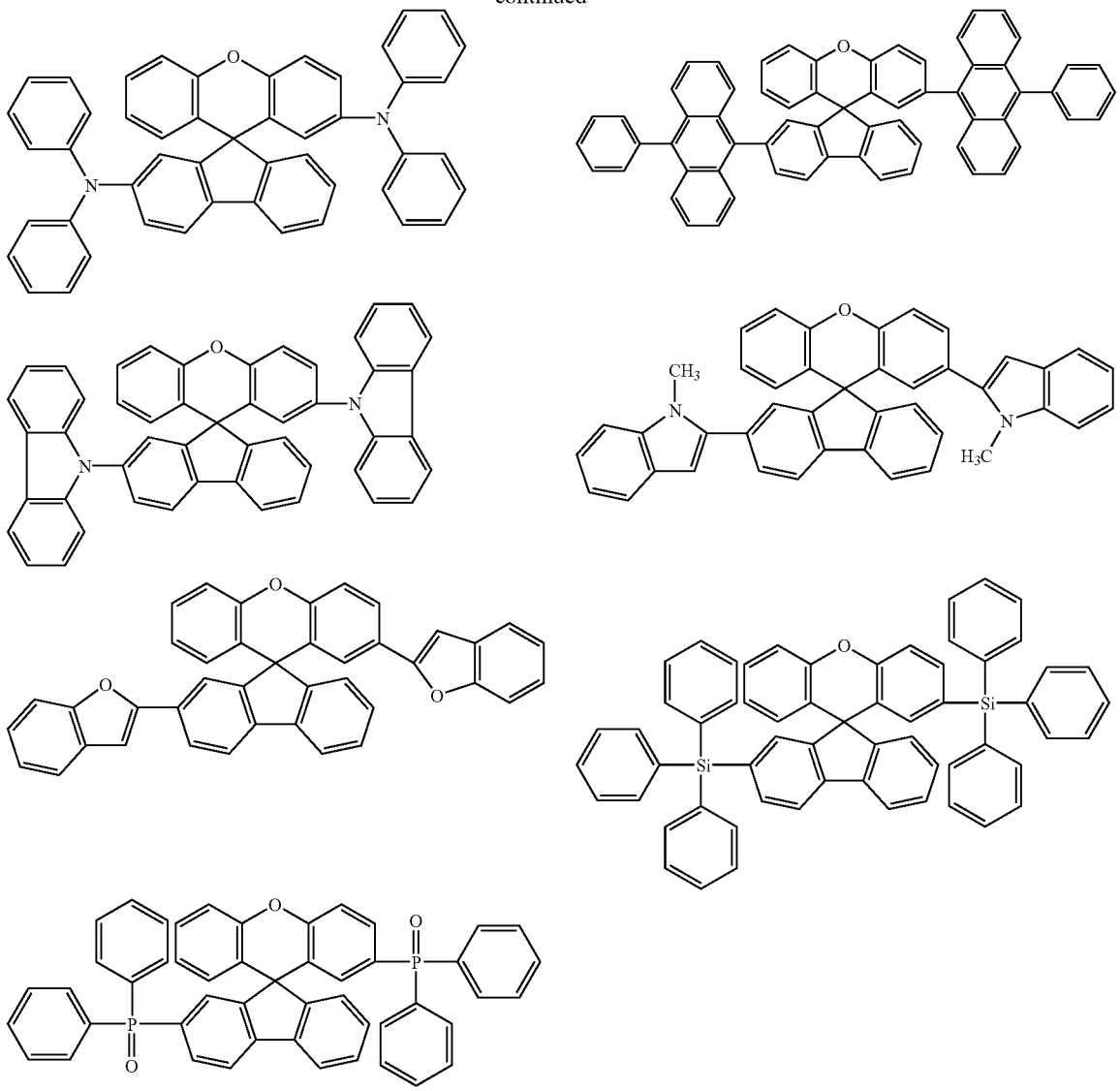

Explanation will now be provided of the synthesis of the sterically asymmetric central structure of the compounds represented by general formula (1), and of the introduction of functional substituents on the sterically asymmetric central structure.

The sterically asymmetric central structure represented by general formula (1) can be synthesized in the same way as the 9,9'-spirobifluorene. By using 9-xanthone instead of 9-fluorenone, the spiroxanthenefluorene can be obtained; by using 9-thioxanthone, spirothioxanthene-fluorene can be obtained; by using N-butyl-acridone, spiro-N-butyl-acridinefluorene can be obtained; by using anthrone, spirodihydroanthracenefluorene can be obtained; and by using suberone, spirodihydrodibenzo-cycloheptanefluorene can be obtained.

The introduction of a functional substituent on the sterically asymmetric central structure may be carried out directly but the method of firstly introducing a reactive substituent after which the functional substituent is introduced is preferred. Examples of reactive substituents are the formyl group, acetyl group, iodo group, bromo group, amino group, cyano group, nitro group, hydroxyl group, carboxylic acid or carboxylic acid derivative, and α-diketone group or the like. Below, examples of a number of reactive substituents are provided and the same techniques can be applied to other connecting units.

The introduction of an acetyl group, as described above, can be carried out by reaction between the sterically asymmetric central structure and acetyl chloride plus aluminium chloride at 50° C. in 1,2-dichloroethane and treating in the usual way. By varying the equivalent quantities of acetyl chloride and aluminium chloride, it is possible to introduce from one to four acetyl substituent groups.

The introduction of an iodo group, as described above, can be carried out by reaction between the sterically asymmetric central structure and iodine plus periodic acid dihydrate in 80% acetic acid at 80° C., and treating in the usual way, or by reaction with iodine and bis(trifluoroacetoxy)iodobenzene in carbon tetrachloride at 50-60° C., and treating in the usual way.

The introduction of a bromo group, as described above, can be carried out by reaction between the sterically asymmetric central structure and bromine at room temperature and treating in the usual way. By varying the equivalent quantity of the bromine, it is possible to introduce from one to four bromo substituent groups.

The introduction of other reactive substituent groups can be carried out in accordance with normal procedures.

With regard to the introduction of the functional substituents into the connecting unit following the introduction of the reactive substituents, for example starting from the acetyl group there can be introduced the phenanthroline group, benzoquinolyl group or indole group, etc; starting from the iodo group or bromo group, there can be introduced the pyridyl group, bipyridyl group, phenanthrolyl group, diphenylethylene group, polyphenylene group, n-butyl group, diphenylamino group or carbazolyl group, etc; starting from carboxylic acid or from a carboxylic acid derivative, there can be introduced heterocyclic groups such as azoles, benzazoles, diazoles and triazoles; and from α-diketone or amino groups there can be introduced quinoxaline and other such heterocylic groups. However, there are no particular restrictions thereto. Below, some examples are provided and the same kind of techniques can also be applied to other connecting units.

In the case of the introduction of a phenanthrolyl group, as stated above there is the method of reacting the sterically asymmetric central structure acetyl derivative with 8-amino-7-quinolinecarbaldehyde and potassium hydroxide in dioxane at 60° C. and treating in the usual way, or the method of converting the sterically asymmetric central structure iodo or bromo derivative to the lithio form with metal lithium, then reacting with the anhydrous phenanthroline and treating with water and manganese dioxide.

The introduction of the benzoquinolyl group, as stated above, can be carried out by reacting the sterically asymmetric central structure acetyl derivative with 1-amino-2-naphthalenecarbaldehyde and potassium hydroxide in dioxane at 60° C., and treating in the usual way.

As a literature reference on the introduction of the diphenylethylene group, there is SPIE, vol. 3797, page 317 "2.1 Synthesis EM1". Diphenylvinylboronic acid, sodium carbonate and tetrakis(triphenylphosphine)-palladium catalyst are added to the bromo derivative of the sterically asymmetric central structure, then reaction carried out at 100° C. in water/toluene, and treatment carried out in the usual manner. The introduction of polyphenylene can be carried out in the same way.

The introduction of the n-butyl group can be carried out by the reaction of the sterically asymmetric central structure bromo derivative and n-butyllithium at room temperature in THF, and treating in the usual way. At the time of the introduction of the aforesaid functional substituents starting from the bromo derivative of the connecting unit, any residual unreacted bromo groups can be treated and this is useful in terms of the thin film forming properties.

As a literature reference on the introduction of the indole group, there is the scheme on page 7312 of Tetrahedron Letters, vol. 40 (1999). The sterically asymmetric structure acetyl derivative and 1-methyl-1-phenylhydrazine are heated and refluxed in ethanol, then acetic acid added, followed by further heating/refluxing and treatment in the usual way, to obtain the hydrazine derivative, which is heated at 160° C. in polyphosphoric acid and treatment carried out in the usual way, so that introduction of the indole group is effected.

As a literature reference on the introduction of the diphenylamino group, there is SPIE, vol. 3797, page 317 "2.1 Synthesis HTM1". Diphenylamine, tert-butoxy sodium, 2,2'-bis(diphenylphosphino)-1,1'-binaphthyl and palladium acetate are added to the bromo derivative of the sterically asymmetric structure, then heating and refluxing carried out in toluene and treatment performed in the usual way, so that introduction of the diphenylamino group is effected. The introduction of a carbazolyl group can be carried out in the same way.

Explanation is now provided relating to the tetraphenylmethane derivative represented by general formula (2) in the present invention.

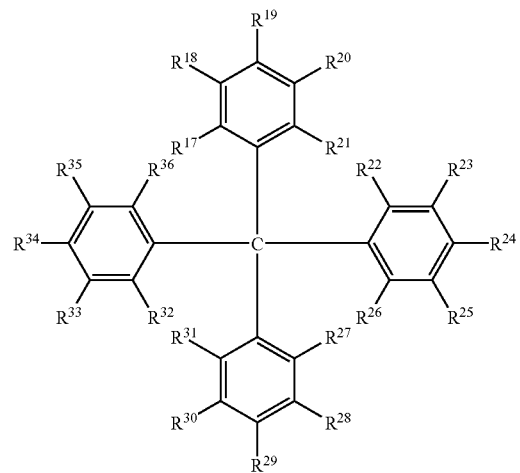

(2)

$R^{17}$ to $R^{36}$ are each selected from hydrogen, alkyl group, cycloalkyl group, aralkyl group, alkenyl group, cycloalkenyl group, alkynyl group, hydroxyl group, mercapto group, alkoxy group, alkylthio group, aryl ether group, aryl thioether group, aryl group, heterocyclic group, halogen, haloalkane, haloalkene, haloalkyne, cyano group, aldehyde group, carbonyl group, carboxyl group, ester group, carbamoyl group, amino group, nitro group, silyl group, siloxanyl group and a cyclic structure formed with an adjacent substituent. However, at least one of $R^{17}$ to $R^{36}$ is selected from substituents represented by general formula (3).

—X—Ar  (3)

X is either a single bond or is selected from the following. Ar denotes a condensed aromatic ring or heteroaromatic ring. However, in the case where X is phosphorus oxide, then Ar represents an aromatic hydrocarbon or heteroaromatic ring.

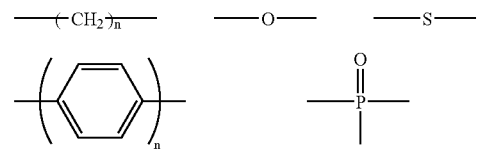

n denotes an natural number.

The explanation of these substituents is the same as for the compounds of general formula (1) above. Examples of the condensed rings in general formula (3) are naphthalene, anthracene, phenanthrene and pyrene, and these may be unsubstituted or substituted. Examples of the heteroaromatic rings are furan, pyrrole, thiophene, thiophene dioxide, pyrazole, imidazole, triazole, tetrazole, oxazole, oxadiazole, thiazole, thiadiazole, pyridine, pyridazine, pyrimidine, pyrimidone, pyrazine, triazine, and those formed by ring fusion with the above such as benzofuran, dibenzofuran, indole, carbazole, benzothiophene, benzothiophene dioxide, dibenzothiophene, benzimidazole, phenanthroimidazole, benzoxazole, benzothiazole, quinoline, benzoquinoline, quinoxaline, quinazoline, naphthyridine, phenanthridine, phenanthroline, imidazopyridine, phenazine and the like, and these may be unsubstituted or substituted.

Depending on the type of such substituents, it is possible to used the tetraphenylmethane derivatives of the present invention in the various layers of the light emitting device.

The number of substituents represented by general formula (3) is not particularly restricted but from one to four is preferred, with two or four further preferred. In the case of one, the functionality of the substituent may not readily be manifested, while synthesis and purification may be difficult in the case of three substituents.

The position of a substituent group represented by general formula (3) is not particularly restricted but, from the point of view of ease of synthesis, $R^{18}$, $R^{19}$, $R^{20}$, $R^{23}$, $R^{24}$, $R^{25}$, $R^{28}$, $R^{29}$, $R^{30}$, $R^{33}$, $R^{34}$ and $R^{35}$ are preferred, and from the point of view of heat resistance $R^{19}$, $R^{24}$, $R^{29}$ and $R^{34}$ are still further preferred.

Examples of literature references on the synthesis of the tetraphenylmethane skeletal structure are Angew. Chem. Int. Ed. Eng. vol. 25 (1986) No. 12, page 1098, and Tetrahedron Letters, vol. 38 (1997) page 1487. Triphenylmethanol or triphenylmethyl chloride is reacted with aniline or aniline hydrochloride at 100-220° C. in the absence of solvent or in acetic acid solvent, and the intermediate obtained treated in the usual way and isolated, after which reaction is effected with isoamyl nitrite at −10° C. in an ethanol/sulphuric acid mixed solvent, then phosphinic acid added and heating and refluxing performed, and treatment carried out in the usual way.

With regard to the substituents of general formula (3), these can be introduced onto the tetraphenylmethane structure by identical methods to the methods used above for the introduction of functional substituents into spiro compounds.

The following structures may be given as examples of the aforesaid tetraphenylmethane derivatives.

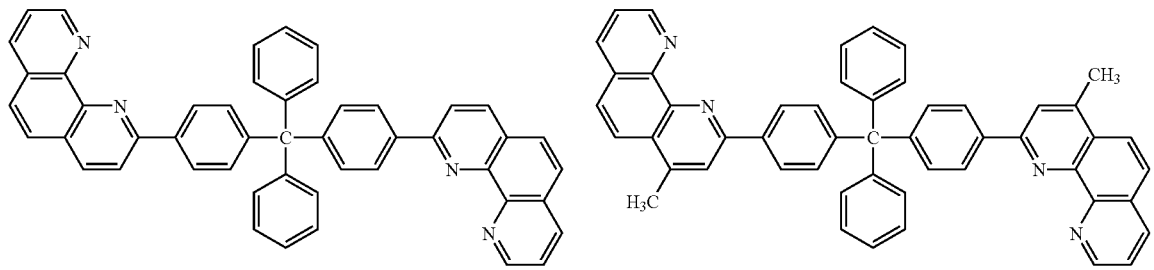

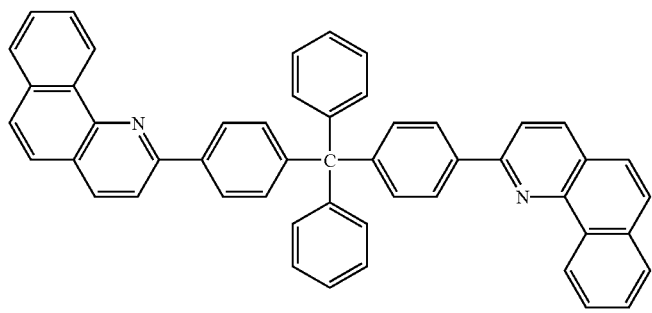

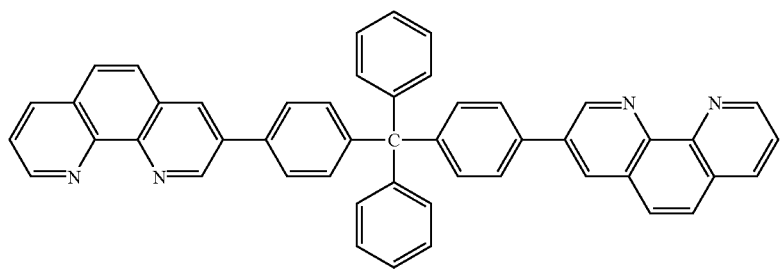

-continued
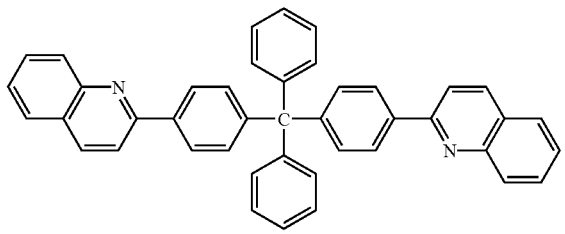
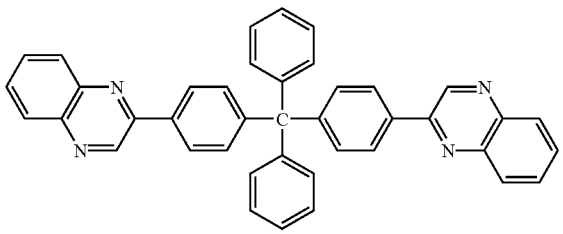
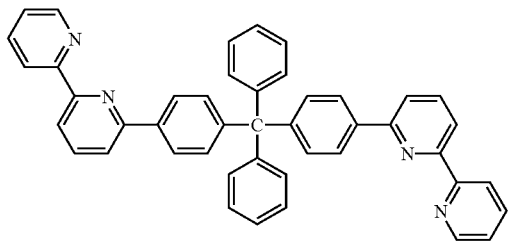
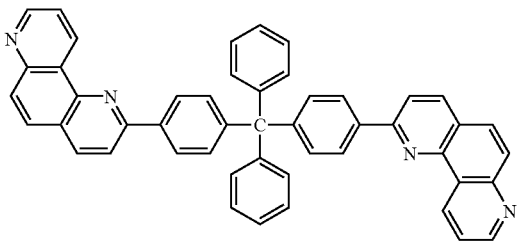
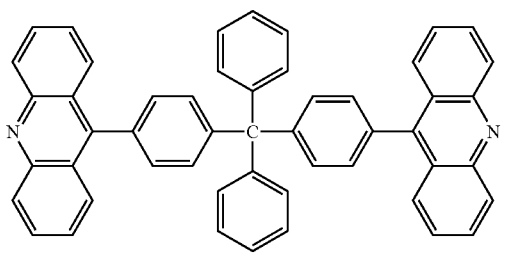
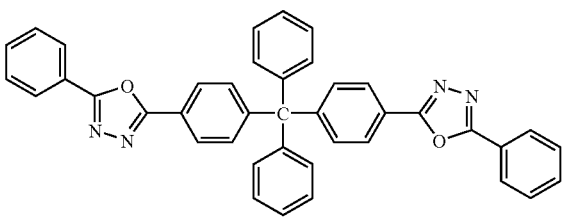
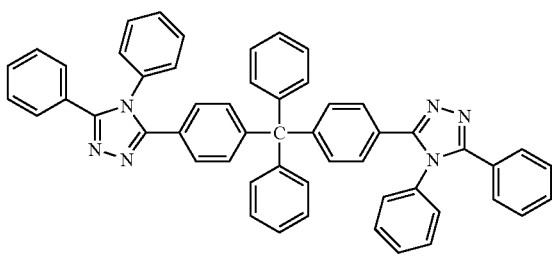
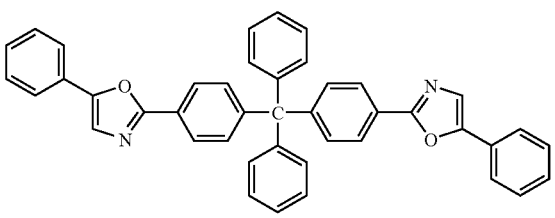
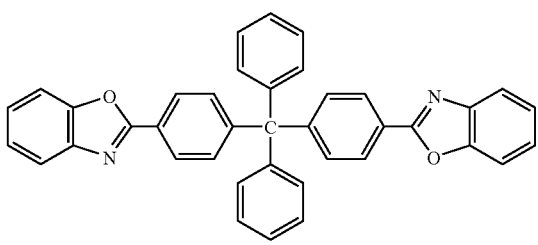
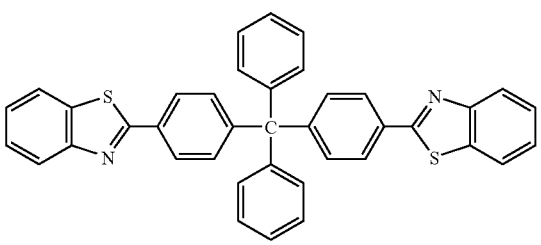
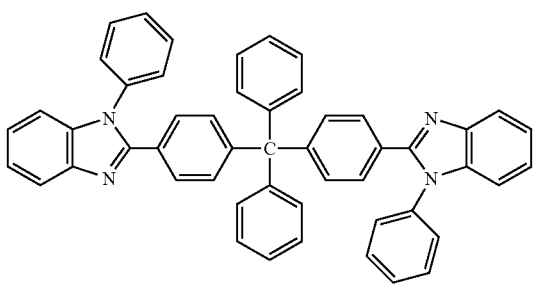
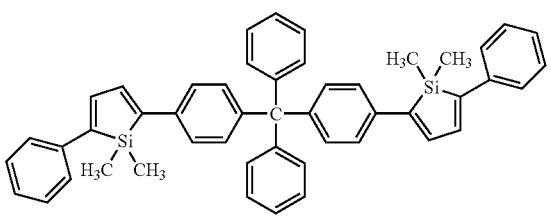

-continued
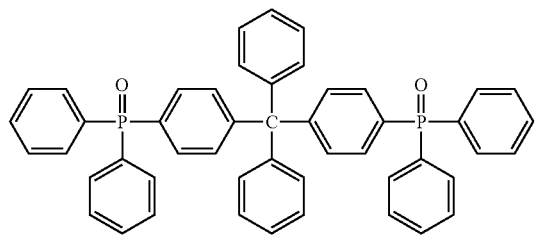
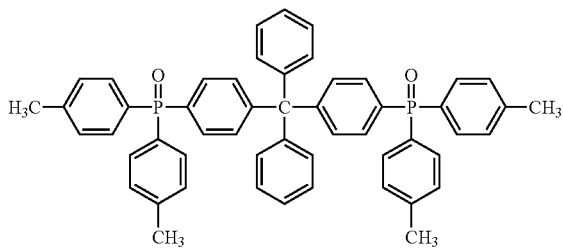
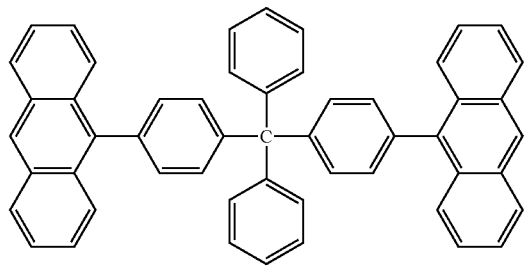
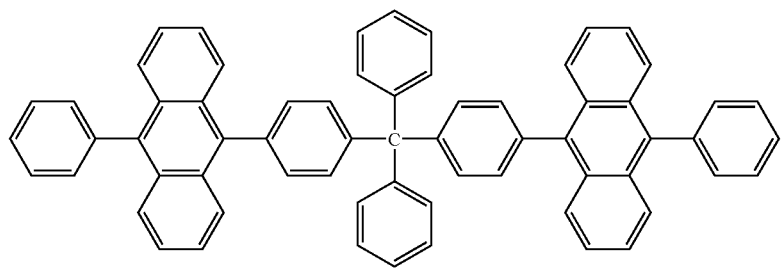
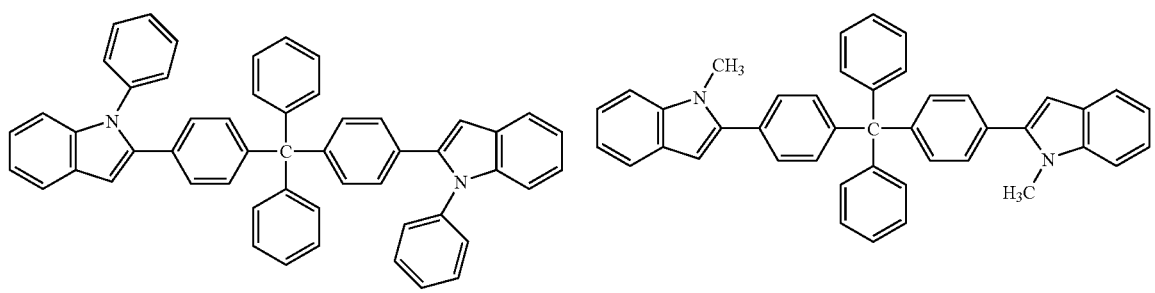
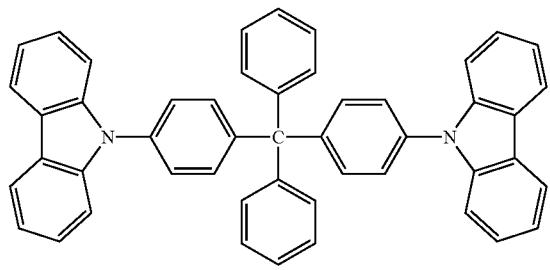

-continued
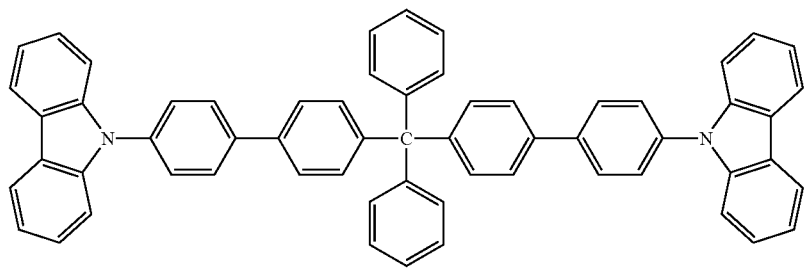
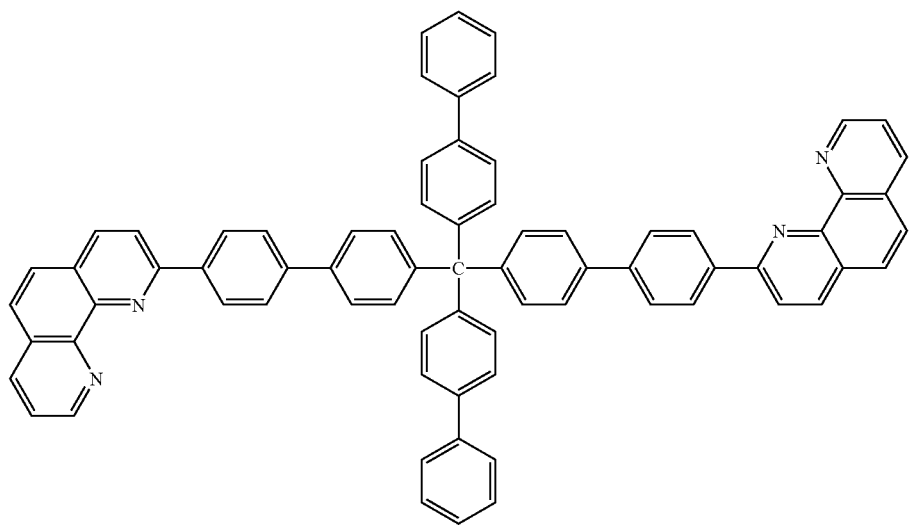
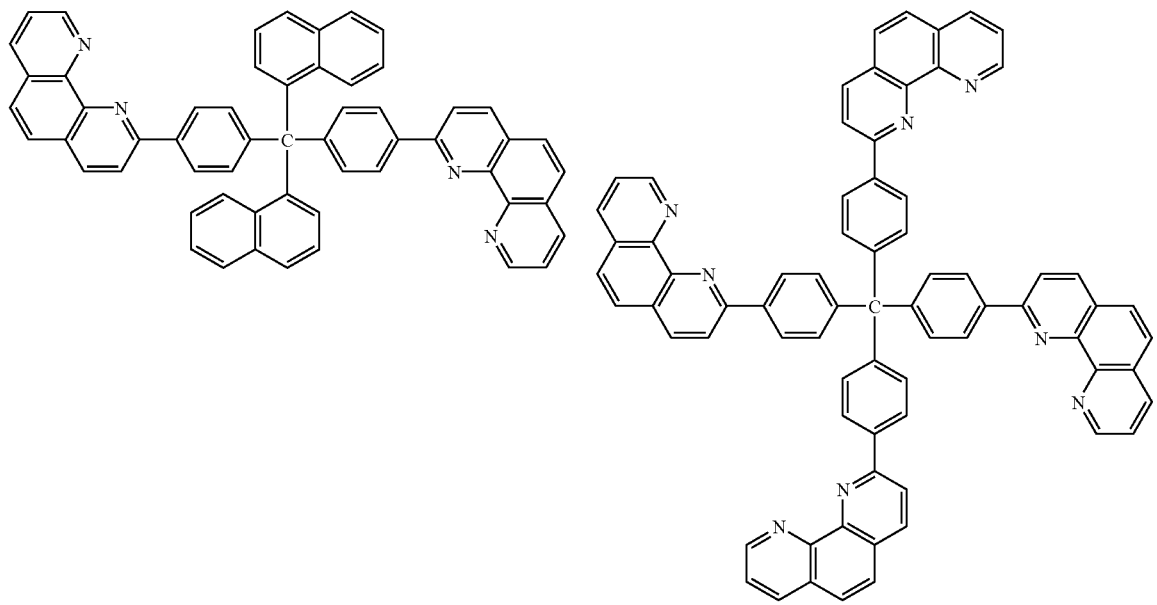

-continued

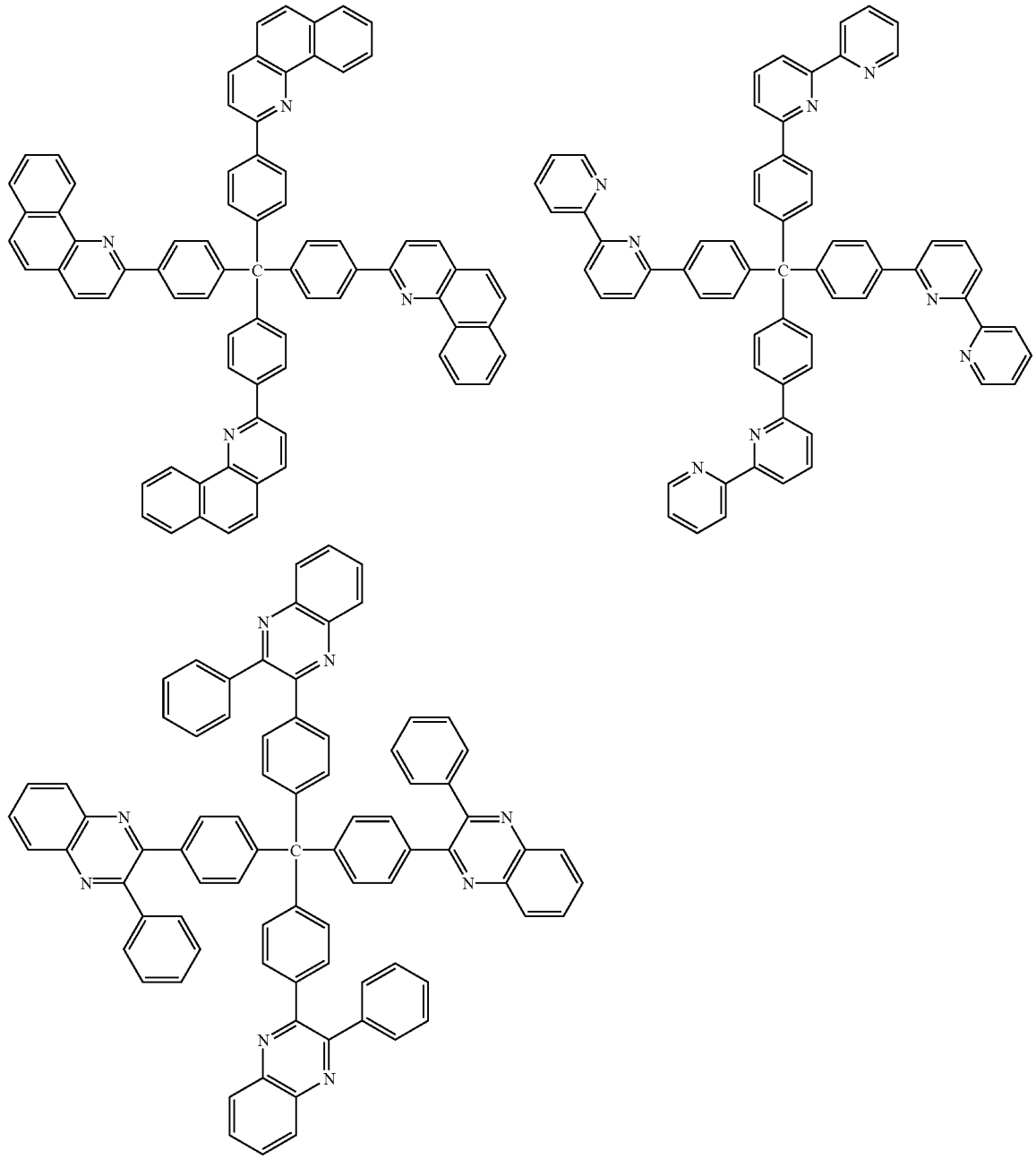

Examples of methods for forming the respective layers are evaporation by resistance heating, electron beam evaporation, sputtering, molecular deposition, coating and the like. Normally, evaporation by resistance heating and electron beam evaporation are preferred in terms of properties. Layer thickness will depend on the resistance of the emissive substance, so cannot be restricted but will be selected from within the range 1 to 1,000 nm.

Reference to electrical energy primarily means direct current but it is also possible to use a pulse current or alternating current. The values of the current and voltage are not particularly restricted but, taking into account power consumption and the life of the device, the maximum luminance should be obtained at as low energy as possible.

Reference to matrix in the present invention means the matrix array of pixels used for display, and by association of pixels the display of characters or images is effected. The shape and size of the pixels is determined by the application. In the case of image and character display by personal computers, monitors and televisions, there are normally used square-shaped pixels with up to 300 µm sides, and in the case of large-size displays such as display panels there are normally used pixels with sides of the mm order. In the case of a monochrome display, there may be arrayed pixels of the same colour but, in the case of a colour display, red, green and blue pixels are arranged side by side. In such circumstances, typically there are delta and stripe types. The method of driving the matrix may be either the active matrix or passive matrix driving method. Construction is simpler in the case of passive matrix driving, while an active matrix may be superior in operational characteristics, so here too selection will be made according to the application.

Segment type in the present invention means that a pattern is formed so as to display previously-determined data, and there is emission in a predetermined region. Examples include time and temperature displays by digital watches and thermometers, operating-state displays in the case of audio equipment and microwave ovens, vehicle panel displays and the like. Now, the aforesaid matrix and segment displays may also both be present in the same panel.

The light emitting device of the present invention can also be favourably employed as a back light. A back light is primarily used for the purposes of enhancing the visibility of a display means which is not self-illuminating, and it may be employed for liquid crystal display devices, watches, audio equipment, automobile panels, signboards, signs and the like. In particular, liquid crystal display devices and, especially, conventional personal computers, have comprised fluorescent bulbs or light-guiding sheets, so making these thinner has been difficult. However, thin, lightweight, products are possible with backlights employing the light emitting device of the present invention.

Below, the present invention is explained by providing examples and comparative examples but the present invention is not to be restricted by these examples. The conditions employed and the results obtained are shown together in Table 1 and Table 2 at the end of this section.

EXAMPLE 1

Synthesis of Connecting Unit 1

14.8 g of 2-bromobiphenyl was converted to the Grignard form in THF using 2.2 g of metal magnesium, then this reacted with 12.3 g of 9-xanthone at from room temperature to 50° C. and, by treatment in the normal way, 9-(2-biphenyl)-9-xanthenol was obtained. This was heated in acetic acid to which a small amount of hydrochloric acid had been added, so that water was eliminated and, by treatment in the usual way, Connecting Unit 1 (8.5 g) shown below was obtained. $^1$H-NMR (CDCl$_3$, ppm): 7.8 (d, 2H), 7.2 (t, 2H), 7.2 (m, 8H), 6.8 (t, 2H), 6.4 (d, 2H)

Connecting Unit 1

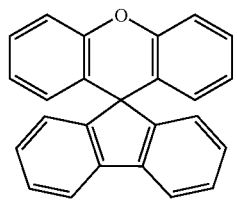

EXAMPLE 2

Synthesis of Connecting Unit 2

11.9 g of 2-bromobiphenyl was converted to the Grignard form in THF using 1.7 g of metal magnesium, then this reacted with 13.4 g of 2,4-diethyl-9-thioxanthone at from room temperature to 50° C. and, by treatment in the normal way, 2,4-diethyl-9-(2-biphenyl)-9-thioxanthenol was obtained. This was heated in acetic acid to which a small amount of hydrochloric acid had been added, so that water was eliminated and, by treatment in the usual way, Connecting Unit 2 (13.8 g) shown below was obtained. $^1$H-NMR (CDCl$_3$, ppm): 7.8 (m, 2H), 7.6 (d, 2H), 7.4 (m, 3H), 7.2 (m, 2H), 7.1 (t, 1H), 6.9 (s, 1H), 6.8 (t, 1H), 6.5 (d, 1H), 6.2 (s, 1H), 2.9 (m, 2H), 2.3 (m, 2H) 1.4 (t, 3H), 0.9 (t, 3H)

Connecting Unit 2

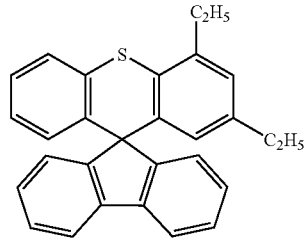

EXAMPLE 3

Introduction of Acetyl Groups into Connecting Unit 1: Connecting Unit 1'

Connecting Unit 1 (8.5 g) was reacted with 4.5 g of acetyl chloride and 7.5 g of aluminium chloride at 50° C. in 1,2-dichloroethane and, by treatment in the normal way, Connecting Unit 1' (13.1 g) shown below was obtained. $^1$H-NMR (CDCl$_3$, ppm): 8.0 (d, 1H), 7.9 (d, 2H), 7.8 (d, 1H), 7.7 (s, 1H), 7.4 (t, 1H), 7.3–7.1 (m, 5H), 7.0 (s, 1H), 6.8 (t, 1H) 6.3 (d, 1H), 2.5 (s, 3H), 2.3 (s, 3H)

Connecting Unit 1'

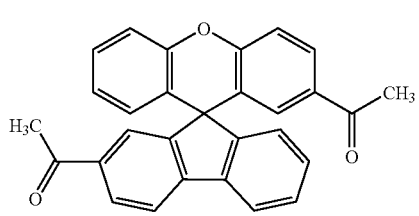

EXAMPLE 4

Synthesis of the Benzoquinoline Derivative (BQ-1)

23.8 g of 2-bromobiphenyl was converted to the Grignard form in THF using 3.4 g of metal magnesium, then this reacted with 18.0 g of 9-fluorenone at from room temperature to 50° C. and, by treatment in the normal way, 9-(2-biphenyl)-9-fluorenol was obtained. This was heated in acetic acid to which a small amount of hydrochloric acid had been added, so that water was eliminated and, by treatment in the usual way, 9,9'-spirobifluorene (18.5 g) was obtained. Next, Connecting Unit 1 (15.8 g) was reacted with 8.6 g of acetyl chloride and 14.7 g of aluminium chloride at 50° C. in 1,2-dichloroethane and, by treatment in the normal way, 2,2'-diacetyl-9,9'-spirobifluorene (11.2 g) was obtained. This diacetyl compound (2.3 g) was reacted with 2.0 g of 1-amino-2-naphthalenecarbaldehyde and 1.6 g of potassium hydroxide at 60° C. in dioxane and, by treatment in the normal way, there was obtained BQ-1 (1.5 g) shown below.

¹H-NMR (CDCl₃, ppm): 9.4 (d, 2H), 8.6 (d.d, 2H), 8.1 (d, 2H), 8.0 (t, 4H), 7.8 (d, 2H), 7.8-7.6 (m, 12H), 7.4 (t, 2H), 7.2 (t, 2H), 6.8 (d, 2H).

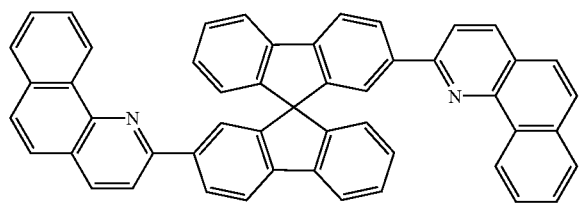

BQ-1

EXAMPLE 5

Synthesis of Benzoquinoline Derivatives (BQ-2 and 3)

Reaction was carried out in the same way as in Example 4 using the tetra-acetyl derivative, and treatment was carried out in the normal way so that BQ-2 and BQ-3 shown below were obtained.

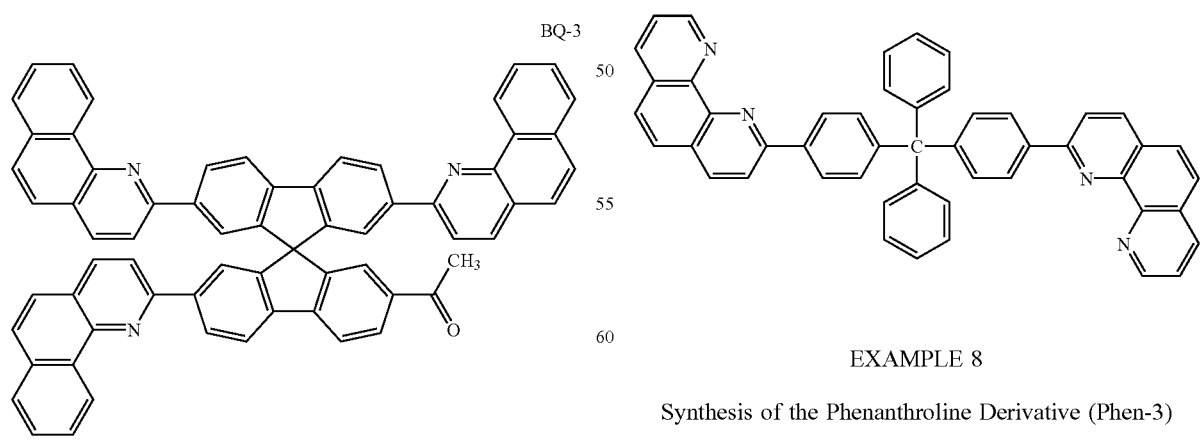

BQ-2

BQ-2: ¹H-NMR (CDCl₃, ppm) 9.39 (d, 4H), 8.72 (d, 4H), 8.27 (d, 4H), 8.03 (d, 4H), 7.84–7.55 (m, 24H), 7.32 (d·d·d, 4H)

BQ-3

BQ-3: ¹H-NMR (CDCl₃, ppm) 9.36 (d, 3H), 8.72 (d·d, 1H), 8.66 (d·d, 2H), 8.24 (d,1H), 8.23 (d, 2H), 8.12–8.03 (m, 6H), 7.87–7.49 (m, 21H), 2.46 (s, 3H)

EXAMPLE 6

Synthesis of the Phenanthroline Derivative (Phen-1)

Connecting Unit 1' (5.0 g) was reacted with 5.2 g of 8-amino-7-quinolinecarbaldehyde and 5.0 g of potassium hydroxide at 60° C. in dioxane and, by treatment in the normal way, Phen-1 (5.8 g) shown below was obtained. ¹H-NMR (CDCl₃, ppm): 9.2 (d, 2H), 8.8 (d, 1H), 8.5 (d, 1H), 8.2 (m, 3H), 8.1 (t, 2H), 7.9 (t, 2H), 7.7–7.5 (m, 8H), 7.4 (m, 1H), 7.3–7.2 (m, 5H), 7.1 (s, 1H), 6.8 (t, 1H), 6.5 (d, 1H)

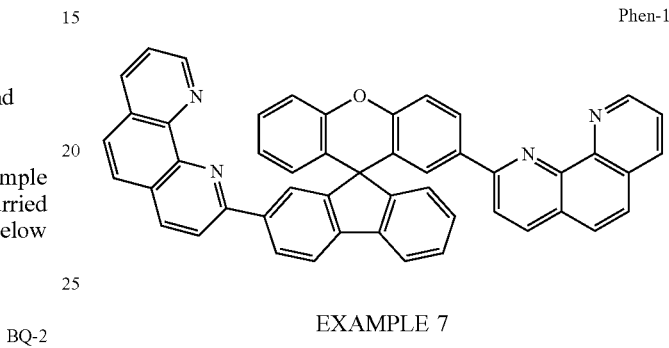

Phen-1

EXAMPLE 7

Synthesis of Phenanthroline Derivative (Phen-2)

2.5 g of tetraphenylmethane, 2.08 g of aluminium chloride and 1.22 ml of acetyl chloride were added to 100 ml of 1,2-dichloroethane, and reaction carried out for 1.5 hours at room temperature and then for 2 hours at 70° C. By treatment in the normal way, 1.03 g of the diacetyltetraphenylmethane was obtained. ¹H-NMR (CDCl₃, ppm): 7.86 (d, 4H), 7.35 (d, 4H), 7.24 (m, 10H)

1.0 g of the aforesaid diacetyltetraphenylmethane was reacted with 1.06 g of 8-amino-7-quinolinecarbaldehyde and 1.0 g of potassium hydroxide in dioxane at 60° C. and, by treatment in the normal way, Phen-2 (1.21 g) shown below was obtained. ¹H-NMR (CDCl₃, ppm): 9.21 (d·d, 2H), 8.31–8.19 (m, 8H), 8.07 (d, 2H), 7.76 (q, 4H), 7.62 (d·d, 2H), 7.50 (d, 4H), 7.39–7.20 (m, 10H)

Phen-2

EXAMPLE 8

Synthesis of the Phenanthroline Derivative (Phen-3)

2.5 g of 2,2'-dibromobiphenyl, 3.9 g of 3-acetylphenylboronic acid, 21 ml of 2M sodium carbonate and 0.37 g of tetrakis(triphenylphosphine)palladium(0) were added to 200 ml of 1,2-dimethoxyethane, and refluxing carried out for 10 hours under nitrogen so that a Suzuki coupling reaction was performed and, by treatment in the normal way, 0.57 g of 2,2'-bis(3-acetylphenyl)biphenyl was obtained. 0.57 g of this diacetyl derivative was reacted with 0.63 g of 8-amino-7-quinolinecarbaldehyde and 0.6 g of potassium hydroxide in dioxane at 60° C. and, by treatment in the normal way, Phen-3 (0.76 g) shown below was obtained. $^1$H-NMR (CDCl$_3$, ppm) 9.20 (d·d, 2H), 8.43 (d, 2H), 8.16 (d·d, 2H), 7.79 (d, 2H), 7.61–7.26 (m, 18H), 7.17 (t, 2H), 6.77 (d, 2H)

Phen-3

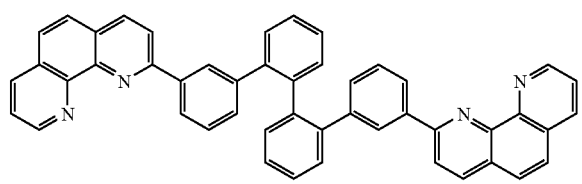

EXAMPLE 9

Synthesis of the Phenanthroline Derivative (Phen-4)

2.5 g of 6,6'-bis(trifluoromethanesulphonyloxy)-3,3,3',3'-tetramethyl-1,1'-spirobiindane, 2.2 g of 4-acetylphenylboronic acid, 12 ml of 2M sodium carbonate and 0.40 g of tetrakis(triphenylphosphine)palladium(0) were added to a solvent mixture of 50 ml of toluene and 30 ml of ethanol, and then refluxing carried out for 12 hours under nitrogen so that a Suzuki coupling reaction was conducted and, by treatment in the normal way, 1.5 g of 6,6'-bis(4-acetylphenyl)-3,3,3',3'-tetramethyl-1,1'-spirobiindane was obtained. 1.50 g of this diacetyl derivative was reacted with 1.26 g of 8-amino-7-quinolinecarbaldehyde and 0.9 g of potassium hydroxide in dioxane at 60° C. and, by treatment in the normal way, Phen-4 (1.40 g) shown below was obtained. $^1$H-NMR (CDCl$_3$, ppm): 9.21 (d, 2H), 8.35 (d, 4H), 8.25 (t, 4H), 8.09 (d, 2H), 7.80–7.59 (m, 12H), 7.34 (d, 2H), 7.24 (d, 2H), 2.46 (d, 4H), 1.52 (s, 6H), 1.46 (s, 6H)

EXAMPLE 10

Synthesis of the Phenanthroline Derivative (Phen-5)

4.0 g of propellane, 3.3 g of aluminium chloride and 2.0 ml of acetyl chloride were added to 200 ml of 1,2-dichloroethane, and reaction carried out for 1.5 hours at room temperature and then for 6 hours at 60° C. By treatment in the normal way, 3.26 g of the triacetyl-propellane was obtained. 1.41 g of this triacetyl derivative was reacted with 1.50 g of 8-amino-7-quinolinecarbaldehyde and 1.5 g of potassium hydroxide in dioxane at 60° C. and, by treatment in the normal way, Phen-5 (1.32 g) shown below was obtained.

Phen-5

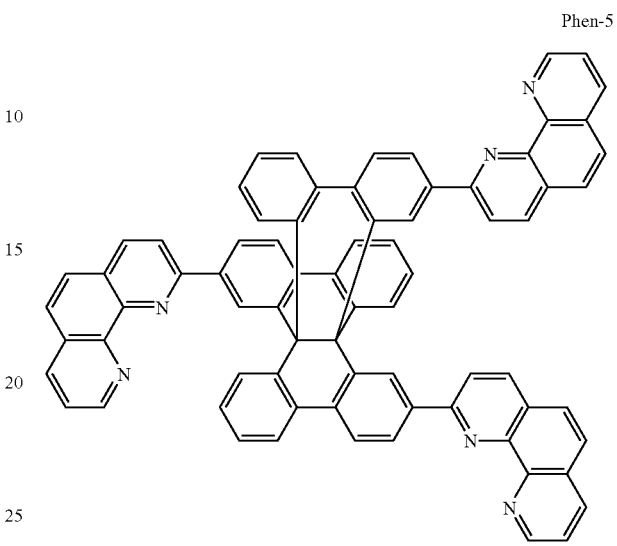

EXAMPLE 11

Synthesis of the Phenanthroline Derivative (Phen-6)

1.52 g of 2,2'-diacetyl-9,9'-spirobifluorene was reacted with 1.31 g of 5-amino-6-quinolinecarbaldehyde and 1.0 g of potassium hydroxide in dioxane at 60° C. and, by treatment in the normal way, Phen-6 (0.29 g) shown below was obtained. $^1$H-NMR (CDCl$_3$, ppm): 9.557 (d, 2H), 8.99 (d·d, 2H), 8.57 (d·d, 2H), 8.11 (d·d, 4H), 7.98 (t, 4H), 7.84 (d, 2H), 7.81 (d, 2H), 7.61–7.56 (m, 4H), 7.45 (t, 2H), 7.18 (t, 2H), 6.84 (d, 2H)

Phen-4

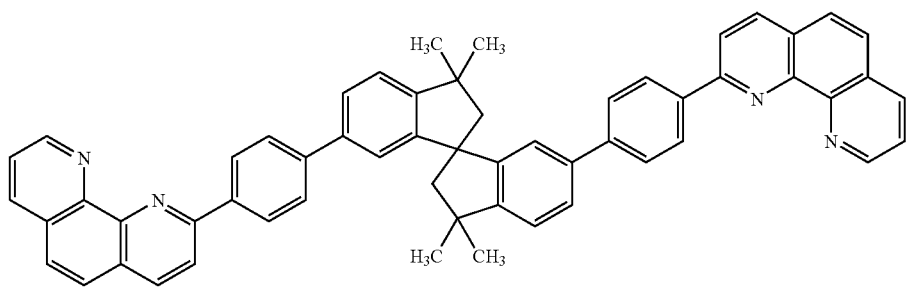

Phen-6

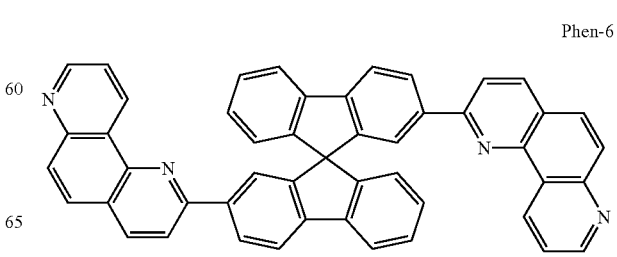

EXAMPLE 12

Synthesis of the Naphthyridine Derivative (TPM-dNTR)

0.77 g of diacetyltetraphenylmethane obtained by the method described in Example 7 was reacted with 0.51 g of 2-aminonicotinaldehyde and 0.76 g of potassium hydroxide in dioxane and, by treatment in the normal way, TPM-dNTR (0.82 g) shown below was obtained. $^1$H-NMR (CDCl$_3$, ppm): 9.12 (d·d, 2H), 8.27–8.16 (m, 8H), 8.00 (d, 2H), 7.49–7.44 (m, 6H), 7.34–7.23 (m, 10H)

TPM-dNTR

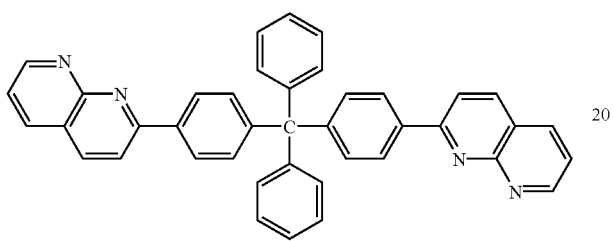

EXAMPLE 13

A glass substrate on which a 150 nm ITO transparent electroconductive film had been deposited (produced by the Asahi Glass Co., 15 Ω/□, electron beam vapour-deposited product) was cut to 30×40 mm and etching carried out. The substrate obtained was subjected to ultrasonic washing for 15 minute periods with acetone and "Semico-Clean 56" respectively, after which washing was carried out with ultra-pure water. Next, 15 minutes ultrasonic washing was performed with isopropyl alcohol, after which it was immersed for 15 minutes in hot methanol and dried. Just prior to producing the device, this substrate was given a 1 hour UV/ozone treatment, then placed in vacuum vapour-deposition equipment and the equipment evacuated until the degree of vacuum inside was less than 1×10$^{-5}$ Pa. By means of a resistance heating method, firstly there was deposited 10 nm of copper phthalocyanine (CuPc) as a first hole injecting and transporting layer, and then there was provided a 50 nm layer of N,N'-diphenyl-N,N'-bis(1-naphthyl)-1,1'-diphenyl-4,4'-diamine (α-NPD) as a second hole transporting layer. Furthermore, next there was codeposited to a thickness of 25 nm the emissive layer region using tris(8-quinolinolato) aluminium (III) (Alq3) as the host material and 2,3,5,6-tetrahydro-9-(2-benzothiazolyl)-quinolizino-[9,9a,1-gh] coumarin (Coumarin-1) as the dopant material, such that there was 1.0 wt % of the dopant. Thereafter, ETM1 shown below was deposited at a thickness of 25 nm as the electron transporting layer. Next, 0.2 nm lithium doping was performed, and finally there was vapour-deposited 150 nm of aluminium to produce the cathode and, in this way, a 5×5 mm square device was produced. The ionization potential of the electron transporting layer was 6.07 eV, the molecular weight was 672, the glass transition temperature was 219° C. and the cold crystallization temperature was 352° C. The ionization potential of the emissive layer was 5.78 eV and so the difference in the ionization potential compared to the emissive layer was 0.29 eV. At a driving voltage of 10 V, from this light emitting device there was obtained green coloured light emission based on the dopant material of peak emission wavelength 523 nm, and the luminance was 38,000 cd/m$^2$. Furthermore, after the elapse of 500 hours operation of this light emitting device, the percentage retention of the initial luminance was 80% and a uniform emissive surface was maintained.

ETM1

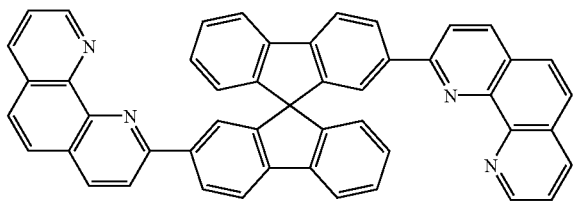

COMPARATIVE EXAMPLE 1

A light emitting device was constructed in exactly the same way as in Example 13 except that there was used Alq3 as the electron transporting layer. The ionization potential of Alq3 is 5.79, its molecular weight is 459 and its glass transition temperature is 180° C. From this light emitting device, at a driving voltage of 10 V there was obtained green coloured light emission based on the dopant material of peak emission wavelength 523 nm, and the luminance was 6000 cd/m$^2$.

COMPARATIVE EXAMPLE 2

A light emitting device was constructed in exactly the same way as in Example 13 except that there was used 2,9-dimethyl-4,7-diphenyl-1,10-phenanthroline (BCP) as the electron transporting layer. The ionization potential of BCP is 6.2 eV, its molecular weight is 360 and its crystallization temperature is 77° C. From this light emitting device, at a driving voltage of 10 V there was obtained green coloured light emission based on the dopant material of peak emission wavelength 523 nm, and the luminance was 12,000 cd/m$^2$. However, after the elapse of 500 hours operation of this light emitting device, the percentage retention of the initial luminance was less than 50% and unevenness was apparent at the emissive surface.

EXAMPLE 14

A light emitting device was constructed in exactly the same way as in Example 13 except that there was deposited, as the emissive layer region, a 20 nm thickness of a mixture of 4,4'-bis(N-carbazolyl)biphenyl (CBP) and tris(2-phenylpyridine)iridium complex (Ir(ppy)3) [iridium complex content =8 wt %]. At a driving voltage of 6 V, from this light emitting device there was obtained green coloured light emission based on the iridium complex of peak emission wavelength 515 nm, and the luminance was 1000 cd/m$^2$. Thus, the electron transporting material of the present invention also functioned effectively in a device employing a phosphorescent material as an emissive material.

EXAMPLE 15

A light emitting device was constructed in exactly the same way as in Example 13 except that there was used EM1, which is shown below, as the emissive material. At a driving voltage of 15 V, from this light emitting device there was obtained blue coloured light emission based on the EM1 of peak emission wavelength 463 nm, and the luminance was 8,000 cd/m$^2$. Thus, the electron transporting material of the present invention also functioned effectively in a blue coloured light emitting device.

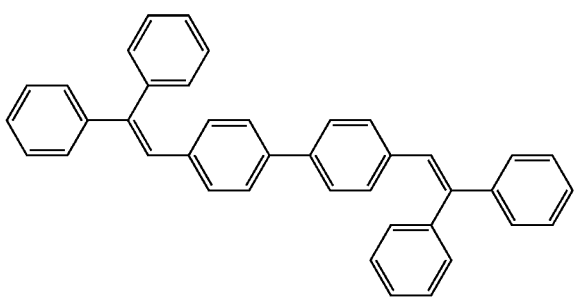

EM1

EXAMPLE 16

A light emitting device was constructed in exactly the same way as in Example 13 except that as the emissive layer region co-deposition was carried out at a thickness of 15 nm using 1,4-diketo-2,5-bis(3,5-dimethylbenzyl)-3,6-bis(4-methylphenyl)pyrrolo[3,4-c]pyrrole (DPP-1) as the host material and EM2 shown below as the dopant material, such that there was 1.0 wt % of the dopant.

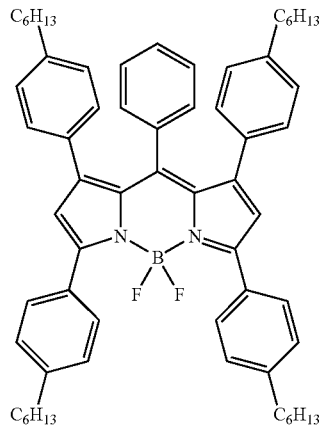

EM2

COMPARATIVE EXAMPLE 3

A light emitting device was prepared in exactly the same way as in Example 16 except that there was used Alq3 as the electron transporting layer.

EXAMPLE 17

A light emitting device was prepared in exactly the same way as in Example 16 except that there was used the Phen-3 shown in Example 8 as the electron transporting layer. The ionization potential of the electron transporting layer was 6.14 eV, the molecular weight was 663 and the glass transition temperature was 150° C.

EXAMPLE 18

A light emitting device was prepared in exactly the same way as in Example 16 except that there was used 1,4-diketo-2,5-bis(4-methylbenzyl)-3,6-bis(1-naphthyl)pyrrolo[3,4-c]pyrrole (DPP-2) as the host material.

EXAMPLE 19

A light emitting device was prepared in exactly the same way as in Example 16 except that there was used 1,4-diketo-2,5-dibenzyl-3,6-bis(1-naphthyl)pyrrolo[3,4-c]pyrrole (DPP-3) as the host material.

EXAMPLE 20

A light emitting device was prepared in exactly the same way as in Example 16 except that there was used 1,4-diketo-2,5-bis(4-isopropylbenzyl)-3,6-bis(1-naphthyl)pyrrolo[3,4-c]pyrrole (DPP-4) as the host material.

EXAMPLE 21

A light emitting device was prepared in exactly the same way as in Example 16 except that there was used 1,4-diketo-2,5-diethyl-3,6-bis(1-naphthyl)pyrrolo[3,4-c]pyrrole (DPP-5) as the host material and EM3 shown below as the dopant material.

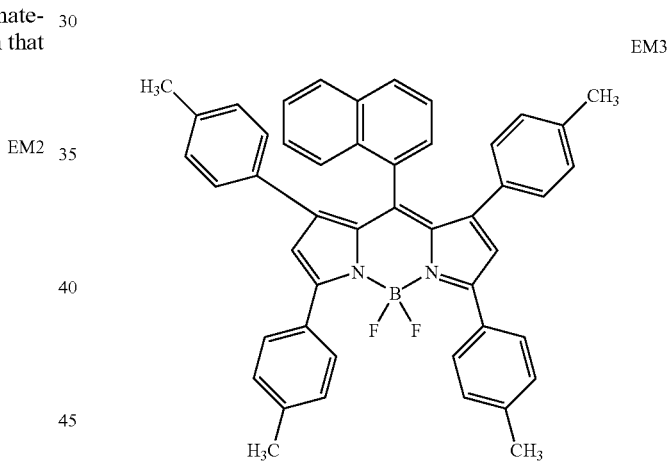

EM3

EXAMPLE 22

A light emitting device was prepared in exactly the same way as in Example 21 except that there was used 1,4-diketo-2,5-bis(4-methylbenzyl)-3,6-bis(1-(4-tolyl)naphthyl)pyrrolo[3,4-c]pyrrole (DPP-6) as the host material.

Table 1 shows the results obtained in the case of Examples 16 to 22 where the electron transporting material of the present invention was applied to a red coloured light emitting device. By employing the electron transporting material of the present invention, red light emission of high chromatic purity and high luminance was obtained.

EXAMPLE 23

A light emitting device was constructed in exactly the same way as in Example 13 except that for the emissive layer region there was employed the BQ-1 of Example 4 as the host material and 4,4-difluoro-1,3,5,7,8-tetramethyl-4-bora-3a,4a-diazaindacene (PM-1) as the dopant material such that the dopant concentration was 0.5%, and for the electron transporting layer there was used BQ-1 in the same way. At a driving voltage of 11 V, from this light emitting device there was obtained green coloured light emission based on the dopant peak emission wavelength of 519 nm, and the luminance was 8,000 cd/m$^2$.

EXAMPLE 24

The same procedure was followed as in Example 13 up to the provision of the hole transporting material layer. Next, as the emissive material there was provided Alq3 at a thickness of 15 nm, and then as the electron transporting material there was provided a layer of ETM2, which is shown below, at a thickness of 35 nm. Thereafter doping was performed with 0.2 nm of lithium and, finally, 150 nm of aluminium was vapour-deposited as the cathode and a 5×5 mm square device produced. The ionization potential of the electron transporting layer was 5.97 eV, the molecular weight was 609 and the glass transition temperature was 112° C. The ionization potential of the emissive layer was 5.79 eV, and so the difference in ionization potential in terms of the emissive layer was 0.18 eV.

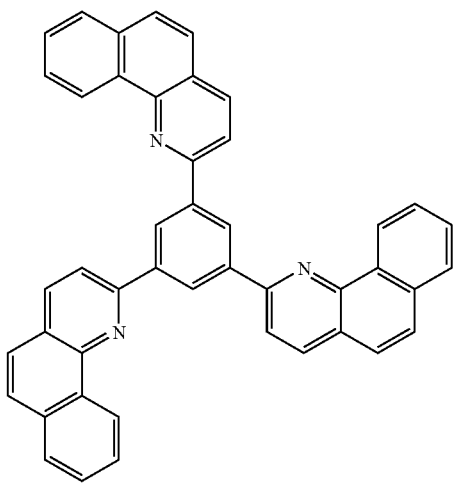

ETM2

COMPARATIVE EXAMPLE 4

A light emitting device was constructed in exactly the same way as in Example 24 except that the thickness of the Alq3 emissive layer was made 50 nm and no electron transporting material was used.

COMPARATIVE EXAMPLE 5

A light emitting device was constructed in exactly the same way as in Example 24 except that BCP was used as the electron transporting material.

EXAMPLE 25

A light emitting device was constructed in exactly the same way as in Example 24 except that the BQ-1 of Example 4 was used as the electron transporting material. The ionization potential of the electron transporting layer was 6.09 eV, the molecular weight was 670 and the glass transition temperature was 165° C. The difference in ionization potential in terms of the emissive layer was 0.30 eV.

The results obtained in Examples 24 and 25 are shown in Table 1 together with those of the comparative examples. It can be seen that the benzoquinoline derivative of the present invention also functioned effectively as the electron transporting material.

EXAMPLE 26

A light emitting device was constructed in exactly the same way as in Example 24 except that there was used EM4, which is shown below, as the emissive material. At a driving voltage of 15 V, from this light emitting device there was obtained a blue coloured light emission based on the EM4 of peak emission wavelength 465 nm. The luminance was 1,200 cd/m$^2$ and the luminance efficiency was 1.0 cd/A. Thus, the benzoquinoline derivative of the present invention also functioned effectively as an electron transporting material for a blue coloured light emitting device.

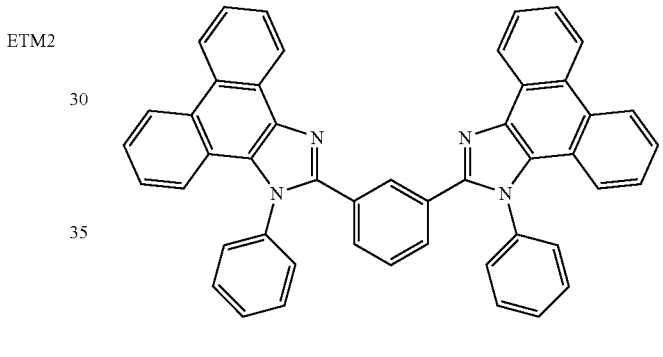

EM4

COMPARATIVE EXAMPLE 6

A light emitting device was constructed in exactly the same way as in Example 26 except that the thickness of the EM4 emissive material was made 50 nm and no electron transporting material was employed. At a driving voltage of 15 V, from this light emitting device there was obtained blue coloured light emission based on the EM4 of peak emission wavelength 465 nm. The luminance was 110 cd/m$^2$ and the luminance efficiency was 0.1 cd/A.

EXAMPLE 27

A light emitting device was constructed in exactly the same way as in Example 24 except that, as the emissive layer region, co-deposition was carried out using tris(5,7-diphenyl-8-quinolinolato)aluminium(III) (Al(dPhq)3) as the host material and 4,4-difluoro-1,3,5,7-tetraphenyl-4-bora-3a,4a-diaza-indacene (PM-2) as the dopant material to a thickness of 15 nm, such that there was 1.0 wt % of the dopant. At a driving voltage of 10 V, from this light emitting device there was obtained red coloured light emission based on the dopant material of peak emission wavelength 615 nm. Thus, the benzoquinoline of the present invention functioned effectively as an electron transporting material for a red light emitting device.

COMPARATIVE EXAMPLE 7

A light emitting device was constructed in exactly the same way as in Example 27 except that Alq3 was used as the electron transporting material. At a driving voltage of 10 V, red coloured light emission was not obtained from this light emitting device and an orange coloured light emission was produced, of peak emission wavelength 615 nm and having a shoulder peak in the region of 535 nm.

EXAMPLE 28

A light emitting device was constructed in the same way as in Example 13 except that there was used the BQ-2 of Example 5 as the electron transporting layer. At a driving voltage of 10 V, from this light emitting device there was obtained green coloured light emission based on the dopant material of peak emission wavelength 523 nm, and the luminance was 20,000 cd/m². The benzoquinoline derivative of the present invention functioned effectively as an electron transporting material for a green light emitting device.

EXAMPLE 29

A light emitting device was constructed in the same way as in Example 16 except that there was used the BQ-3 of Example 5 as the electron transporting layer. At a driving voltage of 14 V, from this light emitting device there was obtained red coloured light emission based on the dopant material of peak emission wavelength 618 nm, and the luminance was 7,500 cd/m². The benzoquinoline derivative of the present invention functioned effectively as an electron transporting material for a red light emitting device.

EXAMPLE 30

A light emitting device was constructed in the same way as in Example 13 except that for the emissive layer region there was used tris(8-quinolinolato)aluminium (III) (Alq3) as the host material and 3-(2-benzothiazolyl)-7-diethylaminocoumarin (Coumarin 2) as the dopant material, and a layer of ETM2 was provided of thickness 25 nm as the electron transporting layer. The ionization potential of the emissive layer was 5.78 eV and the ionization potential of the electron transporting layer was 5.97 eV, so the difference in ionization potentials between the electron transporting layer and the emissive layer was 0.19 eV. Furthermore, the molecular weight of the ETM2 was 609 and the glass transition temperature was 112° C. At a driving voltage of 10 V, from this light emitting device there was obtained green coloured light emission based on the dopant material of peak emission wavelength 513 nm, and the luminance was 5,000 cd/m². Moreover, the percentage retention of the initial luminance after the elapse of 500 hours operation of this light emitting device was 70%, and a uniform emissive surface was maintained.

COMPARATIVE EXAMPLE 8

A light emitting device was constructed in exactly the same way as in Example 30 except that there was used Alq3 as the electron transporting layer. The ionization potential of this electron transporting layer was 5.79 eV and the difference in the ionization potentials of the electron transporting layer and emissive layer was 0.01 eV. Furthermore, the molecular weight of the Alq3 is 459 and its glass transition temperature 180° C. At a driving voltage of 10 V, from this light emitting device there was obtained green coloured light emission based on the dopant material of peak emission wavelength 513 nm, and the luminance was 3,000 cd/m².

COMPARATIVE EXAMPLE 9

A light emitting device was constructed in exactly the same way as in Example 30 except that there was used 2,9-dimethyl-4,7-diphenyl-1,10-phenanthroline (BCP) as the electron transporting layer. The ionization potential of this electron transporting layer was 6.20 eV and the difference in the ionization potentials of the electron transporting layer and emissive layer was 0.42 eV. Furthermore, the molecular weight of BCP is 360 and its crystallization temperature 77° C. At a driving voltage of 10 V, from this light emitting device there was obtained green coloured light emission based on the dopant material of peak emission wavelength 513 nm, and the luminance was 8,000 cd/m². However, the percentage retention of the initial luminance after the elapse of 500 hours operation of this light emitting device was below 50%, and unevenness of the emissive surface was observed.

EXAMPLE 31

A light emitting device was constructed in exactly the same way as in Example 30 except that for the emissive layer region there was used EM4 as the host material and EM5, which is shown below, as the dopant material. The ionization potential of this emissive layer was 5.65 eV and the difference in the ionization potentials of the electron transporting layer and the emissive layer was 0.32 eV. At a driving voltage of 15 V, from this light emitting device there was obtained blue coloured light emission based on the dopant material of peak emission wavelength 477 nm, and the luminance was 3,500 cd/m². Thus, the electron transporting material of the present invention also functioned effectively in a blue light emitting device.

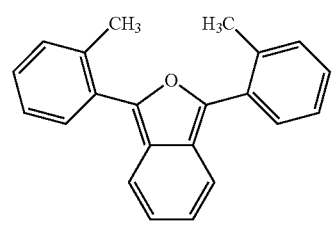

EM5

EXAMPLE 32

A light emitting device was constructed in exactly the same way as in Example 30 except that for the emissive layer region there was codeposited, to a thickness of 15 nm, 1,4-diketo-2,5-bis(3,5-di-tert-butylbenzyl)-3,6-bis(4-biphenyl)pyrrolo[3,4-c]pyrrole (DPP-7) as the host material and EM6, which is shown below, as the dopant material, such that there was 1.0 wt % of the dopant. The ionization potential of the emissive layer was 5.79 eV and the difference in the ionization potentials of the electron transporting layer and the emissive layer was 0.18 eV. At a driving voltage of 14 V, from this light emitting device there was obtained red coloured light emission based on the dopant material of peak emission wavelength 629 nm, and the luminance was 8,000 cd/m². Thus, the electron transporting material of the present invention also functioned effectively in a red light emitting device.

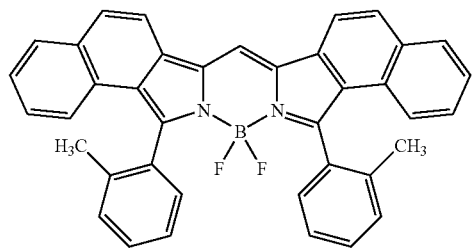

EM6

EXAMPLE 33

A light emitting device was constructed in exactly the same way as in Example 32 except that there was used BQ-1 of Example 4 as the electron transporting layer. The ionization potential of the BQ-1 was 6.09 eV and the difference in the ionization potentials of the electron transporting layer and the emissive layer was 0.30 eV. Furthermore, the molecular weight of BQ-1 was 670, the glass transition temperature was 165° C. and no cold crystallization temperature was observed.

At a driving voltage of 14 V, from this light emitting device there was obtained red coloured light emission based on the dopant material of peak emission wavelength 629 nm, and the luminance was 9,000 cd/m². Thus, the electron transporting material of the present invention also functioned effectively in a red light emitting device.

COMPARATIVE EXAMPLE 10

A light emitting device was constructed in exactly the same way as in Example 32 except that there was used Alq3 as the electron transporting layer. The difference in the ionization potentials of the emissive layer and the electron transporting layer was 0 eV. At a driving voltage of 10 V, no red coloured light emission was obtained from this light emitting device. There was produced orange coloured light emission where there was a shoulder peak in the vicinity of 535 nm along with the peak emission wavelength of 629 nm.

EXAMPLE 34

A light emitting device was constructed in exactly the same way as in Example 13 except that there was provided a layer of Alq3 of thickness 15 nm as the emissive layer and then there was provided a layer of the Phen-6 of Example 11 of thickness 35 nm as the electron transporting layer. At a driving voltage of 10 V, from this light emitting device there was obtained green coloured light emission based on the Alq3 of peak emission wavelength 536 nm, and the luminance was 4,000 cd/m². Furthermore, the percentage retention of the initial luminance after the elapse of 500 hours operation of this light emitting device was 75%, and a uniform emissive surface was maintained.

EXAMPLE 35

Stages prior to the vapour-deposition were carried out in the same way as in Example 13. Then, by means of a resistance heating method, 20 nm of CuPc was vapour-deposited as the hole injecting material and 100 nm of α-NPD as the hole transporting material. Next, as the emissive material a layer of Alq3 was provided of thickness of 50 nm. Then, a layer of the Phen-1 of Example 6 was provided of thickness 100 nm as the electron transporting material. Thereafter, there was 0.5 nm lithium doping onto the organic layer, following which 200 nm of aluminium was evaporated as the cathode, and a 5×5 mm square device produced. Film thicknesses were the values displayed by means of a quartz crystal oscillator type film thickness monitor. The ionization potential of the electron transporting layer was 6.09 eV, its molecular weight was 689 and the glass transition temperature was 197° C. The ionization potential of the emissive layer was 5.79 eV, and so the difference in ionization potentials was 0.30 eV. From this light emitting device, there was obtained high luminance green coloured light emission of emission wavelength 530 nm and luminance 20,000 cd/m². This light emitting device retained at least 80% of its luminance over a 1000 hour period. Furthermore, when this light emitting device was subjected to 1 mA pulse driving (duty ratio 1/60, 60 mA DC at time of pulse) within a vacuum cell, excellent light emission was confirmed.

EXAMPLE 36

A light emitting device was constructed in exactly the same way as in Example 35 except that, for the emissive material, Alq3 was employed as the host material and 4-(dicyanomethylene)-2-tert-butyl-6-(1,1,7,7-tetramethylju-lolidyl-9-enyl)-4H-pyran (DCJTB) as the guest material, such that the dope concentration was 2%. From this light emitting device, there was obtained high luminance red-orange coloured light emission of emission wavelength 630 nm and luminance 10,000 cd/m². This light emitting device retained at least 80% of its luminance over a 1000 hour period.

EXAMPLE 37

A light emitting device was constructed in exactly the same way as in Example 35 except that, as the host material, there was used 4,4'-bis(diphenylvinyl)biphenyl (DPVBi). From this light emitting device, there was obtained high luminance blue coloured light emission of emission wavelength 460 nm and luminance 10,000 cd/m².

EXAMPLE 38

A light emitting device was constructed in exactly the same way as in Example 35 except that, as the host material, there was used DPP-1 and, as the guest material, there was used PM-2, such that the dope concentration was 1%. From this light emitting device, there was obtained a high luminance red coloured light emission of emission wavelength 610 nm and luminance 10,000 cd/m².

COMPARATIVE EXAMPLE 11

A light emitting device was constructed in exactly the same way as in Example 38 except that there was used Alq3 as the electron transporting material. From this light emitting device, in addition to the red light emission from the emissive material there was observed green light emission from the electron transporting material, so the chromatic purity was markedly impaired.

EXAMPLE 39

A light emitting device was constructed in exactly the same way as in Example 35 except that, as the host material, there was used 1,4-diketo-2,5-bis(3,5-di-tert-butylbenzyl)-3,6-bis(3-methoxyphenyl)pyrrolo[3,4-c]pyrrole (DPP-8) and, as the guest material, there was used 4,4-difluoro-1,3,5,7-tetra(4-methylphenyl)-8-phenyl-4-bora-3a,4a-diaza-indacene (PM-3), such that the dope concentration was 1%. From this light emitting device, there was obtained high luminance red coloured light emission of emission wavelength 625 nm and luminance 10,000 cd/m$^2$.

EXAMPLE 40

A light emitting device was constructed in exactly the same way as in Example 35 except that, as the host material, there was used DPP-7 and, as the guest material, there was used 4,4-difluoro[3-phenyl-1-[(3-phenyl-2H-benzo[c]isoindol-1-yl)methylene-1H-benzo[c]isoindolato-N1,N2]borane (PM-4), such that the dope concentration was 1%. From this light emitting device, there was obtained a high luminance red coloured light emission of emission wavelength 635 nm and luminance 10,000 cd/m$^2$.

EXAMPLE 41

A light emitting device was constructed in exactly the same way as in Example 35 except that, as the host material there was used DPP-2 and, as the guest material, there was used 4,4-difluoro-1,3,5,7-tetra(4-hexylphenyl)-4-bora-3a,4a-diaza-indacene (PM-5), such that the dope concentration was 1%. From this light emitting device, there was obtained high luminance red coloured light emission of emission wavelength 629 nm and luminance 10,000 cd/m$^2$.

EXAMPLE 42

A light emitting device was constructed in exactly the same way as in Example 35 except that there was used DPP-3 as the host material and EM2 as the guest material, such that the dope concentration was 1%. From this light emitting device, there was obtained high luminance red coloured light emission of emission wavelength 615 nm and luminance 10,000 cd/m$^2$.

EXAMPLE 43

A light emitting device was constructed in exactly the same way as in Example 35 except that there was used DPP-5 as the host material and EM3 as the guest material, such that the dope concentration was 1%. From this light emitting device, there was obtained high luminance red coloured light emission of emission wavelength 620 nm and luminance 10,000 cd/m$^2$.

EXAMPLE 44

A light emitting device was constructed in exactly the same way as in Example 35 except that there was used 1,4-diketo-2,5-bis(3,5-dimethylbenzyl)-3,6-bis(4-ethylphenyl)pyrrolo[3,4-c]pyrrole (DPP-9) as the host material and, 4,4-difluoro-1,3,5,7-tetra(4-butylphenyl)-8-phenyl-4-bora-3a,4a-diaza-indacene (PM-6) as the guest material, such that the dope concentration was 1%. From this light emitting device, there was obtained high luminance red coloured light emission of emission wavelength 615 nm and luminance 10,000 cd/m$^2$.

EXAMPLE 45

A light emitting device was constructed in exactly the same way as in Example 35 except that there was used the Phen-2 of Example 7 as the electron transporting material. The ionization potential of the electron transporting layer was 6.11 eV, its molecular weight was 677 and the glass transition temperature was 175° C. The ionization potential of the emissive layer was 5.79 eV and so the difference in ionization potentials was 0.32 eV. From this light emitting device, there was obtained high luminance green coloured light emission of emission wavelength 530 nm and luminance 20,000 cd/m$^2$. This light emitting element maintained at least 80% of its luminance over a 1000 hour period. Furthermore, when this light emitting device was subjected to 1 mA pulse driving (duty ratio 1/60, 60 mA DC at time of pulse) within a vacuum cell, excellent light emission was confirmed.

EXAMPLE 46

A light emitting device was constructed in exactly the same way as in Example 36 except that there was used the Phen-2 of Example 7 as the electron transporting material. From this light emitting device, there was obtained high luminance red-orange coloured light emission of emission wavelength 630 nm and luminance 10,000 cd/m$^2$. This light emitting element maintained at least 80% of its luminance over a 1000 hour period.

EXAMPLE 47

A light emitting device was constructed in exactly the same way as in Example 37 except that there was used the Phen-2 of Example 7 as the electron transporting material. From this light emitting device, there was obtained high luminance blue coloured light emission of emission wavelength 460 nm and luminance 10,000 cd/m$^2$.

EXAMPLE 48

A light emitting device was constructed in exactly the same way as in Example 38 except that there was used the Phen-2 of Example 7 as the electron transporting material. From this light emitting device, there was obtained high luminance red coloured light emission of emission wavelength 610 nm and luminance 10,000 cd/m$^2$.

EXAMPLE 49

A light emitting device was constructed in exactly the same way as in Example 44 except that there was used the TPM-dNTR of Example 12 as the electron transporting material. From this light emitting device, there was obtained high luminance red coloured light emission of emission wavelength 615 nm and luminance 10,000 cd/m$^2$.

EXAMPLE 50

A glass substrate on which a 150 nm ITO transparent electroconductive film had been deposited (produced by the Asahi Glass Co., 15 Ω/□, electron beam vapour-deposited product) was cut to 30×40 mm and, by a photolithography method, pattern processing was carried out in the form of 32 stripes×300 μm pitch (remaining width 270 μm). In order to facilitate external electrical connection, the ITO stripes were widened to a 1.27 mm pitch (width of opening portion 800

μm) at one side in the lengthwise direction. The substrate obtained was subjected to ultrasonic washing for 15 minute periods with acetone and "Semico-Clean 561" respectively, after which washing was carried out with ultra-pure water. Next, 15 minutes ultrasonic washing was performed with isopropyl alcohol, after which it was immersed for 15 minutes in hot methanol and dried. Just prior to producing the device, this substrate was given a 1 hour UV-ozone treatment, then placed in vacuum vapour-deposition apparatus and the apparatus evacuated until the degree of vacuum inside was less than $5 \times 10^{-4}$ Pa. By means of a resistance heating method, firstly there was vapour-deposited 10 nm of CuPc, and then there was vapour-deposited 50 nm of α-NPD. Next there was codeposited to a thickness of 25 nm the emissive layer region, using Alq3 as the host material and Coumarin-1 as the dopant material, such that there was 1.0 wt % of dopant. Thereafter, there was provided a ETM1 layer of thickness 25 nm as the electron transporting layer. The ionization potential of the electron transporting layer was 6.07 eV, the molecular weight was 672, the glass transition temperature 219° C. and the cold crystallization temperature 352° C. Next, under vacuum, mask exchange was performed with a mask comprising a kovar sheet of thickness 50 μm in which sixteen 250 μm apertures (remaining width 50 μm, corresponding to a 300 μm pitch) had been provided by wet etching, so as to intersect the ITO stripes at right angles, and then this fixed with a magnet from the underside so that the mask and ITO substrate closely adhered. After doping the organic layer with 0.5 nm of lithium, there was vapour-deposited 200 nm of aluminium and a 32×16 dot matrix device produced. When this device was subjected to matrix driving, character display was possible without cross-talk.

EXAMPLE 51

A 32×16 dot matrix device was constructed in exactly the same way as in Example 50 except that there was used the Phen-6 of Example 11 as the electron transporting layer. When this device was subjected to matrix driving, character display was possible without cross-talk.

EXAMPLE 52

A 32×16 dot matrix device was constructed in exactly the same way as in Example 50 except that a 25 nm layer of Alq3 was provided as the emissive layer and a 25 nm layer of ETM2 was provided as the electron transporting, layer. When this device was subjected to matrix driving, character display was possible without cross-talk.

EXAMPLE 53

The stages up to the vapour-deposition were carried out in the same way as in Example 50. Then, by means of a resistance heating method, there was vapour-deposited 150 nm of 4,4'-bis(N-(m-tolyl)-N-phenylamino)biphenyl as the hole transporting material, and there was evaporated 50 nm of Alq3 as the emissive material. Next, as the electron transporting material there was provided the Phen-1 of Example 6 at a layer thickness of 100 nm. The film thicknesses were the values displayed by means of a quartz crystal oscillator type film thickness monitor. Then, under vacuum, mask exchange was performed with a mask comprising a kovar sheet of thickness 50 μm in which sixteen 250 μm apertures (remaining width 50 μm, corresponding to a 300 μm pitch) had been provided by wet etching, so as to intersect the ITO stripes at right angles, and this then fixed with a magnet from the underside so that the mask and ITO substrate closely adhered. After doping the organic layer with 0.5 nm of lithium, there was vapour-deposited 200 nm of aluminium and a 32×16 dot matrix device produced. When this device was subjected to matrix driving, character display was possible without cross-talk.

EXAMPLE 54

A 32×16 dot matrix device was constructed in exactly the same way as in Example 53 except that there was used the Phen-2 of Example 7 as the electron transporting layer. When this device was subjected to matrix driving, character display was possible without cross-talk.

INDUSTRIAL APPLICATION POTENTIAL

The present invention provides a light emitting device of outstanding thermal stability, high electrical energy utilization efficiency and excellent chromatic purity, together with light emitting device materials for use therein.

TABLE 1

| | | Corresponding Claim or Corresponding Example | Properties | | | Results | | | | |
|---|---|---|---|---|---|---|---|---|---|---|
| | | | Electron Transporting Layer | | IP difference [eV] | EL Device | | | | |
| | Structure | | Mw | Tg (° C.) | IP [eV] | | Colour | Wavelength [nm] | Luminance (voltage) [cd/m²] | Efficiency [cd/A] | Retention [%] | Emissive Surface |
| Example 1 | basic spiro structure synthesis (1) | 9 | | | | | | | | | |
| Example 2 | basic spiro structure synthesis (2) | 9 | | | | | | | | | |
| Example 3 | introduction of reactive substituents into basic spiro structure | 9 | | | | | | | | | |
| Example 4 | benzoquinoline derivative synthesis | (3) | | | | | | | | | |

TABLE 1-continued

|  | Structure | Corresponding Claim or Corresponding Example | Results | | | | | | | | | |
|---|---|---|---|---|---|---|---|---|---|---|---|---|
|  |  |  | Properties | | | | EL Device | | | | | |
|  |  |  | Electron Transporting Layer | | | IP differ-ence [eV] | | | | | | |
|  |  |  | Mw | Tg (° C.) | IP [eV] |  | Colour | Wave-length [nm] | Luminance (voltage) [cd/m²] | Efficiency [cd/A] | Reten-tion [%] | Emiss-ive Surface |
| Example 5 | (BQ-1) benzoquinoline derivative syntheses | (3) | | | | | | | | | | |
| Example 6 | (BQ-2,3) phenanthroline derivative synthesis | 9 | | | | | | | | | | |
| Example 7 | (Phen-1) phenanthroline derivative synthesis | 10 | | | | | | | | | | |
| Example 8 | (Phen-2) phenanthroline derivative synthesis | (5) | | | | | | | | | | |
| Example 9 | (Phen-3) phenanthroline derivative synthesis | (5) | | | | | | | | | | |
| Example 10 | (Phen-4) phenanthroline derivative synthesis | (5) | | | | | | | | | | |
| Example 11 | (Phen-5) 1,7-phenanthroline derivative synthesis | (5) | | | | | | | | | | |
| Example 12 | (Phen-6) naphthyridine derivative synthesis | 10 | | | | | | | | | | |
| Example 13 | (TPM-dNTR) Alq3 + Coumarin-1 (green)/ETM1 (phenanthroline multimer) | 4-8 | 672 | 219 | 6.07 | 0.29 | green | 523 | 38,000(10 V) | | 80 | uniform |
| Comp. Ex. 1 | Alq3 + Coumarin-1 (green)/Alq3 | Example 13 | 459 | 180 | 5.79 | 0.01 | green | 523 | 6,000(10 V) | | | |
| Comp. Ex. 2 | Alq3 + Coumarin-1 (green)/BCP | Example 13 | 360 | <77 | 6.2 | 0.42 | green | 523 | 12,000(10 V) | | <50 | uneven |
| Example 14 | carbazole + phosphorescent guest (green)/ETM1 (phenanthroline multimer) | 4, 5, 7, 8 | 672 | 219 | 6.07 | | green | 515 | 1,000(6 V) | | | |
| Example 15 | EM1(blue)/ETM1 (phenanthroline multimer) | 4, 5, 7 | 672 | 219 | 6.07 | | blue | 463 | 8,000(15 V) | | | |
| Example 16 | DPP-1 + EM2 (red)/ETM1 (phenanthroline multimer) | 4, 5, 7, 8 | 672 | 219 | 6.07 | | red | 618 | 10,000 | | | |
| Comp. Ex. 3 | DPP-1 + EM2 (red)/Alq | Examples 16-22 | 459 | 180 | 5.79 | | orange | 618, 535 | | | | |
| Example 17 | DPP-1 + EM2 (red)/Phen-3 (phenanthroline multimer) | 4, 5, 7, 8 | 663 | 150 | 6.14 | | red | 618 | 7,000 | | | |
| Example 18 | DPP-2 + EM2 (red)/ETM1 (phenanthroline multimer) | 4, 5, 7, 8 | 672 | 219 | 6.07 | | red | 618 | 8,500 | | | |
| Example 19 | DPP-3 + EM2 (red)/ETM1 (phenanthroline multimer) | 4, 5, 7, 8 | 672 | 219 | 6.07 | | red | 618 | 6,500 | | | |
| Example 20 | DPP-4 + EM2 (red)/ETM1 (phenanthroline multimer) | 4, 5, 7, 8 | 672 | 219 | 6.07 | | red | 618 | 7,000 | | | |
| Example 21 | DPP-5 + EM3 (red)/ETM1 (phenanthroline multimer) | 4, 5, 7, 8 | 672 | 219 | 6.07 | | red | 619 | 8,900 | | | |

TABLE 1-continued

| | | Corresponding Claim or Corresponding Example | Results | | | | | | | | |
|---|---|---|---|---|---|---|---|---|---|---|---|
| | | | Properties | | | EL Device | | | | | |
| | | | Electron Transporting Layer | | | IP differ- ence [eV] | Colour | Wave- length [nm] | Luminance (voltage) [cd/m²] | Efficiency [cd/A] | Reten- tion [%] | Emiss- ive Surface |
| | Structure | | Mw | Tg (° C.) | IP [eV] | | | | | | | |
| Example 22 | DPP-6 + EM3 (red)/ETM1 (phenanthroline multimer) | 4, 5, 7, 8 | 672 | 219 | 6.07 | | red | 619 | 6,600 | | | |
| Example 23 | BQ-1 (benzoquinoline multimer) + PM-1 (green)/BQ-1 | 1(b), 2, 3 | | | | | green | 519 | 8,000(11 V) | | | |
| Example 24 | Alq3 (green)/ETM2 (benzoquinoline multimer) | 1(b), 2-4, 6, 7 | 609 | 112 | 5.97 | 0.18 | green | 536 | 4,000 | 2.0 | 80 | uniform |
| Comp. Ex. 4 | Alq3 (green)/Alq | Examples 24, 25 | 459 | 180 | 5.79 | 0 | green | 536 | 3,800 | 1.9 | | |
| Comp. Ex. 5 | Alq3 (green)/BCP | Examples 24, 25 | 360 | <77 | 6.2 | 0.41 | green | 536 | 3,000 | 1.4 | <50 | uneven |
| Example 25 | Alq3 (green)/BQ-1 (benzoquinoline multimer) | 1(b), 2-4, 6, 7 | 670 | 165 | 6.09 | 0.30 | green | 536 | 3,500 | 1.8 | 80 | uniform |
| Example 26 | EM4 (blue)/ETM2 (benzoquinoline multimer) | 1(b), 2-4, 7 | 609 | 112 | 5.97 | | blue | 465 | 1200(15 V) | 1.0 | | |
| Comp. Ex. 6 | EM4 (blue) | Example 26 | | | | | blue | 465 | 110(15 V) | 0.1 | | |
| Example 27 | Al(dPhq)3 + PM-2 (red)/ETM2 (benzoquinoline multimer | 1(b), 2-4, 7-8 | 609 | 112 | 5.97 | | red | 615 | | | | |

Note 1) The structures in Examples 13 to 27 relate to just the emissive layer/electron transporting layer portion of the device structure
Note 2) Mw = molecular weight, Tg = glass transition temperature, IP = ionization potential, IP difference = difference in ionization potentials between the electron transporting layer and emissive layer

TABLE 2

| | | Corresponding Claim or Corresponding Example | Results | | | | | | | | |
|---|---|---|---|---|---|---|---|---|---|---|---|
| | | | Properties | | | EL Device | | | | | |
| | | | Electron Transporting Layer | | | IP differ- ence [eV] | Colour | Wave- length [nm] | Luminance (voltage) [cd/m²] | Efficiency [cd/A] | Reten- tion [%] | Emiss- ive Surface |
| | Structure | | Mw | Tg (° C.) | IP [eV] | | | | | | | |
| Comp. Ex. 7 | Al(dPhq)3 + PM-2 (red)/Alq | Example 27 | 459 | 180 | 5.79 | | orange | 615, 535 | | | | |
| Example 28 | Alq3 + Coumarin-1 (green)/BQ-2 (benzoquinoline multimer) | 1(b), 2, 3 | | | | | green | 523 | 20,000 (10 V) | | | |
| Example 29 | DPP-1 + EM2 (red)/BQ-3 (benzoquinoline multimer) | 1(b), 2, 3 | | | | | red | 618 | 7,500(14 V) | | | |
| Example 30 | Alq3 + Coumarin-2 (green)/ETM2 (benzoquinoline multimer) | 1(b), 2-4, 6-8 | 609 | 112 | 5.97 | 0.19 | green | 513 | 5,000(10 V) | | 70 | uniform |
| Comp. Ex. 8 | Alq3 + Coumarin-2 (green)/Alq | Example 30 | 459 | 180 | 5.79 | 0.01 | green | 513 | 3,000(10 V) | | | |
| Comp. Ex. 9 | Alq3 + Coumarin-2 (green)/BCP | Example 30 | 360 | <77 | 6.20 | 0.42 | green | 513 | 8,000(10 V) | | <50 | uneven |
| Example 31 | EM4 + EM5 (blue)/ETM2 (benzoquinoline multimer) | 1(b), 2-4, 6-8 | 609 | 112 | 5.97 | 0.32 | blue | 477 | 3,500(15 V) | | | |

TABLE 2-continued

| | | | Properties | | | Results | | | | |
|---|---|---|---|---|---|---|---|---|---|---|
| | | Corresponding | Electron Transporting Layer | | IP differ- | EL Device | | | | |
| | Structure | Claim or Corresponding Example | Mw | Tg (° C.) | IP [eV] | ence [eV] | Colour | Wave-length [nm] | Luminance (voltage) [cd/m²] | Efficiency [cd/A] | Reten-tion [%] | Emiss-ive Surface |

| | Structure | Corresponding Claim or Example | Mw | Tg (°C.) | IP [eV] | IP difference [eV] | Colour | Wavelength [nm] | Luminance (voltage) [cd/m²] | Efficiency [cd/A] | Retention [%] | Emissive Surface |
|---|---|---|---|---|---|---|---|---|---|---|---|---|
| Example 32 | DPP-7 + EM6 (red)/ETM2 (benzoquinoline multimer) | 1(b), 2-4, 6-8 | 609 | 112 | 5.97 | 0.18 | red | 629 | 8,000(14 V) | | | |
| Example 33 | DPP-7 + EM6 (red)/BQ-1 (benzoquinoline multimer) | 1(b), 2-4, 6-8 | 670 | 165 | 6.09 | 0.30 | red | 629 | 9,000(14 V) | | | |
| Comp. Ex. 10 | DPP-7 + EM6 (red)/Alq | Examples 32, 33 | 459 | 180 | 5.79 | 0 | orange | 629, 535 | | | | |
| Example 34 | Alq (green)/Phen-6 (1,7-phenanthroline multimer) | 1(a) | | | | | green | 536 | 4,000(10 V) | | 75 | uniform |
| Example 35 | Alq (green)/Phen-1 (spiro phenanthroline multimer) | 1(c), 4-7 | 689 | 197 | 6.09 | 0.30 | green | 530 | 20,000 | | >80 | |
| Example 36 | Alq + DCJTB (red)/Phen-1 (spiro phenanthroline multimer) | 1(c), 4, 5, 7, 8 | 689 | 197 | 6.09 | | red | 630 | 10,000 | | >80 | |
| Example 37 | DPVBi (blue)/Phen-1 (spiro phenanthroline multimer) | 1(c), 4, 5, 7 | 689 | 197 | 6.09 | | blue | 460 | 10,000 | | | |
| Example 38 | DPP-1 + PM-2 (red)/Phen-1 (spiro phenanthroline multimer) | 1(c), 4, 5, 7, 8 | 689 | 197 | 6.09 | | red | 610 | 10,000 | | | |
| Comp. Ex. 11 | DPP-1 + PM-2 (red)/Alq | Example 38 | 459 | 180 | 5.79 | | red + green | | | | | |
| Example 39 | DPP-8 + PM-3 (red)/Phen-1 (spiro phenanthroline multimer) | 1(c), 4, 5, 7, 8 | 689 | 197 | 6.09 | | red | 625 | 10,000 | | | |
| Example 40 | DPP-7 + PM-4 (red)/Phen-1 (spiro phenanthroline multimer) | 1(c), 4, 5, 7, 8 | 689 | 197 | 6.09 | | red | 635 | 10,000 | | | |
| Example 41 | DPP-2 + PM-5 (red)/Phen-1 (spiro phenanthroline multimer) | 1(c), 4, 5, 7, 8 | 689 | 197 | 6.09 | | red | 629 | 10,000 | | | |
| Example 42 | DPP-3 + EM2 (red)/Phen-1 (spiro phenanthroline multimer) | 1(c), 4, 5, 7, 8 | 689 | 197 | 6.09 | | red | 615 | 10,000 | | | |
| Example 43 | DPP-5 +EM3 (red)/Phen-1 (spiro phenanthroline multimer) | 1(c), 4, 5, 7, 8 | 689 | 197 | 6.09 | | red | 620 | 10,000 | | | |
| Example 44 | DPP-9 + PM-6 (red)/Phen-1 (spiro phenanthroline multimer). | 1(c), 4, 5, 7, 8 | 689 | 197 | 6.09 | | red | 615 | 10,000 | | | |
| Example 45 | Alq(green)/Phen-2 (tetraphenylmethane phenanthroline multimer) | 1(d), 4-7 | 677 | 175 | 6.11 | 0.32 | green | 530 | 20,000 | | | |
| Example 46 | Alq + DCJTB red-orange/Phen-2 (tetraphenylmethane phenanthroline multimer) | 1(d), 4, 5, 7, 8 | 677 | 175 | 6.11 | | red | 630 | 10,000 | | | |

TABLE 2-continued

| | | Corresponding Claim or Corresponding Example | Properties | | | | Results | | | | |
|---|---|---|---|---|---|---|---|---|---|---|---|
| | | | Electron Transporting Layer | | | IP differ- ence [eV] | EL Device | | | | |
| | Structure | | Mw | Tg (° C.) | IP [eV] | | Colour | Wave- length [nm] | Luminance (voltage) [cd/m²] | Efficiency [cd/A] | Reten- tion [%] | Emiss- ive Surface |
| Example 47 | DPVBi (blue)/Phen-2 (tetraphenyl-methane phenanthroline multimer) | 1(d), 4, 5, 7 | 677 | 175 | 6.11 | | blue | 460 | 10,000 | | | |
| Example 48 | DPP-1 + PM-2 (red)/Phen-2 (tetraphenylmethane phenanthroline multimer) | 1(d), 4, 5, 7, 8 | 677 | 175 | 6.11 | | red | 610 | 10,000 | | | |
| Example 49 | DPP-9 + PM-6 (red)/TPM-dNTR (tetraphenylmethane derivative) | 1(d), 4, 5, 7, 8 | 677 | 175 | 6.11 | | red | 615 | 10,000 | | | |
| Example 50 | dot matrix (using ETM1 (phenanthroline multimer)) | 11 | | | | | | | | | | |
| Example 51 | dot matrix (using Phen-6 (1,7-phenanthroline multimer)) | 11 | | | | | | | | | | |
| Example 52 | dot matrix (using ETM2 (benzoquinoline multimer)) | 11 | | | | | | | | | | |
| Example 53 | dot matrix (using Phen-1 (spiro-phenanthroline multimer)) | 11 | | | | | | | | | | |
| Example 54 | dot matrix (using Phen-2 (tetraphenylmethane-phenanthroline multimer)) | 11 | | | | | | | | | | |

Note 1) The structures in Examples 28 to 49 relate to just the emissive layer/electron transporting layer portion of the device structure
Note 2) Examples 50 to 54 are examples of dot matrixes, with only the compound of the present invention used being noted
Note 3) Mw = molecular weight, Tg = glass transition temperature, IP = ionization potential, IP difference = difference in ionization potentials of the electron transporting layer and emissive layer

The invention claimed is:

1. A light emitting device comprising an anode, an emissive layer, an electron transporting layer and a cathode that are provided as layers in turn and which emits light by electrical energy, and the electron transporting layer comprises an compound of a molecular weight of at least 400, a glass transition temperature at least 90° C., an ionization potential at least 5.9 eV and comprising a phenanthroline skeletal structure, wherein the compound comprises a plurality of phenanthroline skeletal structures that are connected by conjugated bonds, an aromatic hydrocarbon, an aromatic heterocycle or combinations thereof.

2. The display comprising the light emitting device of claim 1.

3. A light emitting device comprising an anode, an emissive layer, an electron transporting layer and a cathode that are provided as layers in turn and which emits light by electrical energy, and the electron transporting layer comprises an compound of a molecular weight of at least 400, a glass transition temperature at least 90° C., an ionization potential at least 5.9 eV and comprising a plurality of benzoquinoline skeletal structures, wherein said plurality of benzoquinoline skeletal structures are connected by conjugated bonds, an aromatic hydrocarbon, an aromatic heterocycle or combinations thereof.

4. The display comprising the light emitting device of claim 3.

5. A light emitting device comprising an anode, an emissive layer, an electron transporting layer and a cathode that are provided as layers in turn, the device emits light by electrical energy and said electron transporting layer comprises at least one type of compound comprising a plurality of 1,7-phenanthroline skeletal structures or a plurality of benzoquinoline skeletal structures, wherein said plurality of 1,7-phenanthroline skeletal structures or a plurality of benzoquinoline skeletal structures are connected by conjugated bonds, an aromatic hydrocarbon, an aromatic heterocycle or combinations thereof.

6. The display comprising the light emitting device of claim 5.

7. A light emitting device comprising an anode, an emissive layer, an electron transporting layer and a cathode that are provided as layers in turn, the device emits light by electrical energy and said electron transporting layer comprises a spiro compound selected from formulas below:
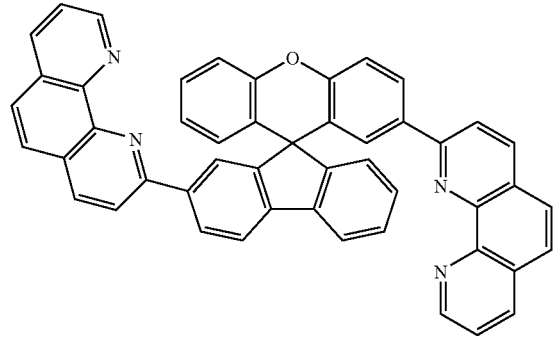
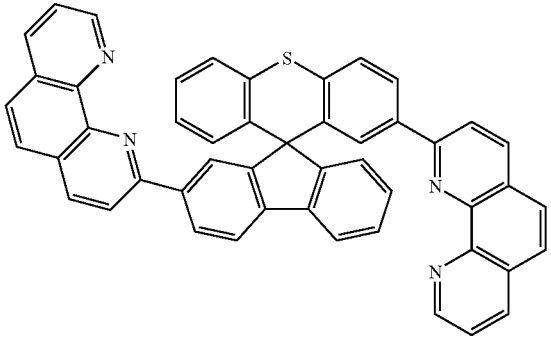
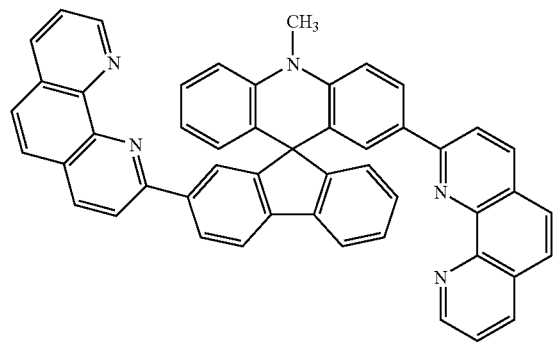
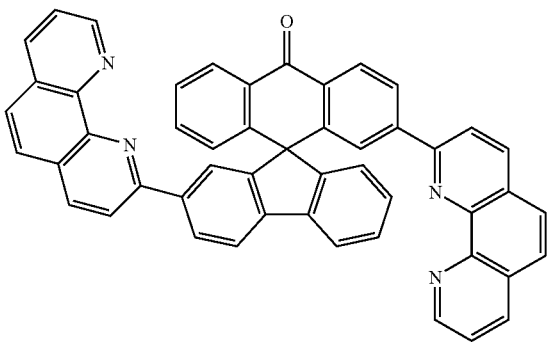
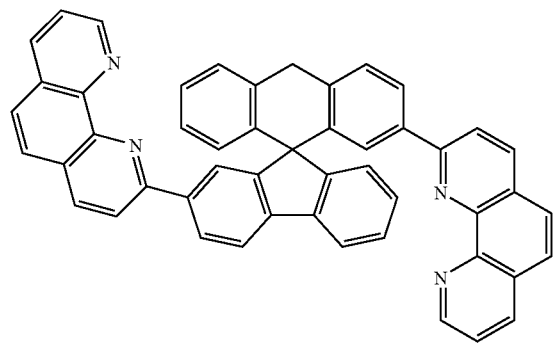
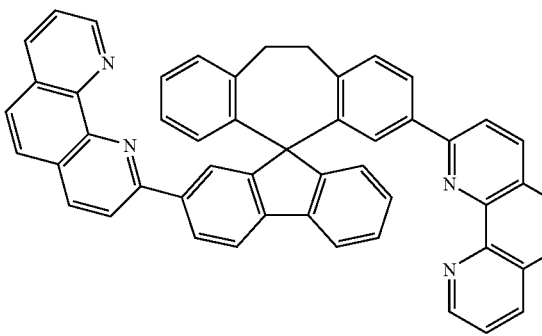
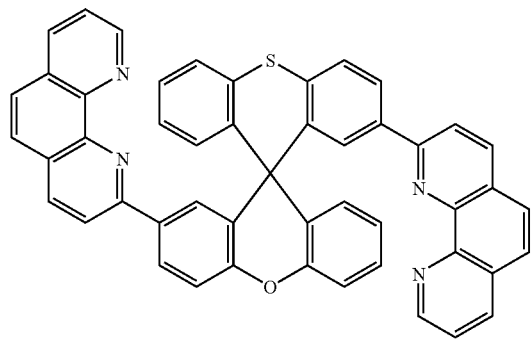
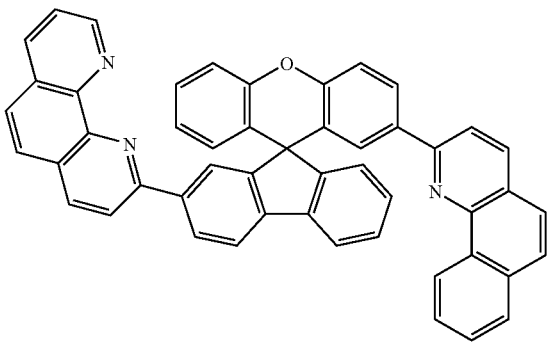

-continued
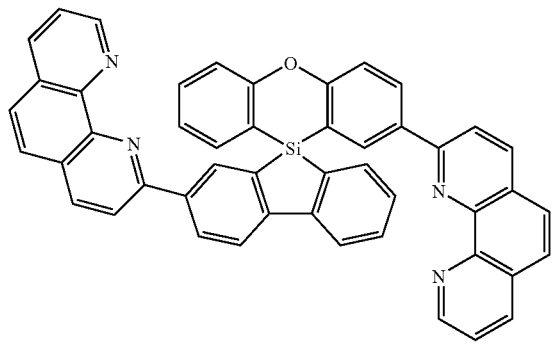
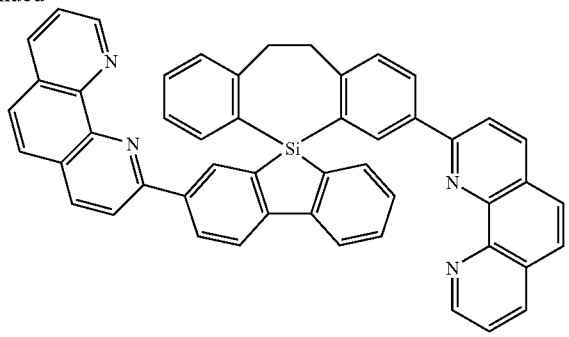
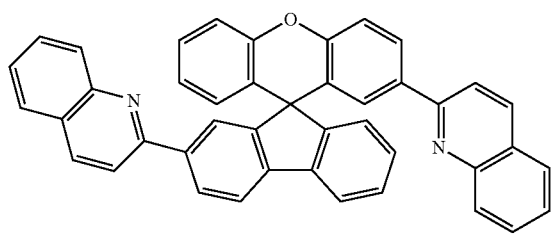
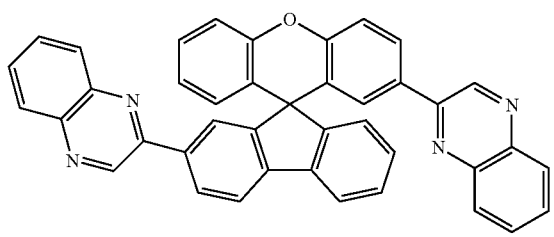
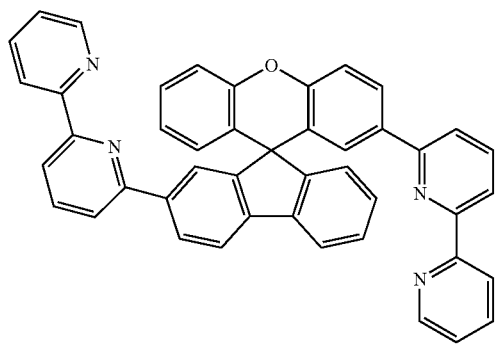
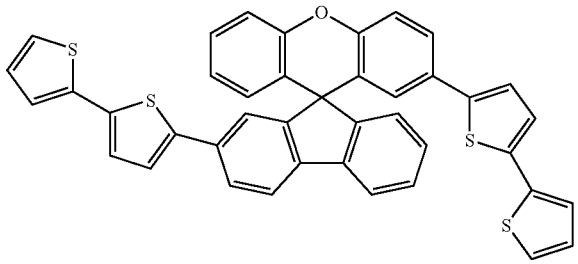
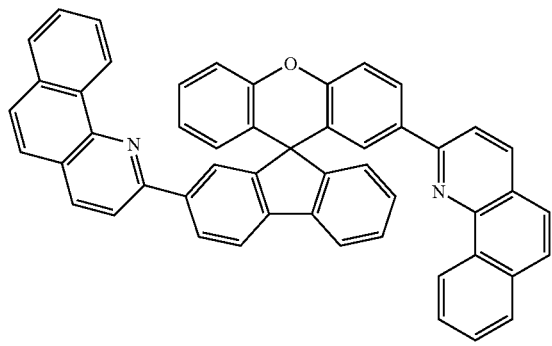
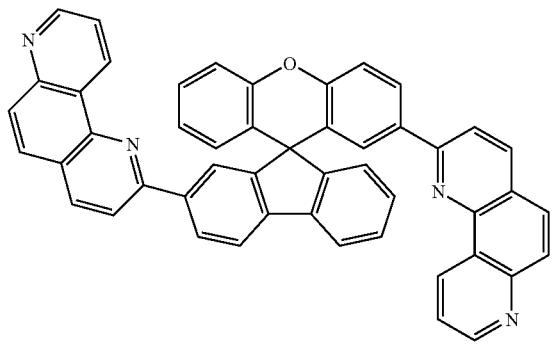
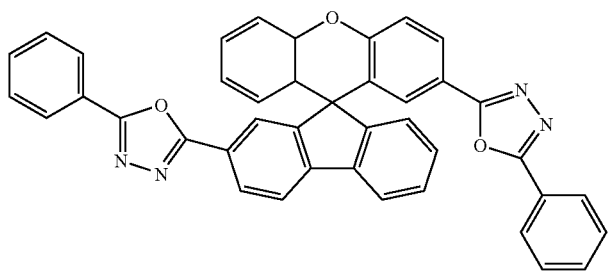

-continued
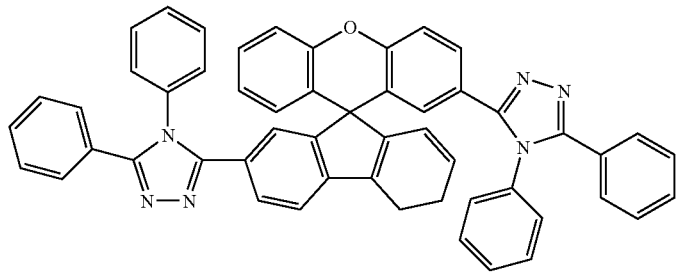
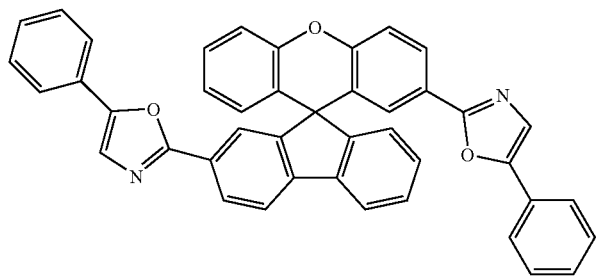
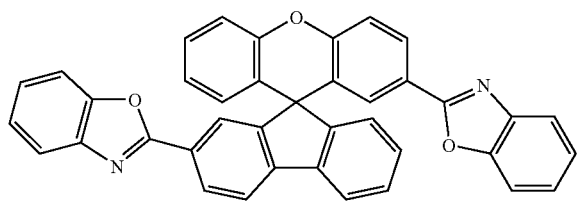
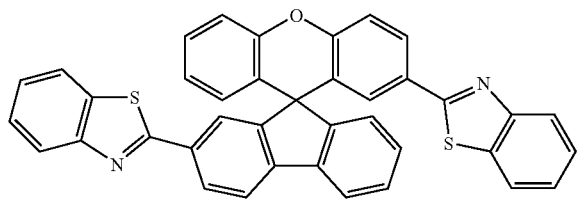
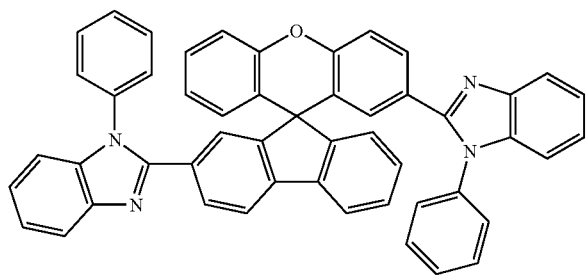
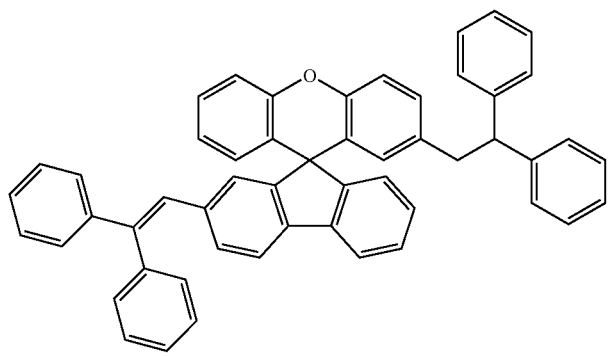

-continued
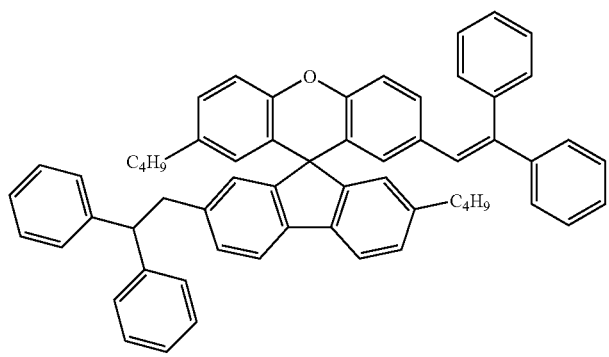
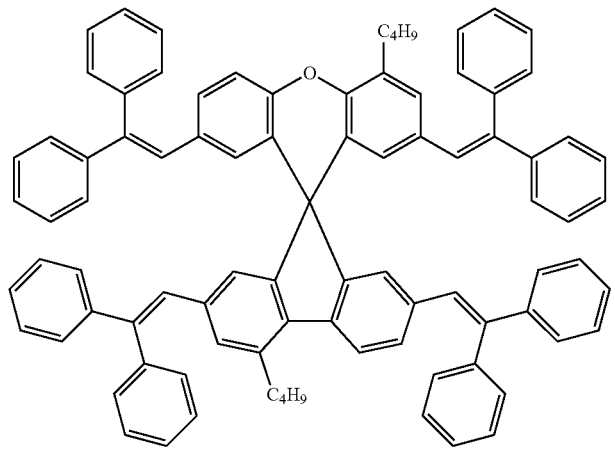
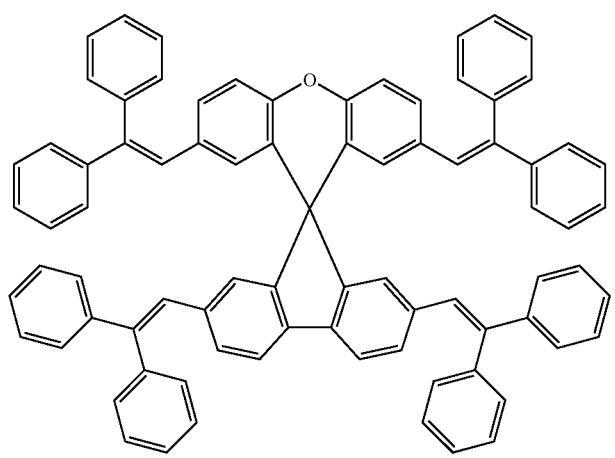

-continued
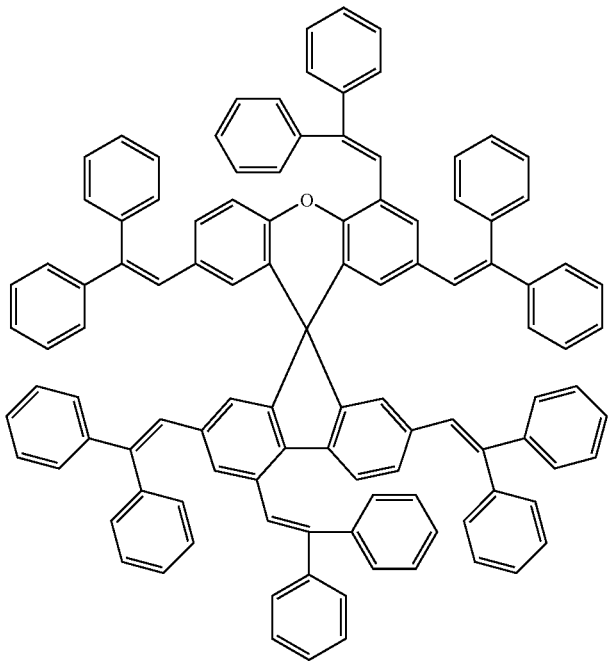
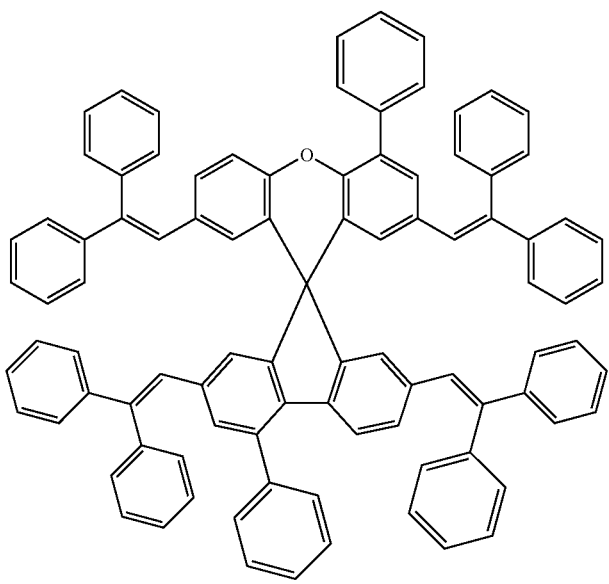
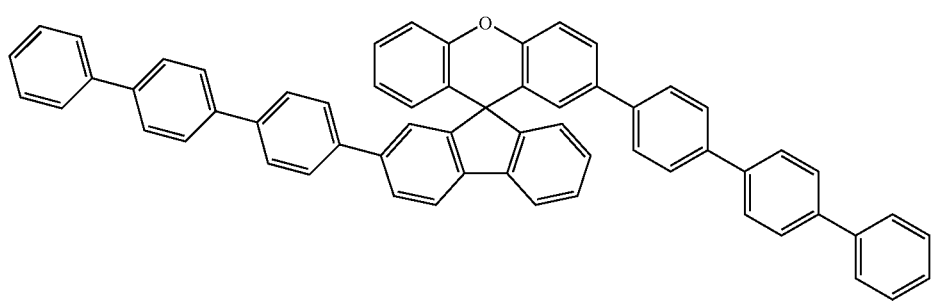

-continued

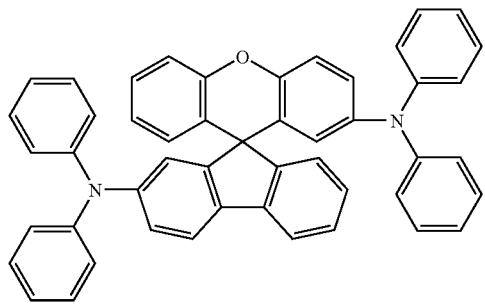

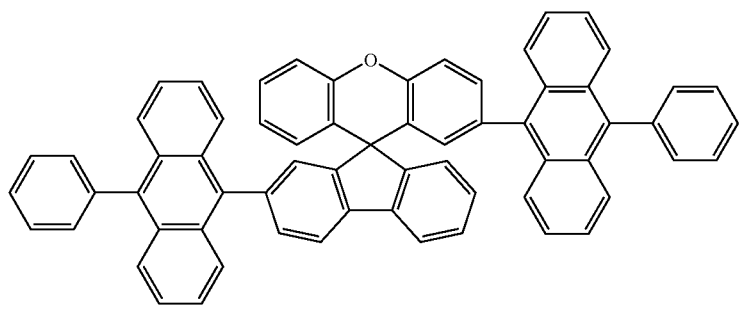

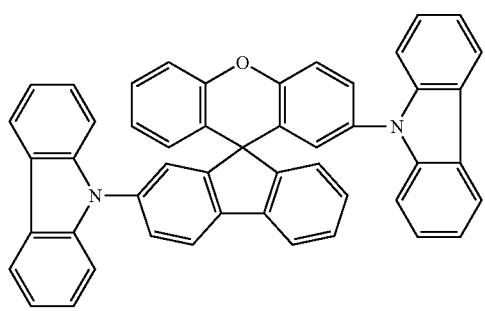

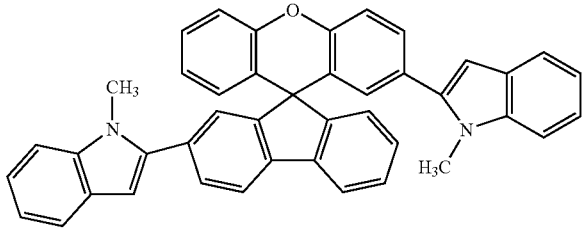

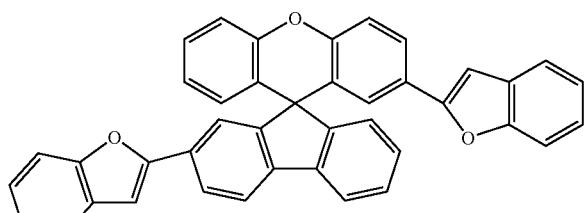

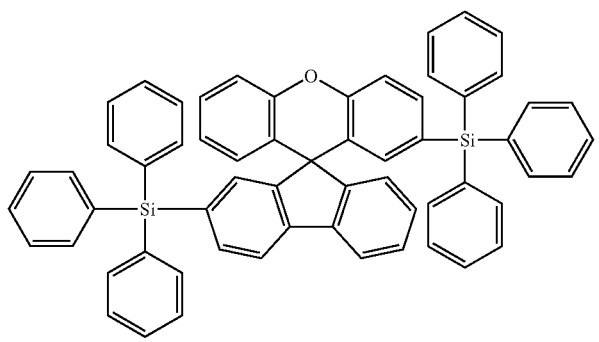

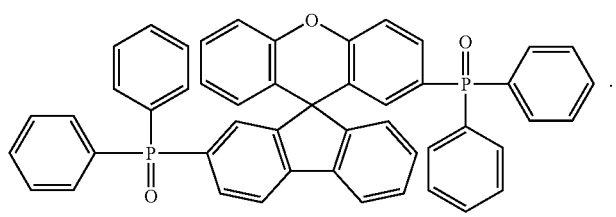

8. The display comprising the light emitting device of claim 7.

9. A light emitting device comprising an anode, an emissive layer, an electron transporting layer and a cathode that are provided as layers in turn, the device emits light by electrical energy and said electron transporting layer comprises a tetraphenylmethane derivative selected from formulas below:

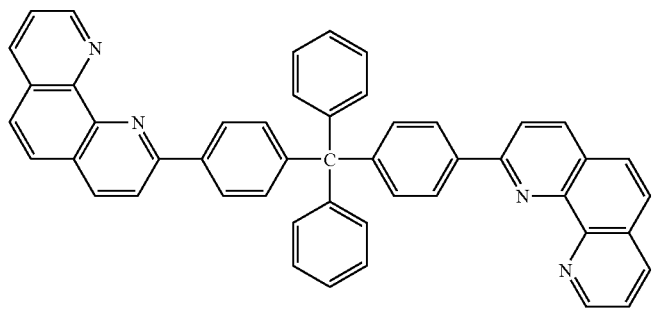
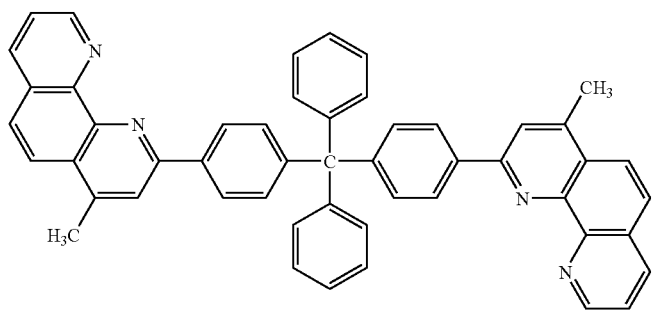
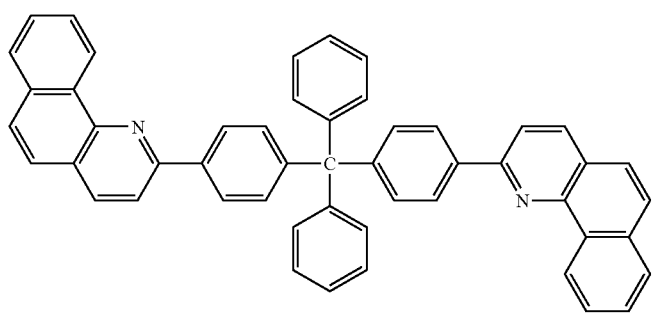
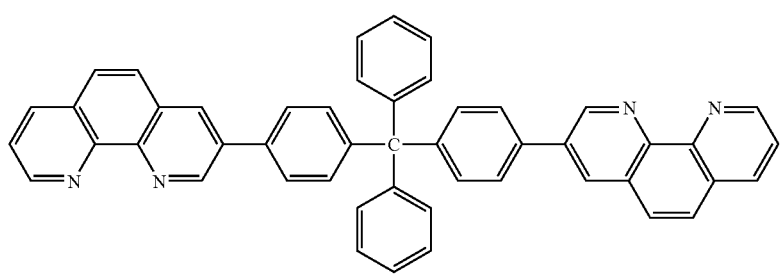
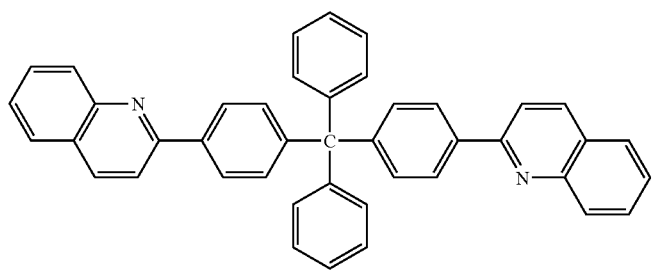

-continued
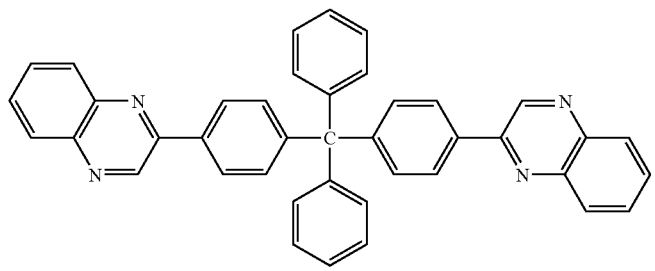
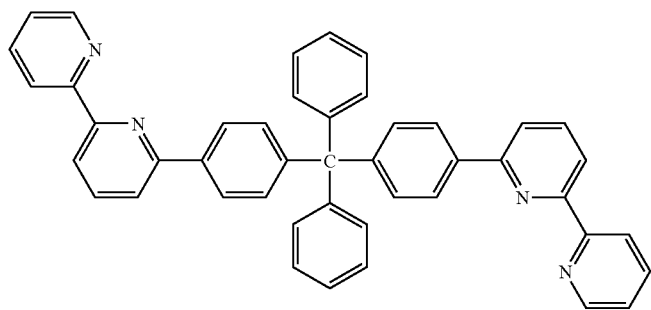
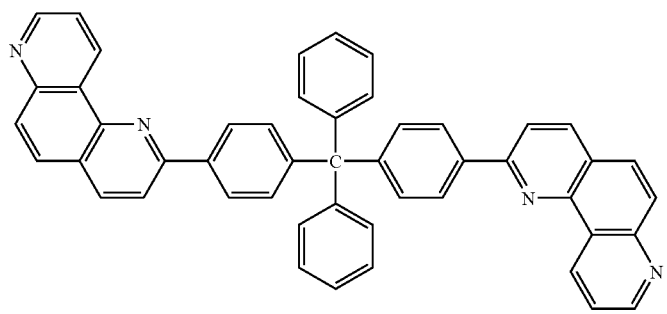
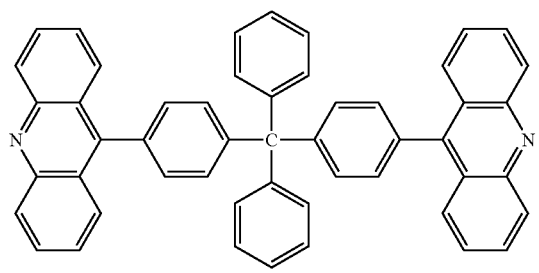
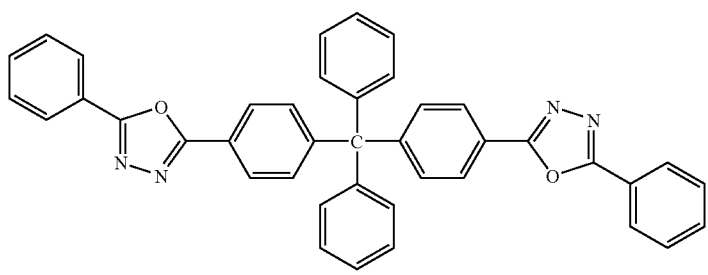

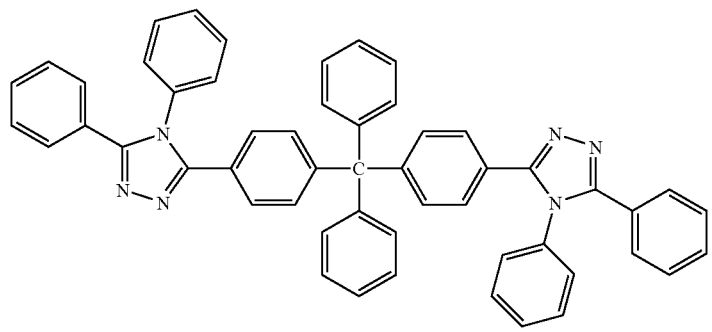
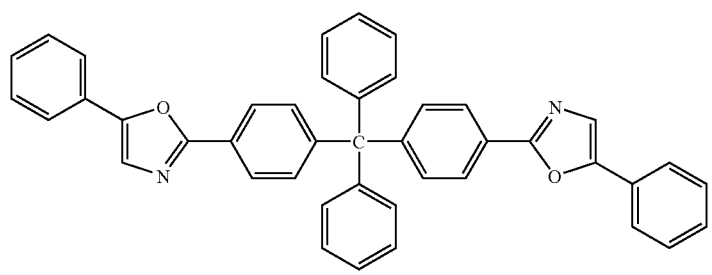
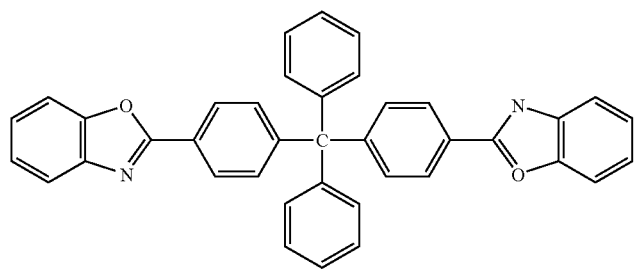
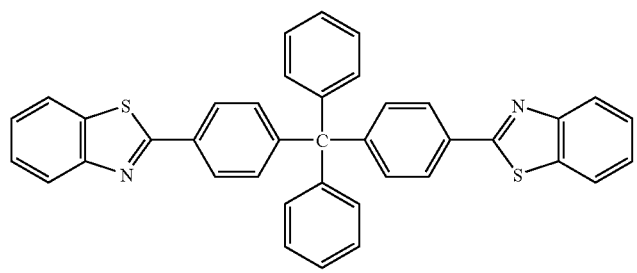
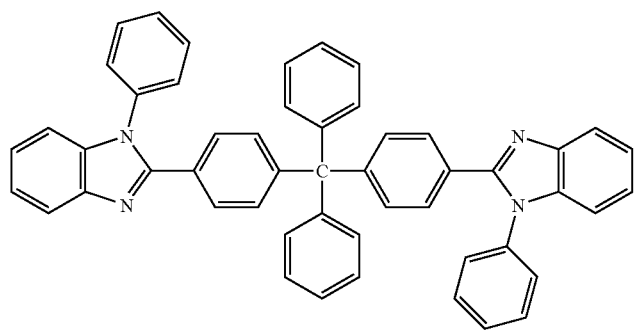

-continued
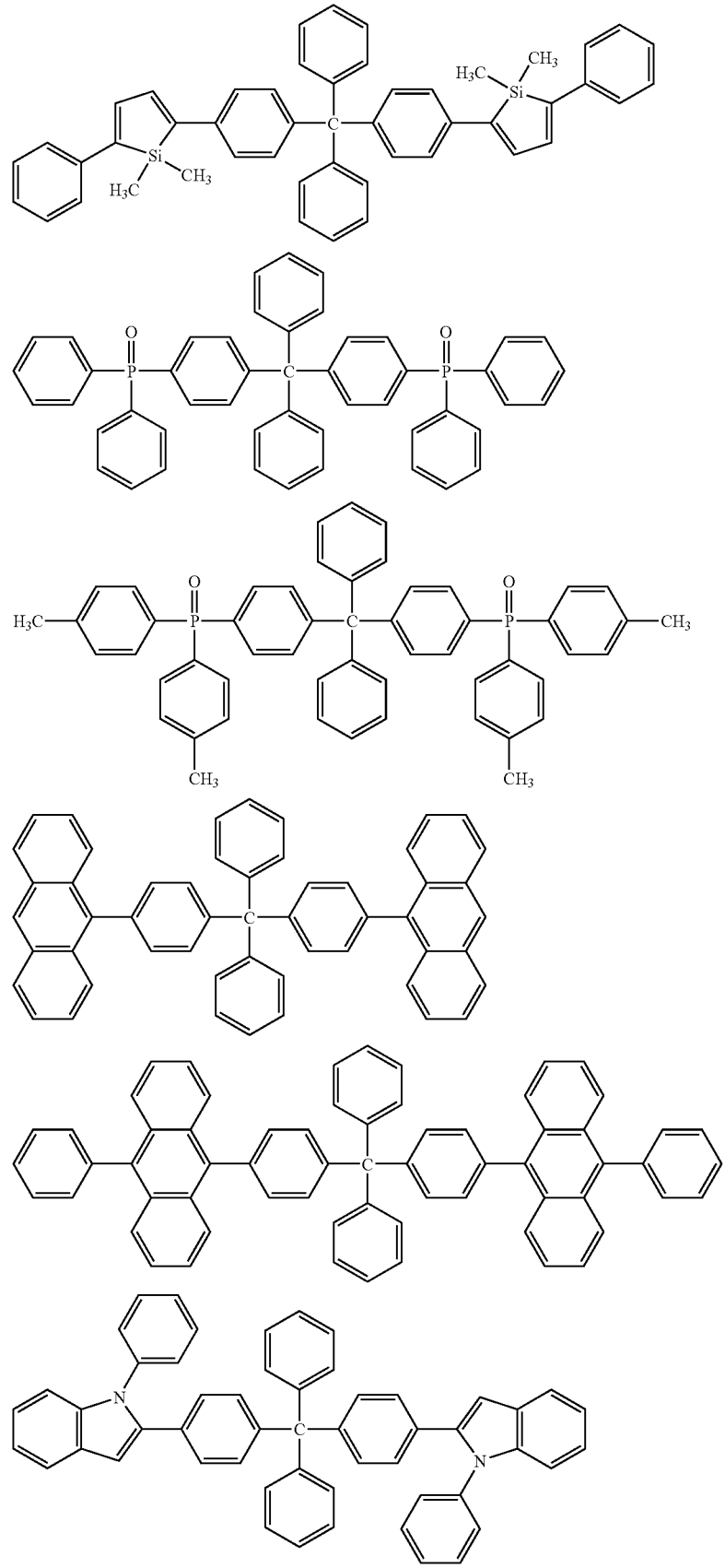

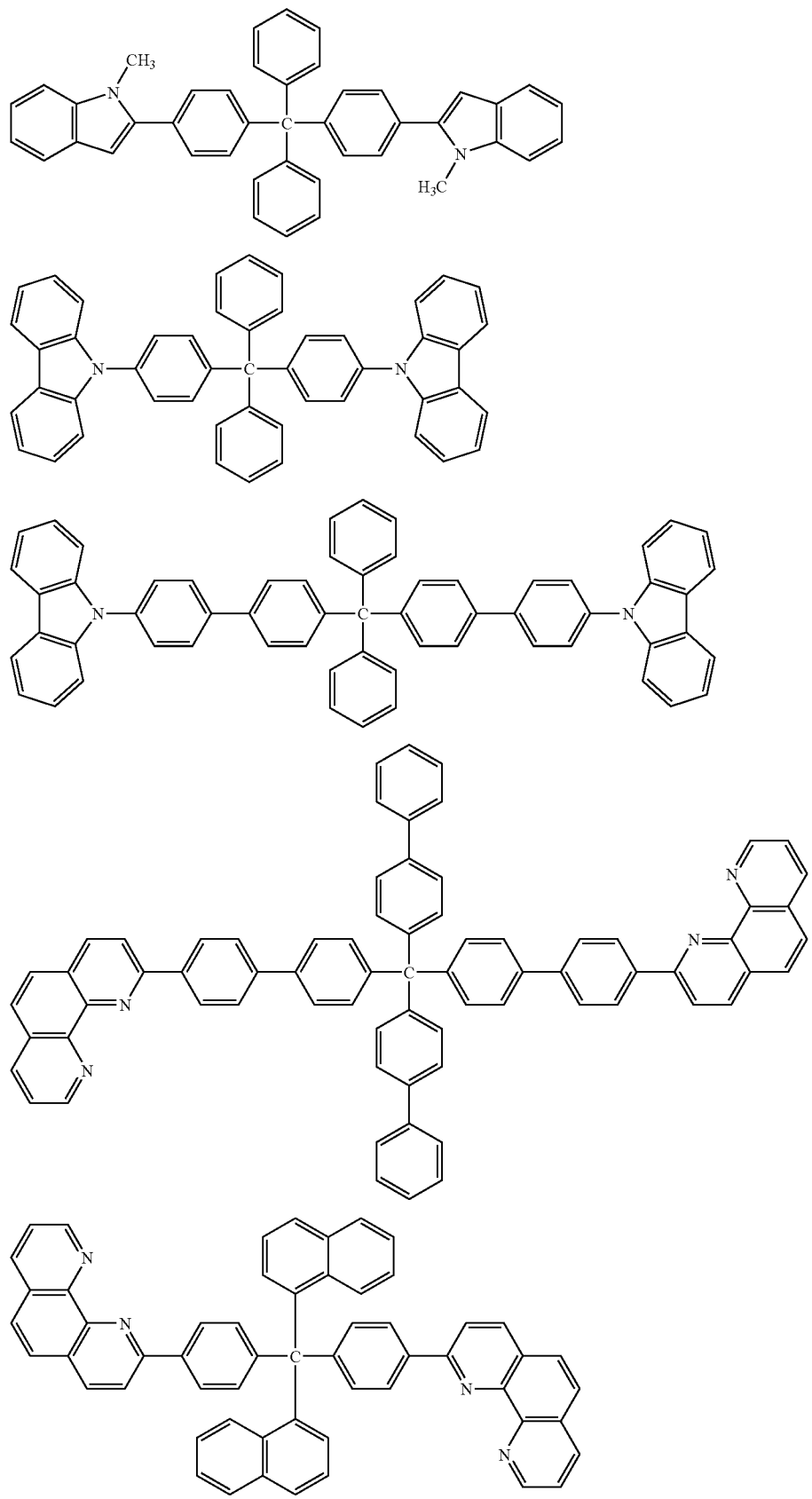

-continued
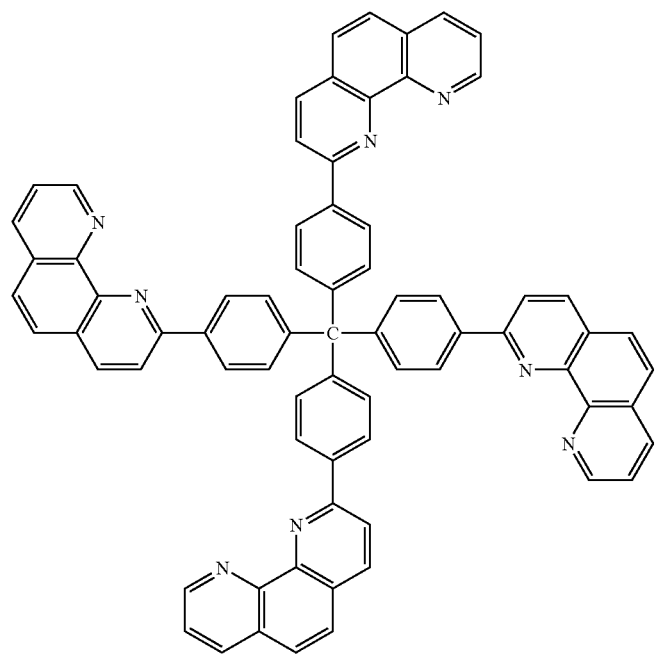
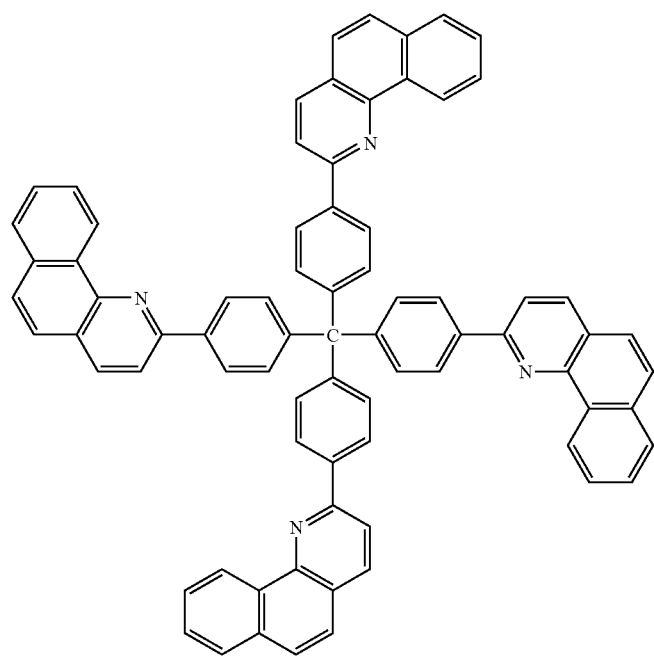

-continued
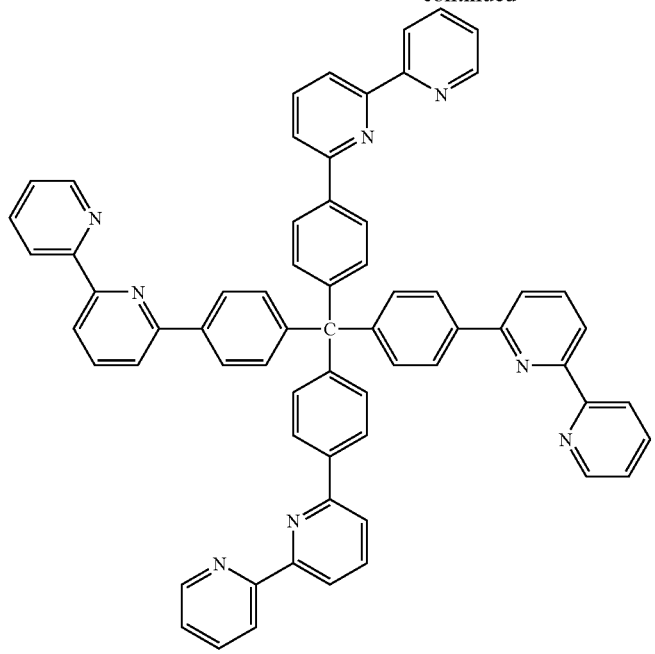
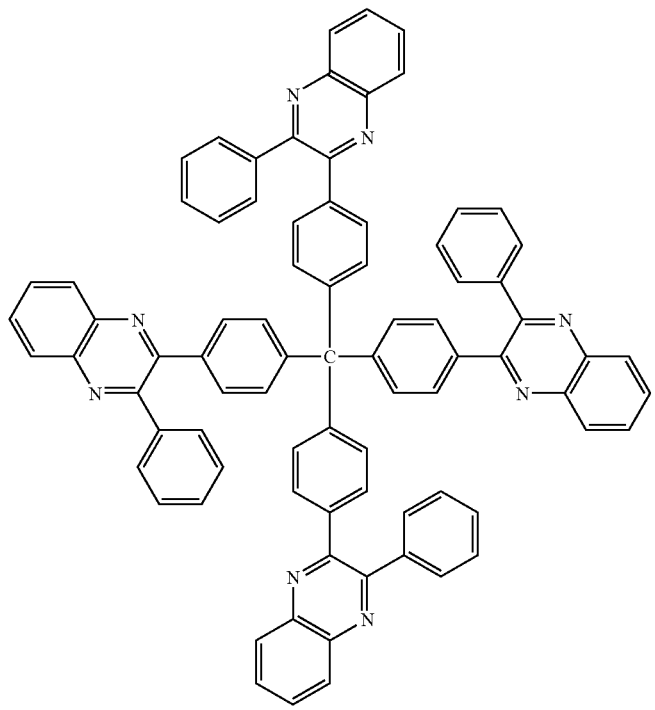
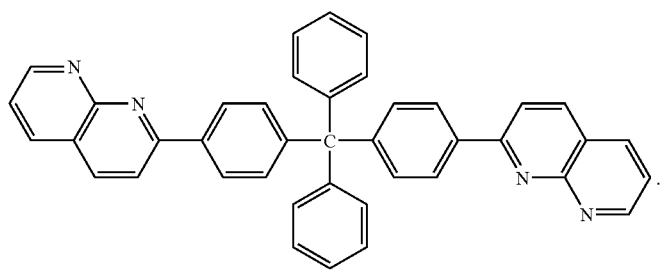

10. The display comprising the light emitting device of claim 7.

11. A light emitting device comprising an anode, an emissive layer, an electron transporting layer and a cathode that are provided as layers in turn, wherein the device emits light by electrical energy and the emissive layer comprises a plurality of 1,7-phenanthroline skeletal structures or a plurality of benzoquinoline skeletal structures.

12. The light emitting device of claim 11, wherein the plurality of phenanthroline skeletal structures or the plurality of benzoquinoline skeletal structures are connected by conjugated bonds, an aromatic hydrocarbon, an aromatic heterocycle or combinations thereof.

13. The display comprising the light emitting device of claim 11.

14. Spiro compounds selected form formulas below:

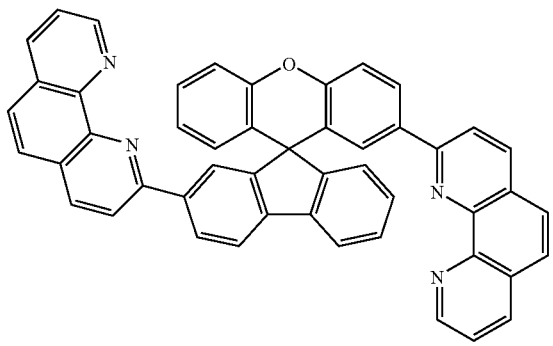
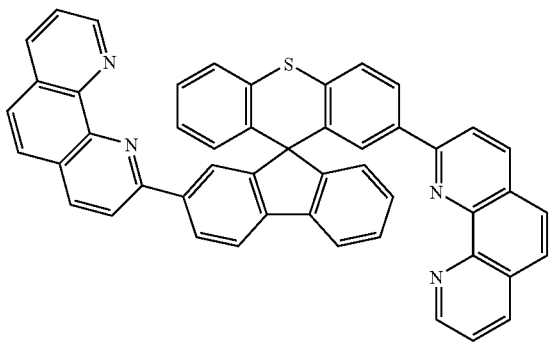
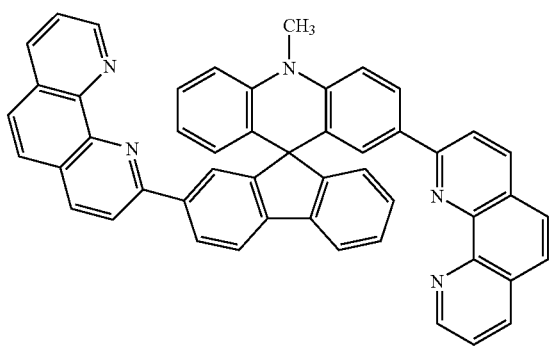
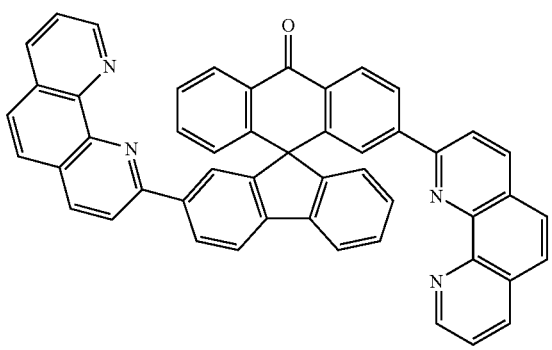
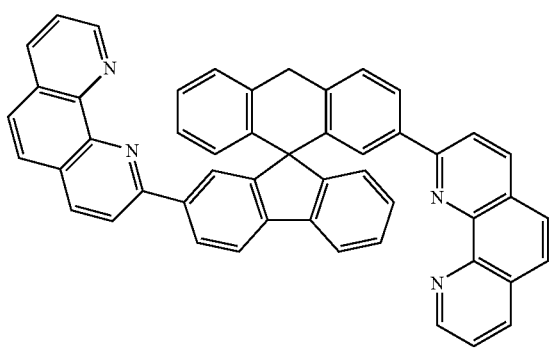
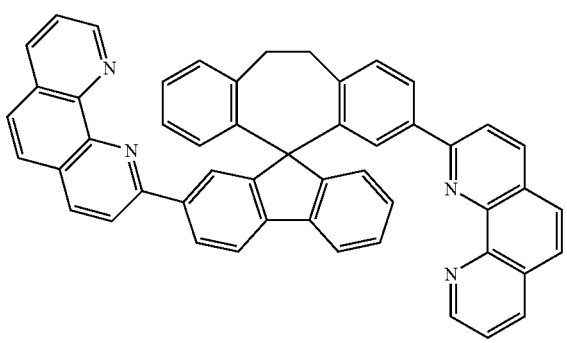
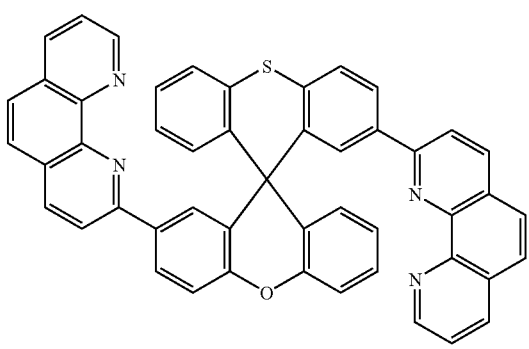
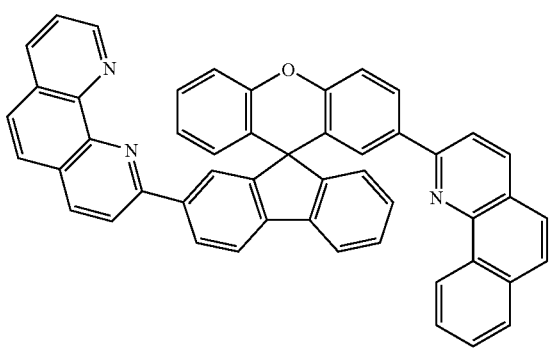

-continued
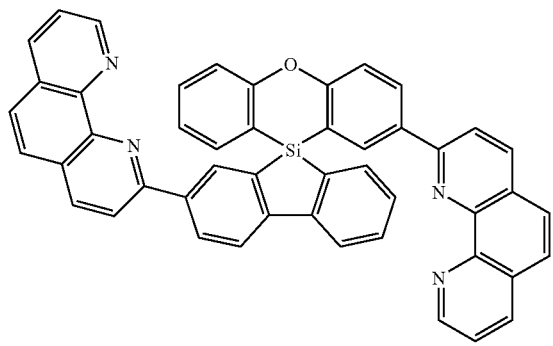
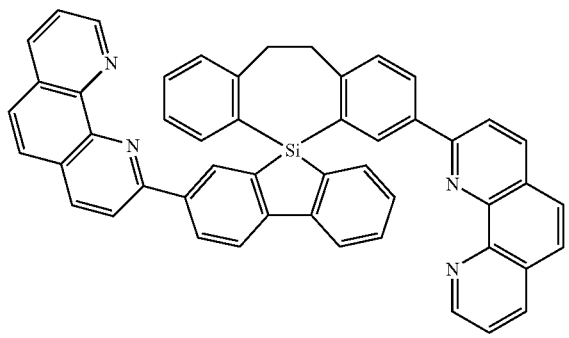
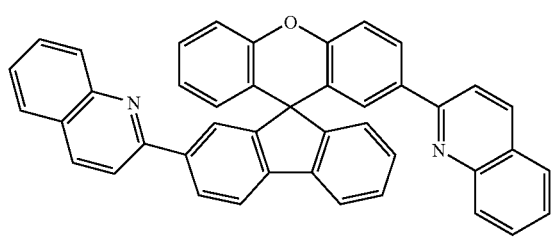
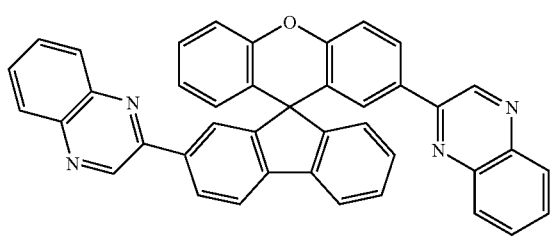
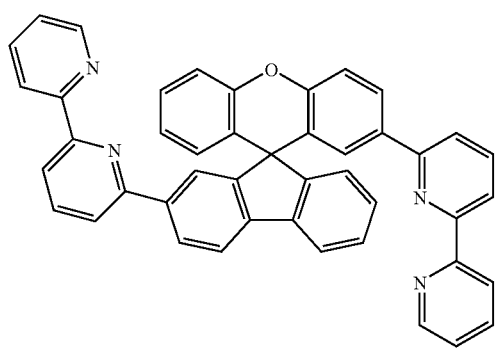
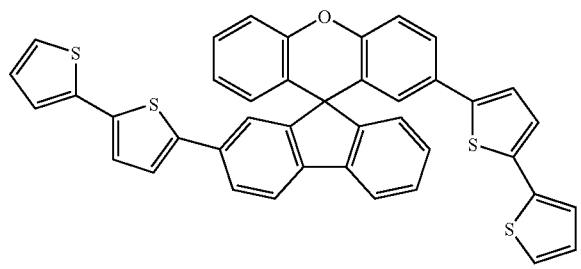
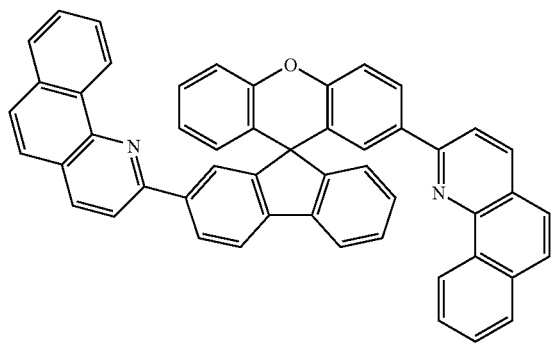
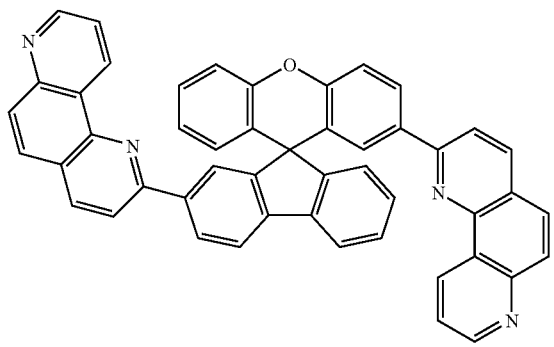
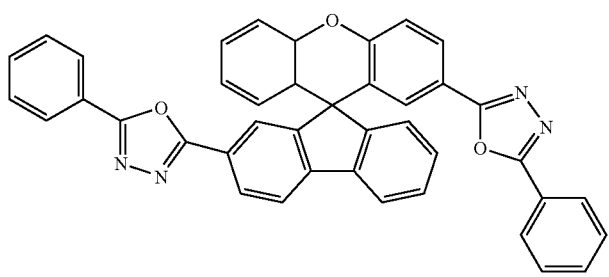

-continued
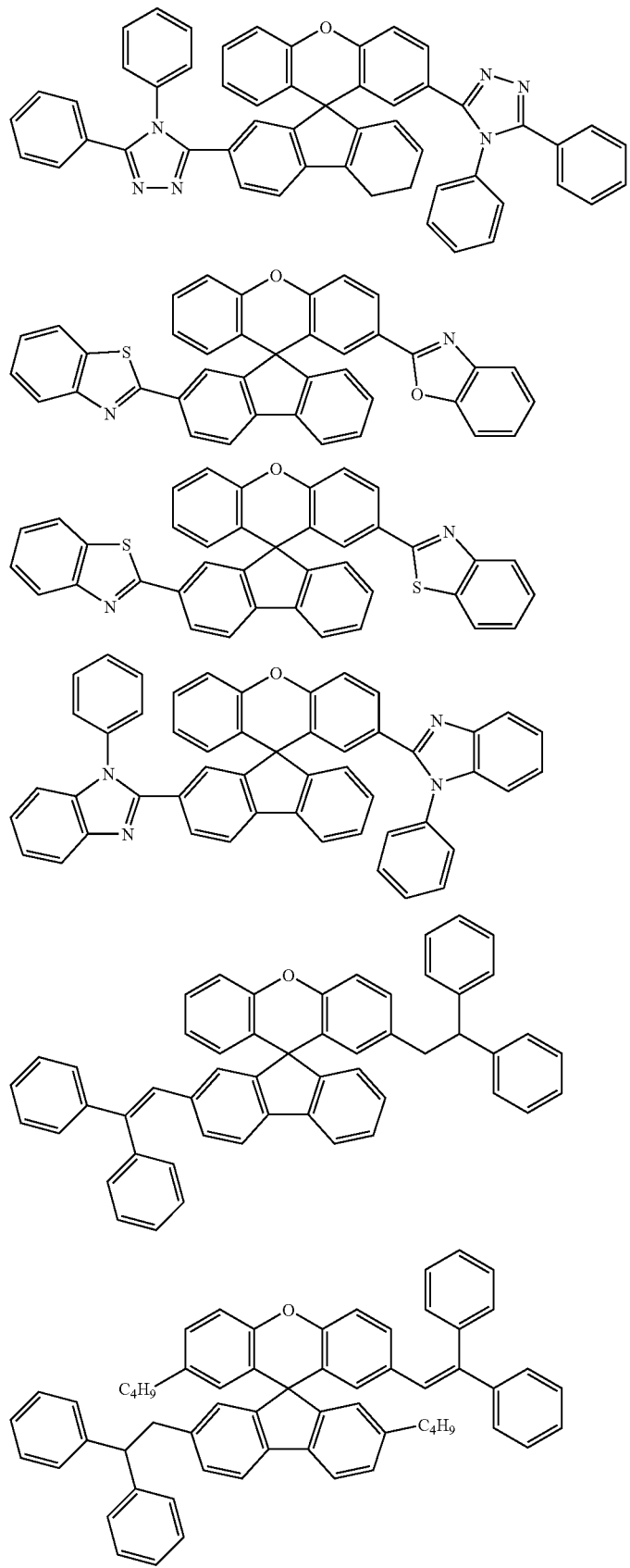

-continued
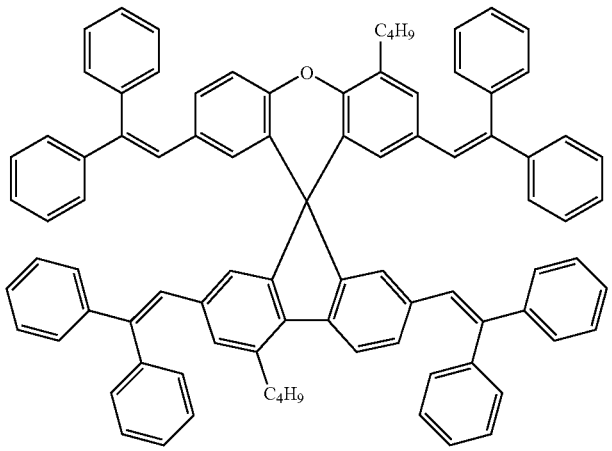
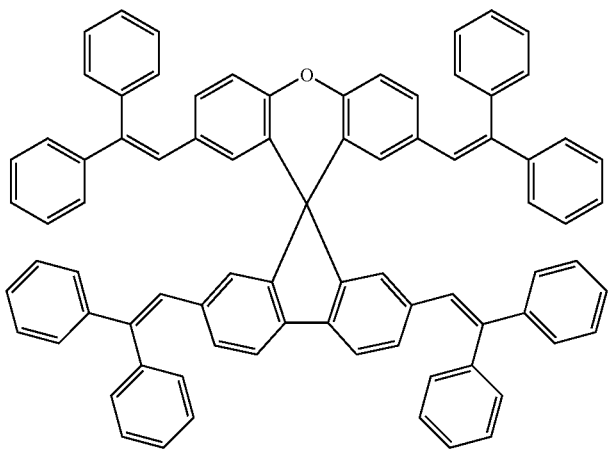
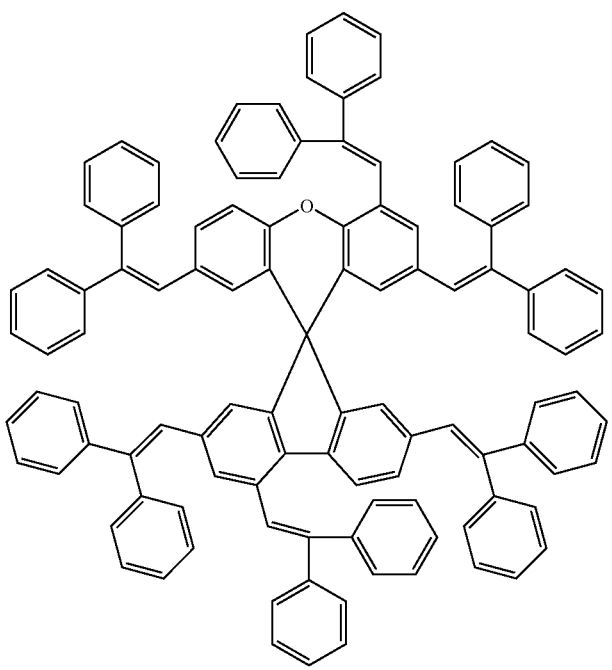

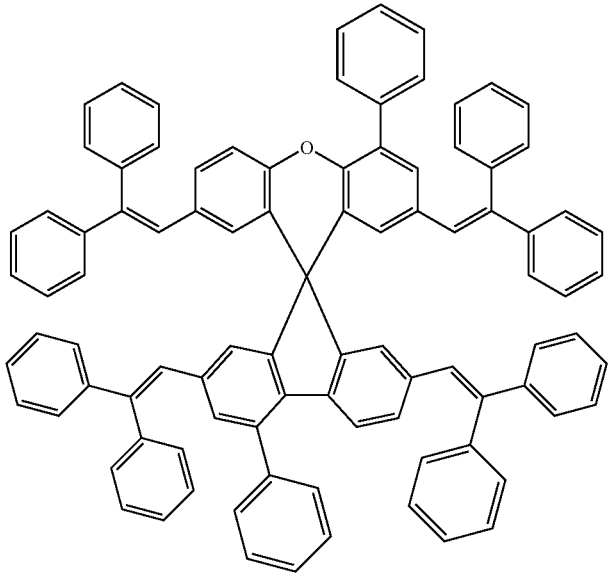
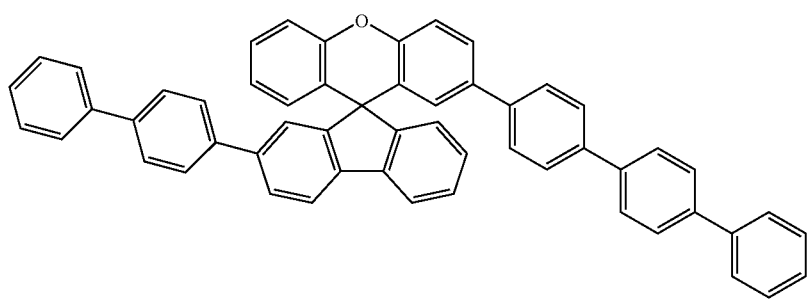
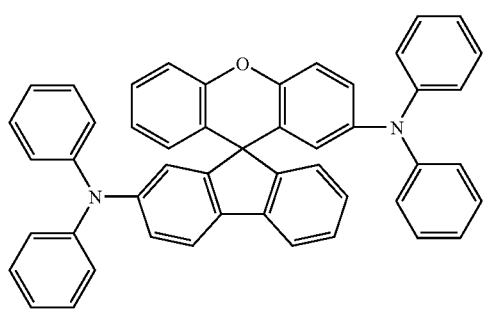
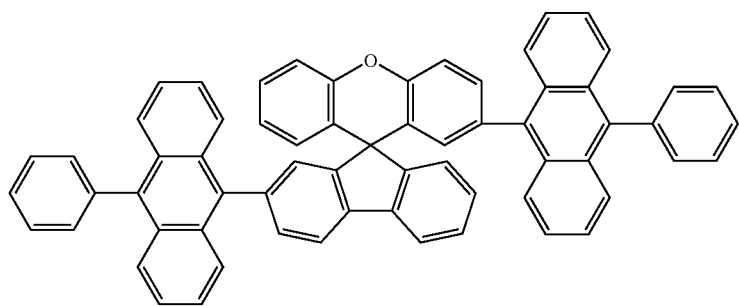

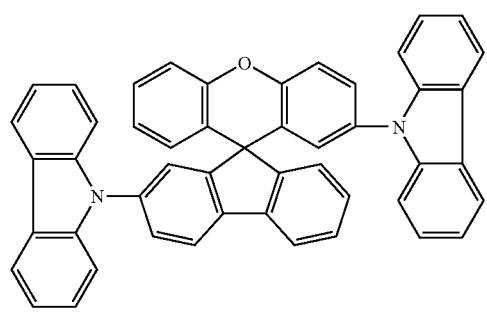
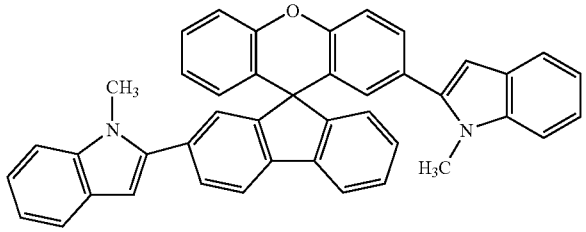
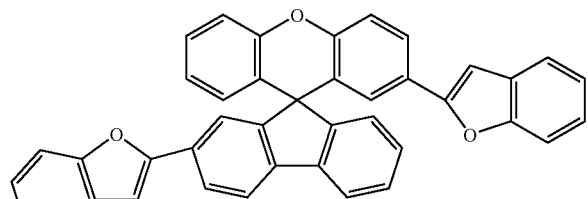
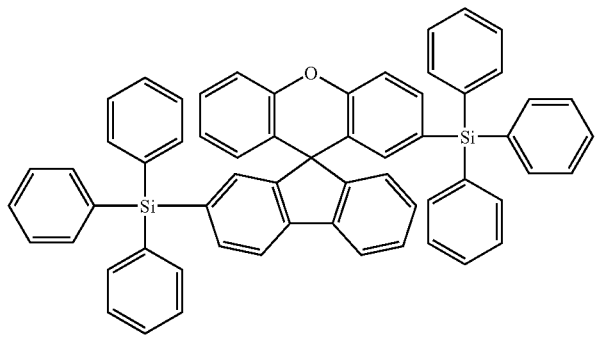
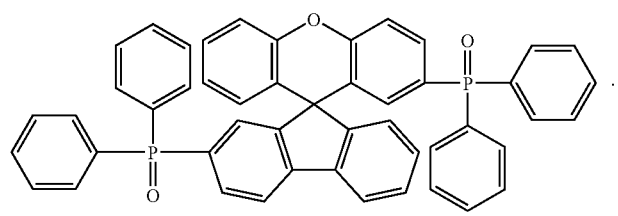
15. Tetraphenylmethane derivatives selected from formulas below:
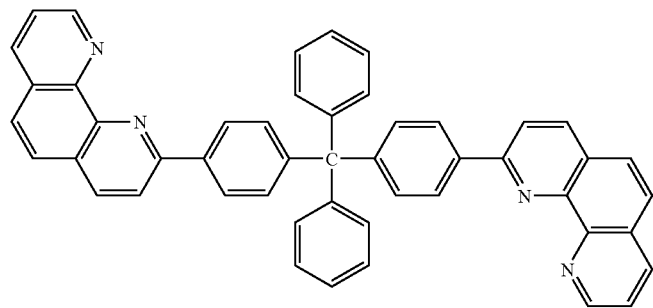
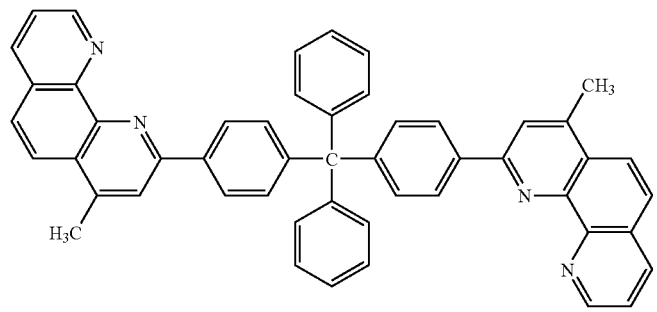

-continued
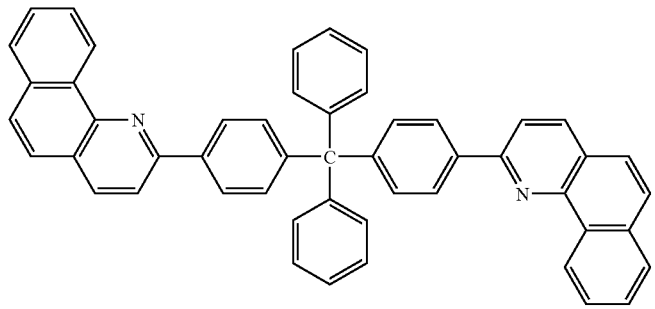
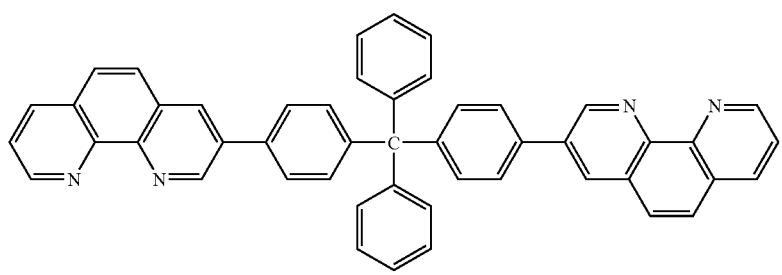
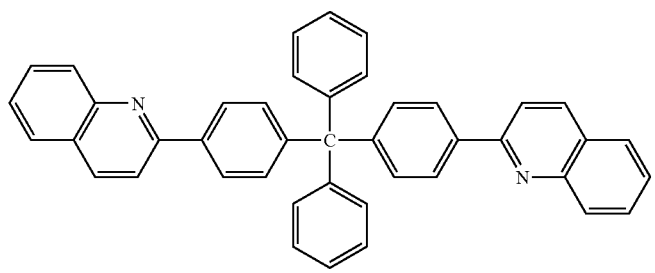
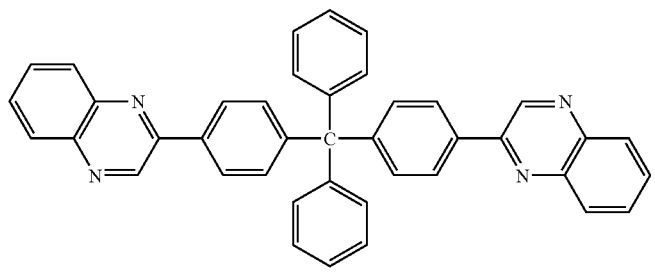
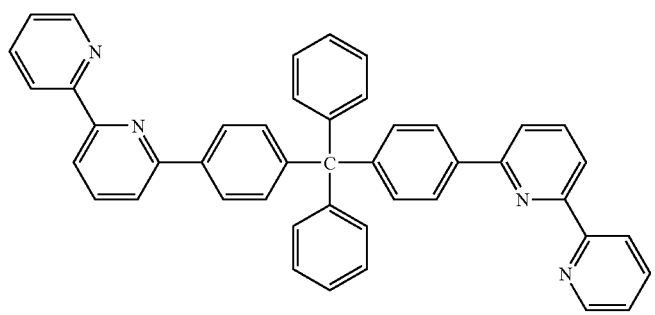

-continued
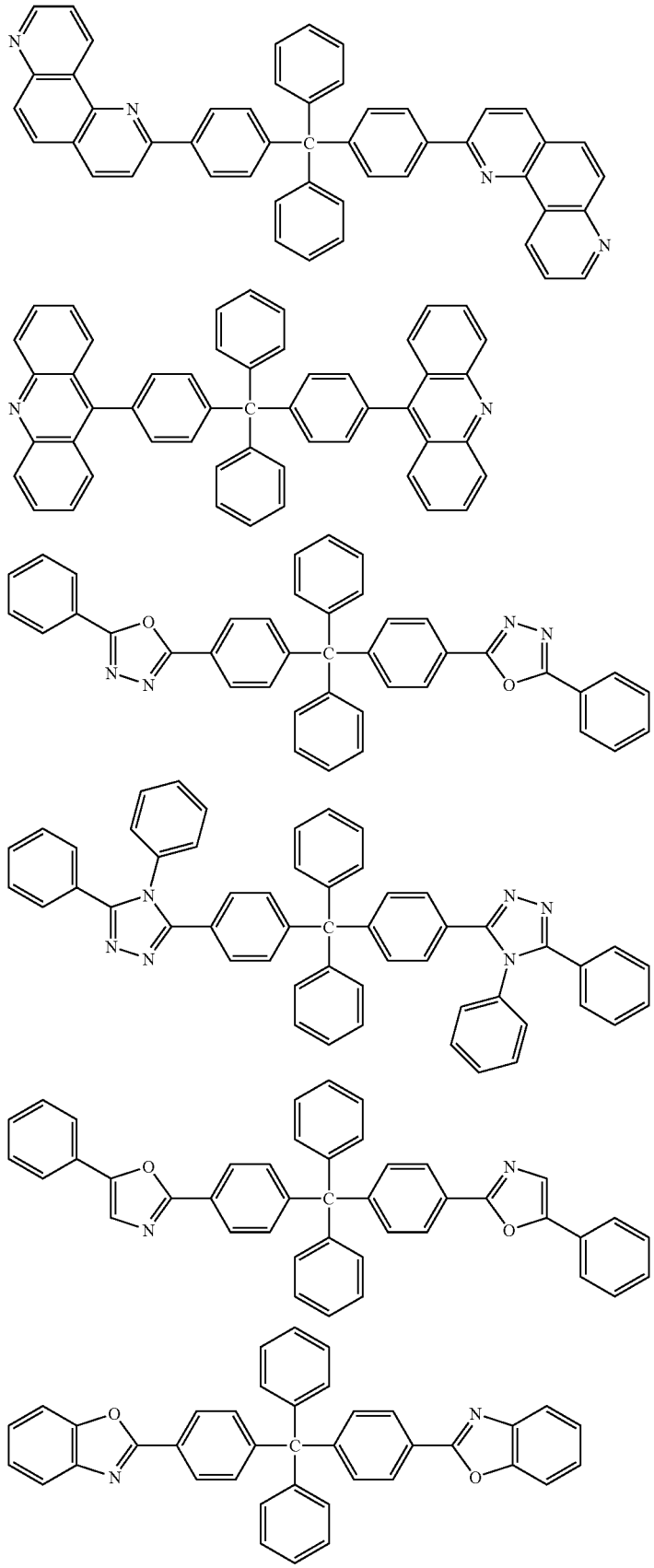

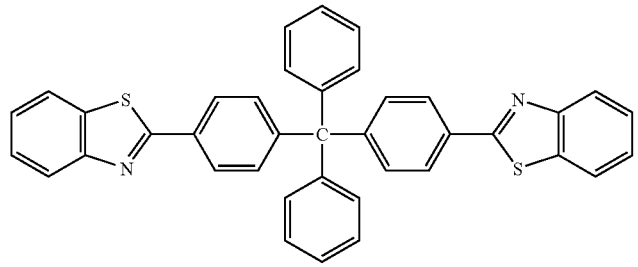
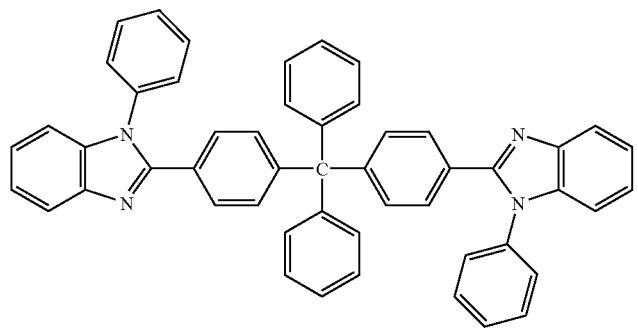
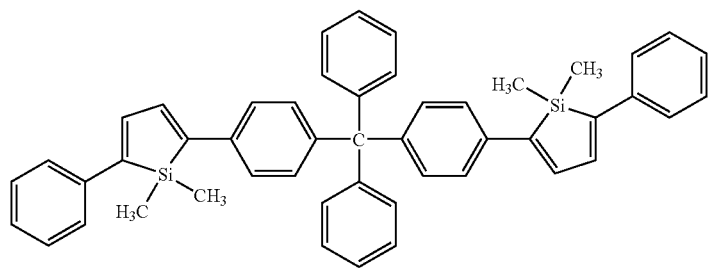
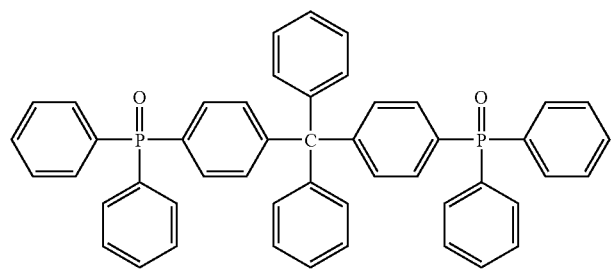
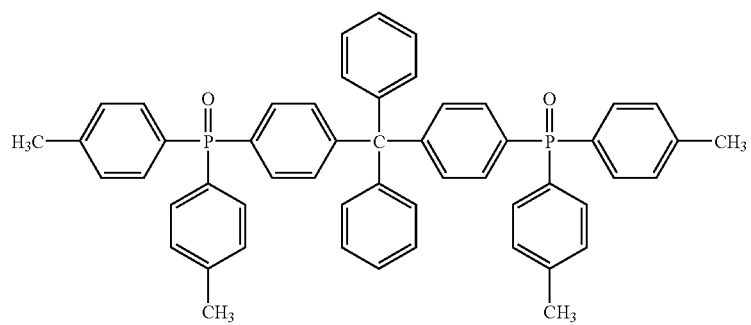

-continued
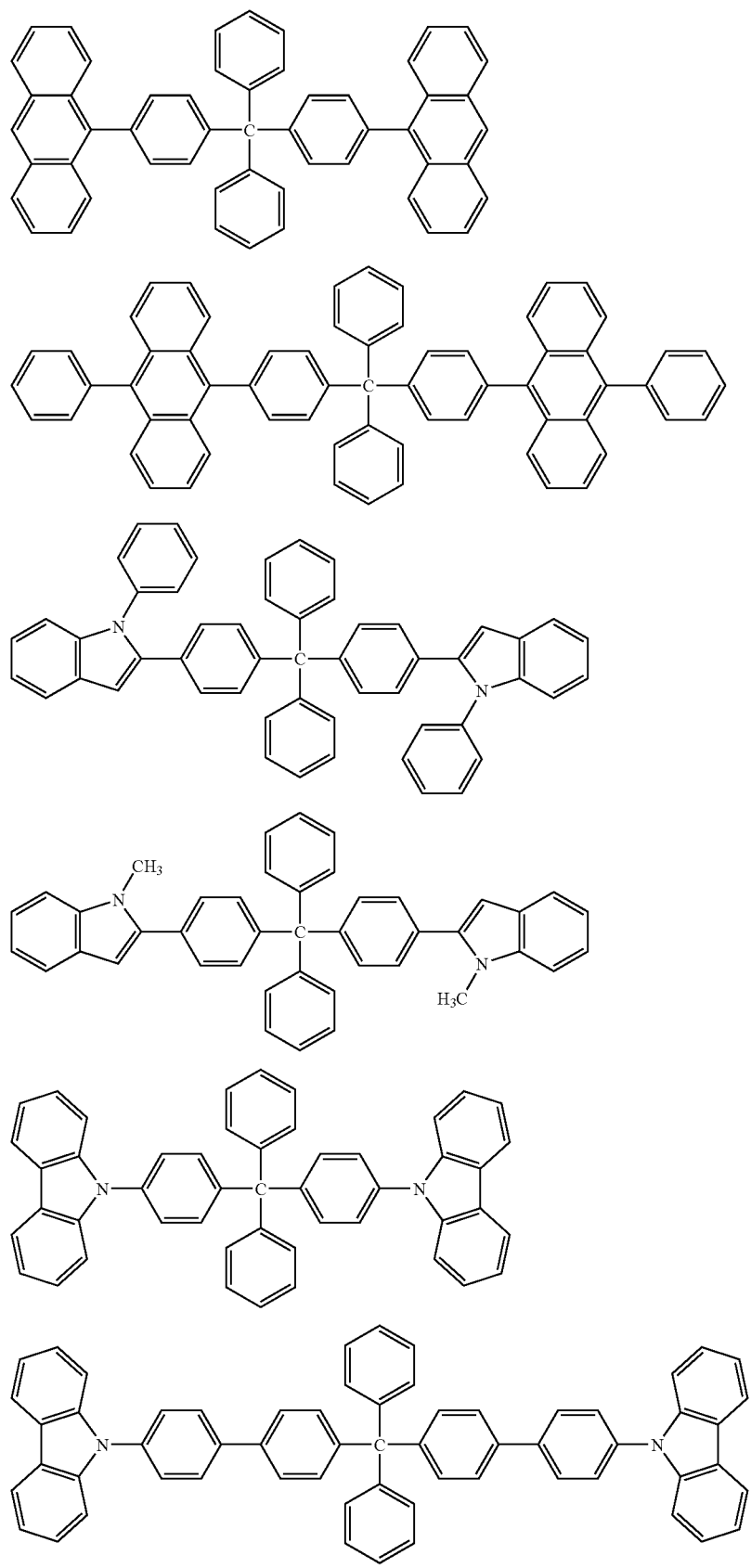

-continued
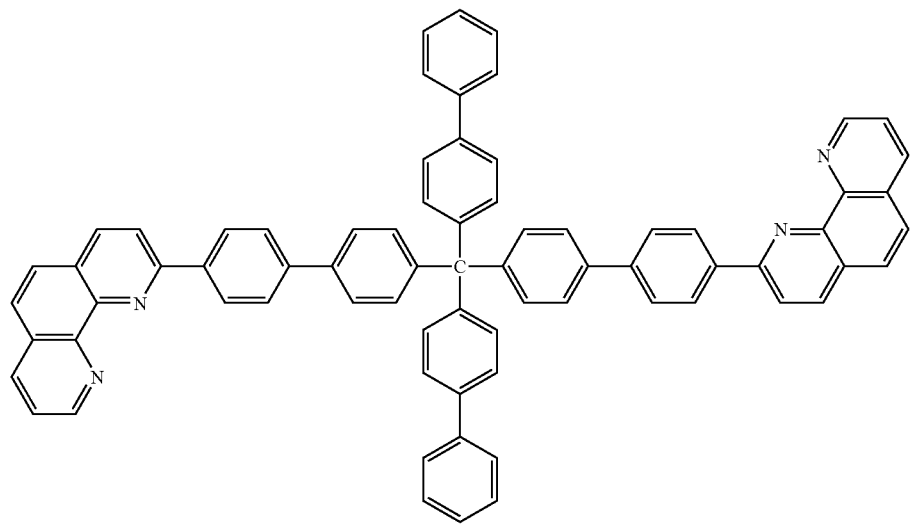
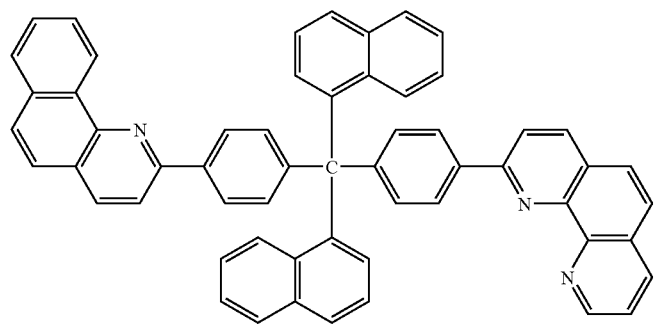
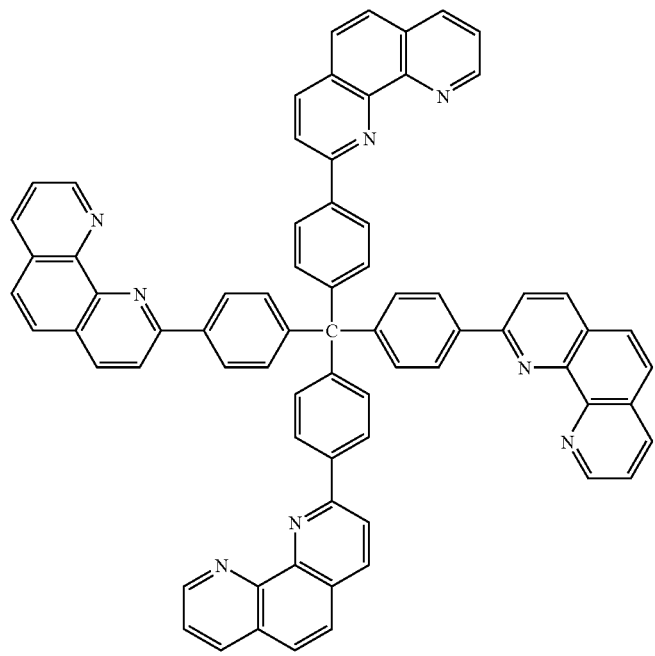

-continued
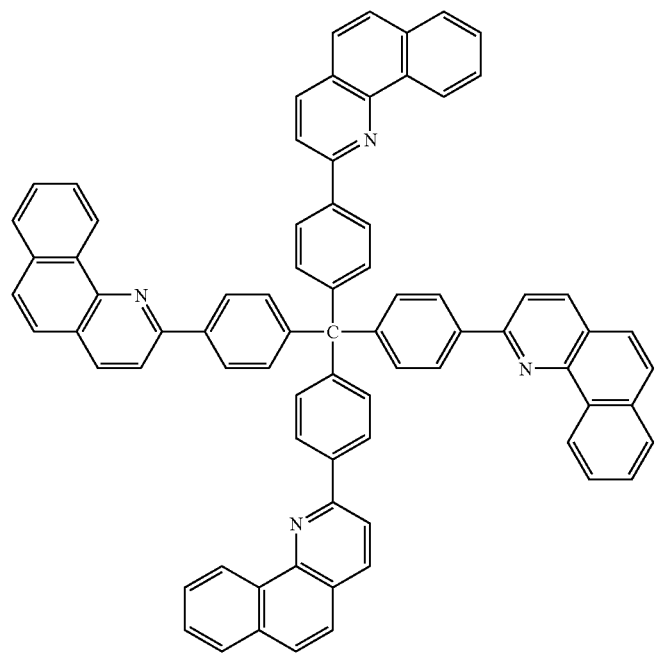
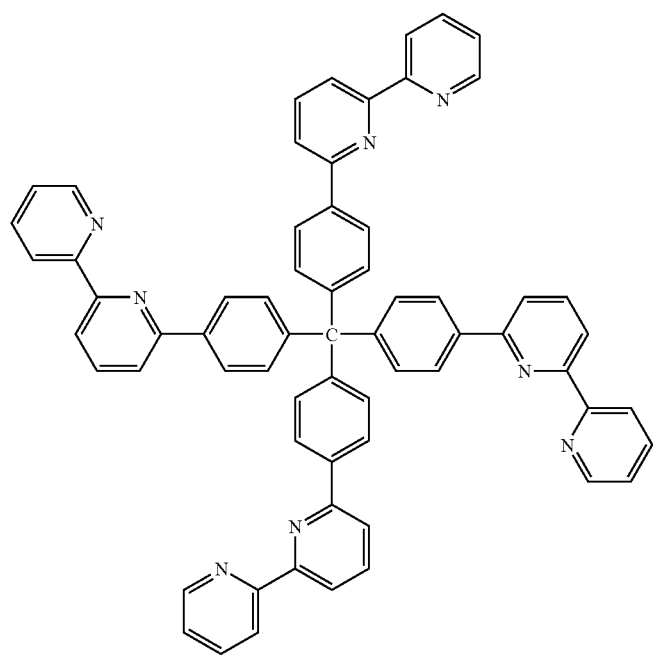

-continued
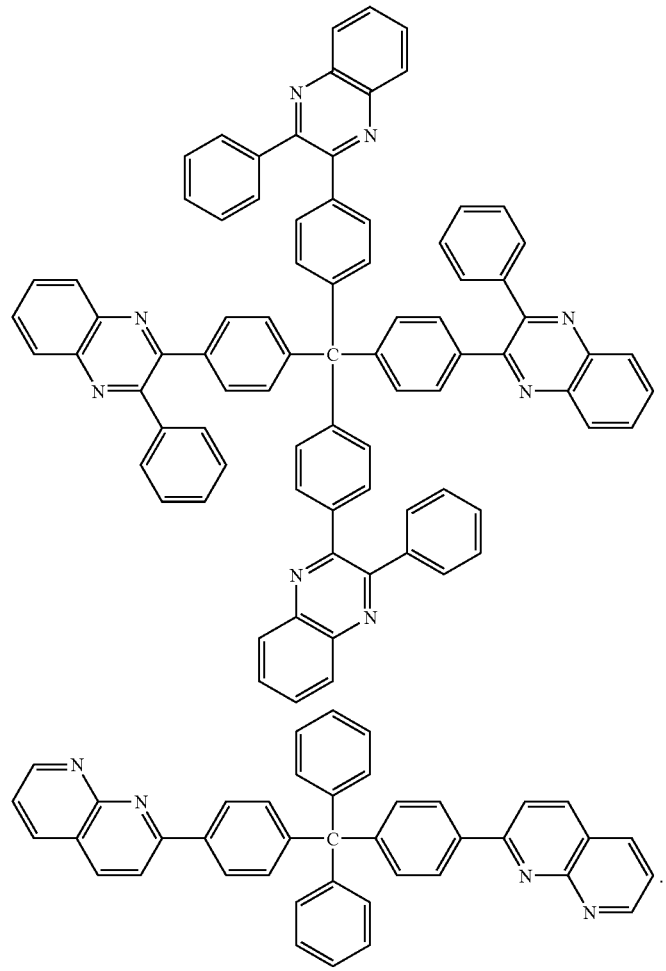
* * * * *

UNITED STATES PATENT AND TRADEMARK OFFICE
CERTIFICATE OF CORRECTION

PATENT NO.        : 7,318,966 B2                              Page 1 of 4
APPLICATION NO.   : 10/221342
DATED             : January 15, 2008
INVENTOR(S)       : Tsuyoshi Tominaga et al.

It is certified that error appears in the above-identified patent and that said Letters Patent is hereby corrected as shown below:

In the Claims:

In Claim 8, column 75, delete:

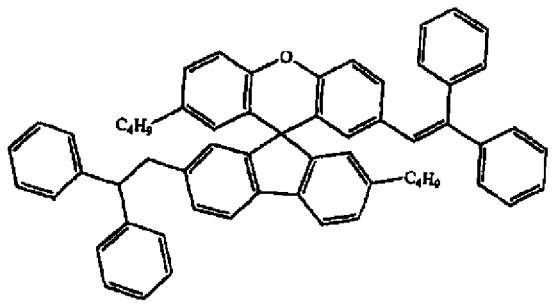

and replace with:

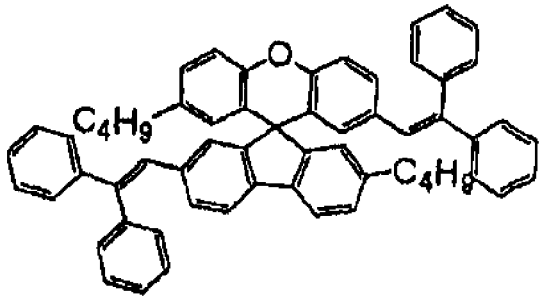

In Claim 14, column 99, delete:

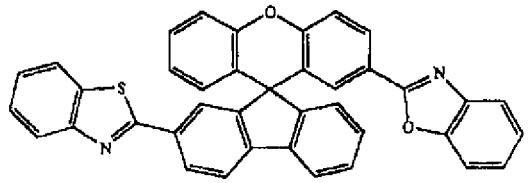

UNITED STATES PATENT AND TRADEMARK OFFICE
CERTIFICATE OF CORRECTION

PATENT NO. : 7,318,966 B2  Page 2 of 4
APPLICATION NO. : 10/221342
DATED : January 15, 2008
INVENTOR(S) : Tsuyoshi Tominaga et al.

It is certified that error appears in the above-identified patent and that said Letters Patent is hereby corrected as shown below:

and replace with:

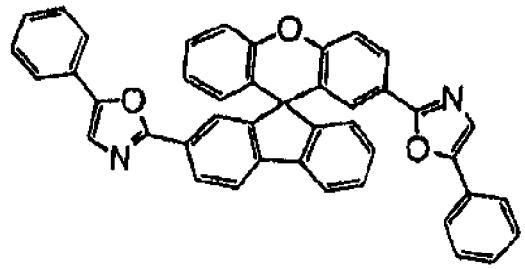

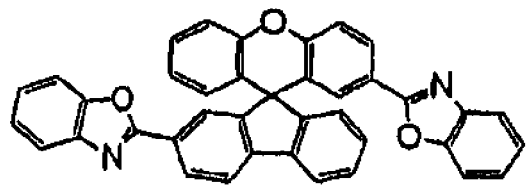

In Claim 14, column 99, delete:

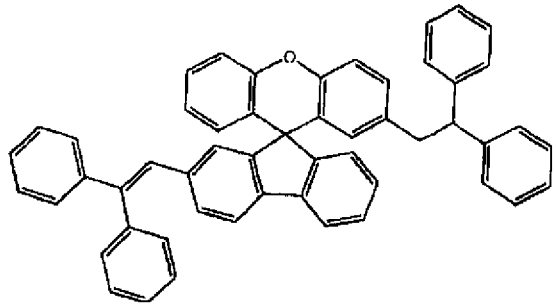

UNITED STATES PATENT AND TRADEMARK OFFICE
CERTIFICATE OF CORRECTION

PATENT NO. : 7,318,966 B2  
APPLICATION NO. : 10/221342  
DATED : January 15, 2008  
INVENTOR(S) : Tsuyoshi Tominaga et al.

It is certified that error appears in the above-identified patent and that said Letters Patent is hereby corrected as shown below:

and replace with:

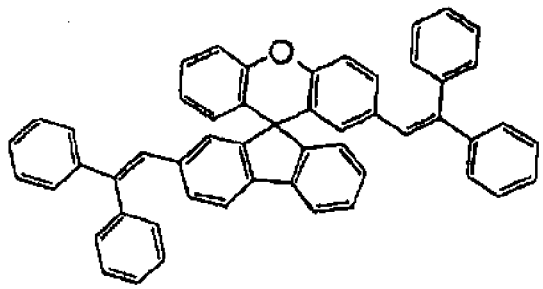

In Claim 14, column 99, delete:

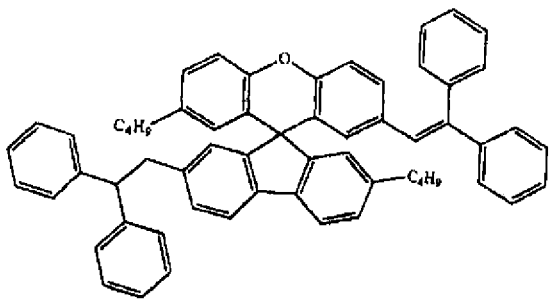

and replace with:

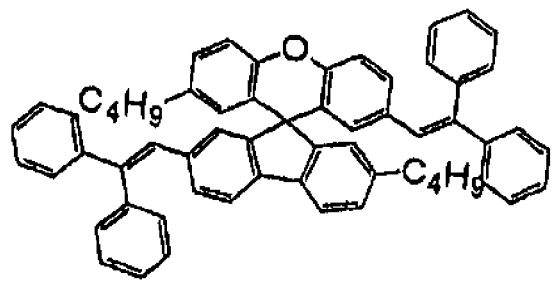

UNITED STATES PATENT AND TRADEMARK OFFICE
CERTIFICATE OF CORRECTION

PATENT NO. : 7,318,966 B2
APPLICATION NO. : 10/221342
DATED : January 15, 2008
INVENTOR(S) : Tsuyoshi Tominaga et al.

It is certified that error appears in the above-identified patent and that said Letters Patent is hereby corrected as shown below:

In Claim 15, column 115, delete:

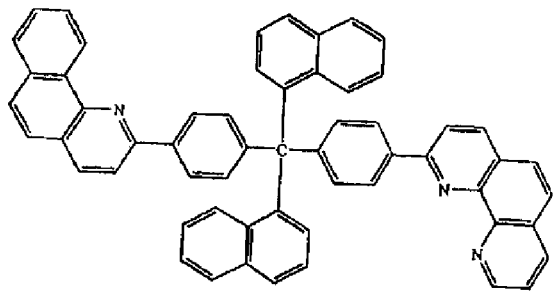

and replace with:

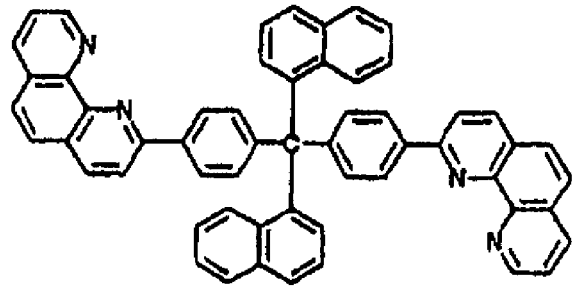

Signed and Sealed this

Twenty-fifth Day of November, 2008

JON W. DUDAS
*Director of the United States Patent and Trademark Office*